(12) United States Patent
Atlas et al.

(10) Patent No.: US 8,954,373 B2
(45) Date of Patent: Feb. 10, 2015

(54) MONITORING DEVICE FOR MANAGEMENT OF INSULIN DELIVERY

(75) Inventors: Eran Atlas, Petach Tiqwa (IL); Revital Nimri, Petach Tiqwa (IL); Shahar Miller, Petach Tikva (IL); Eli Aviram Grunberg, Petach Tiqwa (IL); Moshe Phillip, Givaataim (IL)

(73) Assignee: DreaMed Diabetes Ltd., Tel Aviv (IL)

( * ) Notice: Subject to any disclaimer, the term of this patent is extended or adjusted under 35 U.S.C. 154(b) by 213 days.

(21) Appl. No.: 13/434,326

(22) Filed: Mar. 29, 2012

(65) Prior Publication Data

US 2012/0246106 A1 Sep. 27, 2012

Related U.S. Application Data

(63) Continuation-in-part of application No. PCT/IL2010/000686, filed on Aug. 24, 2010.

(60) Provisional application No. 61/300,874, filed on Feb. 3, 2010, provisional application No. 61/247,017, filed on Sep. 30, 2009.

(51) Int. Cl.
*G06N 7/00* (2006.01)
*G06F 19/00* (2011.01)
(Continued)

(52) U.S. Cl.
CPC .......... *G06F 19/345* (2013.01); *A61B 5/14532* (2013.01); *G06F 19/3468* (2013.01); *A61M 5/1723* (2013.01); *A61M 2005/14208* (2013.01); *A61M 2230/201* (2013.01)
USPC .......................................................... 706/52

(58) Field of Classification Search
CPC .. A61K 38/28; A61B 5/14532; A61B 5/4839; A61M 5/14244; A61M 5/1723; G06F 19/3468; G06F 19/3456

USPC .......................................................... 706/52
See application file for complete search history.

(56) References Cited

U.S. PATENT DOCUMENTS

| 509,784 | A | 11/1893 | Wurts |
| 6,544,212 | B2 | 4/2003 | Galley et al. |

(Continued)

FOREIGN PATENT DOCUMENTS

| CN | 101214373 | 7/2008 |
| EP | 0 806 738 A1 | 11/1997 |

(Continued)

OTHER PUBLICATIONS

Steil et al., "Closed-loop insulin delivery—the path to physiological glucose control," *Advanced Drug Delivery Reviews*, 2004, pp. 125-144, vol. 56.

(Continued)

*Primary Examiner* — Wilbert L Starks
*Assistant Examiner* — Michael Zidanic
(74) *Attorney, Agent, or Firm* — Frommer Lawrence & Haug LLP; William S. Frommer

(57) ABSTRACT

Monitoring system and method for use with diabetic treatment management. The system includes: a communication interface configured to permit access to stored raw log data, obtained over a certain time, being indicative of glucose measurements, meals consumed and insulin delivery; and a control unit including an unsupervised learning controller configured to receive and process said raw log data and determine at least one global insulin pump setting of basal rate, correction factor, carbohydrate ratio and insulin activity curve parameters. The system may include a processing unit including a first processor for processing measured data indicative of blood glucose level and generating first processed data, a second processor including at least one fuzzy logic module which receives input parameters corresponding to the measured data, the first processed data and a reference data, and processes the data to produce a qualitative output parameter to determine whether any treatment parameter should be modified.

49 Claims, 23 Drawing Sheets

(51) Int. Cl.
*A61B 5/145* (2006.01)
*A61M 5/172* (2006.01)
*A61M 5/142* (2006.01)

(56) References Cited

U.S. PATENT DOCUMENTS

| | | | |
|---|---|---|---|
| 6,558,351 | B1 | 5/2003 | Steil et al. |
| 6,572,542 | B1 | 6/2003 | Houben et al. |
| 7,734,323 | B2 | 6/2010 | Blomquist et al. |
| 7,751,907 | B2 | 7/2010 | Blomquist |
| 7,806,854 | B2 | 10/2010 | Damiano et al. |
| RE43,316 | E * | 4/2012 | Brown et al. ............ 600/309 |
| 2006/0173406 | A1 | 8/2006 | Hayes et al. |
| 2007/0066813 | A1* | 3/2007 | Prior et al. ............ 530/400 |
| 2007/0066873 | A1 | 3/2007 | Kamath et al. |
| 2008/0206799 | A1 | 8/2008 | Blomquist |
| 2008/0228056 | A1 | 9/2008 | Blomquist et al. |
| 2008/0294294 | A1 | 11/2008 | Blomquist |
| 2010/0262434 | A1* | 10/2010 | Shaya ............ 705/3 |
| 2010/0292634 | A1* | 11/2010 | Kircher et al. ............ 604/66 |
| 2012/0123234 | A1 | 5/2012 | Atlas et al. |

FOREIGN PATENT DOCUMENTS

| | | |
|---|---|---|
| JP | 2001-521804 | 11/2001 |
| JP | 2005-267364 | 9/2005 |
| JP | 2005-315855 | 11/2005 |
| JP | 2006-175227 | 7/2006 |
| JP | 2008-508934 | 3/2008 |
| JP | 2008-229331 | 10/2008 |
| JP | 2008-545489 | 12/2008 |
| JP | 2010-502361 | 1/2010 |
| JP | A-2010-512945 | 4/2010 |
| JP | 2010-519537 | 6/2010 |
| JP | 2010-521222 | 6/2010 |
| JP | 2010-524639 | 7/2010 |
| WO | WO 00/74753 A1 | 12/2000 |
| WO | WO 2006/019623 A2 | 2/2006 |
| WO | WO 2007/049961 A2 | 5/2007 |
| WO | WO 2007/120904 A2 | 10/2007 |
| WO | WO 2007/149533 A2 | 12/2007 |
| WO | WO 2008/135329 A1 | 11/2008 |

OTHER PUBLICATIONS

Parker et al, "A Model-Based Algorithm for Blood Glucose Control in Type I Diabetic Patients," *IEE Transactions on Biomedical Engineering*, 1999, pp. 148-157, vol. 46, No. 2.

Hovorka et al,, "Closing the Loop: The Adicol Experience," *Diabetes Technology & Therapeutics*, 2004, pp. 307-318, vol. 6, No. 3.

Hovorka et al., "Nonlinear Model Predictive Control of Glucose Concentration in Subjects with Type 1 Diabetes," *Physiological Measurement*, 2004, pp. 905-920, vol. 25.

Magni et al., "Model Predictive Control of Type 1 Diabetes: An *In Silico* Trial," *Journal of Diabetes Science and Technology*, 2007, pp. 804-812, vol. 1, No. 6.

Pedrycz et al., *Fuzzy Systems Engineering Towards Human-Centric Computing*, 2007, pp. 27-44, 67-100, & 276-334, John Wiley & Sons, Inc.

Sivanandam et al., "*Introduction to Fuzzy Logic Using MATLAB*," 2007, pp. 1-155, Verlag Berlin Heidelberg, Springer.

Sparacino et al., "Glucose Concentration Can Be Predicted Ahead in Time from Continuous Glucose Monitoring Sensor Time-Series," *IEEE Tranactions on Biomedical Engineering*, May 2007, pp. 931-937, vol. 54, No. 5.

Magni et al., "Evaluating the Efficacy of Closed-Loop Glucose Regulation via Control-Variability Grid Analysis," *Journal of Diabetes Science and Technology*, Jul. 2008, pp. 630-635, vol. 2, No. 4.

"Standards of Medical Care in Diabetes—2009," Diabetes Care, Jan. 2009, vol. 32, Supplement 1, S13-S61, American Diabetes Association.

Atlas et al., "MD-Logic Artificial Pancreas System: A Pilot Study in Adults with Type 1 Diabetes," Diabetes Care, May 2010, pp. 1072-1076, vol. 33, No. 5.

Miller et al., "Automatic Learning Algorithm for the MD-Logic Artificial Pancreas System," Diabetes Technology & Therapeutics, 2011, pp. 1-8, vol. 13, No. 10.

Grant, "A New Approach to Diabetic Control: Fuzzy Logic and Insulin Pump Technology," Medical Engineering and Physics, 2007, pp. 824-827, vol. 29.

Ibbini, "A PI-Fuzzy Logic Controller for the Regulation of Blood Glucose Level in Diabetic Patients," Journal of Medical Engineering & Technology, Mar./Apr. 2006, pp. 83-92, vol. 30, No. 2.

Dassau et al., "In Silico Evaluation Platform for Artificial Pancreatic β-Cell Development—A Dynamic Simulator for Closed-Loop Control with Hardware-in-the-Loop," Diabetes Technology & Therapeutics, 2009, pp. 187-194, vol. 11, No. 3.

Dassau et al., "Modular Artificial β-Cell System: A Prototype for Clinical Research," Journal of Diabetes Science and Technology, Sep. 2008, pp. 863-872, vol. 2, No. 5.

Weinzimer et al., "Fully Automated Closed-Loop Insulin Delivery Versus Semi-Automated Hybrid Control in Pediatric Patients with Type 1 Diabetes Using an Artificial Pancreas," Diabetes Care, Published online Feb. 5, 2008, pp. 1-14, vol. 31. American Diabetes Association.

Clarke et al., "Closed-Loop Artificial Pancreas Using Subcutaneous Glucose Sensing and Insulin Delivery and a Model Predictive Control Algorithm: The Virginia Experience," Journal of Diabetes Science and Technology, Sep. 2009, pp. 1031-1038, vol. 3, No. 5.

Bruttomesso et al., "Closed-Loop Artificial Pancreas Using Subcutaneous Glucose Sensing and Insulin Delivery and a Model Predictive Control Algorithm: Preliminary Studies in Padova and Montpellier," Journal of Diabetes Science and Technology, Sep. 2009, pp. 1014-1021, vol. 3, No. 5.

Hovorka et al., "Manual Closed-Loop Insulin Delivery in Children and Adolescents with Type 1 Diabetes: A Phase 2 Randomised Crossover Trial," www.thelancet.com, Published online Feb. 5, 2010, pp. 1-9, vol. 375.

Dassau et al., "Closing the Loop," The International Journal of Clinical Practice, 2010, pp. 20-25, vol. 64. (Suppl. 166).

Dassau et al., "Closing the Loop," The International Journal of Clinical Practice, 2011, pp. 20-25, vol. 65. (Suppl. 170).

Kovatchev et al., "In Silico Preclinical Trials: A Proof of Concept in Closed-Loop Control of Type 1 Diabetes," Journal of Diabetes Science and Technology, Jan. 2009, pp. 44-55, vol. 3, No. 1.

Patek et al., "In Silico Preclinical Trials: Methodology and Engineering Guide to Closed-Loop Control in Type 1 Diabetes Mellitus," Journal of Diabetes Science and Technology, Mar. 2009, pp. 269-282, vol. 3, No. 2.

Wang et al., "Automatic Bolus and Adaptive Basal Algorithm for the Artificial Pancreatic β-Cell," Diabetes Technology & Therapeutics, 2010, pp. 879-887, vol. 12, No. 11.

Lee et al., "A Closed-Loop Arificial Pancreas Using Model Predictive Control and a Sliding Meal Size Esitmator," Journal of Diabetes Science and Technology, Sep. 2009, pp. 1082-1090, vol. 3, No. 5.

Magni et al., "Run-to-Run Tuning of Model Predictive Control for Type 1 Diabetes Subjects: In Silico Trial," Journal of Diabetes Science and Technology, Sep. 2009, pp. 1091-1098, vol. 3, No. 5.

Wang et al., "Closed-Loop Control of Artificial Pancreatic β-Cell in Type 1 Diabetes Mellitus Using Model Predictive Iterative Learning Control," IEEE Transactions on Biomedical Engineering, 2010, pp. 211-219, vol. 57, No. 2.

El-Katib et al., "A Bihormonal Closed-Loop Artificial Pancreas for Type 1 Diabetes," Science Translational Medicine, Apr. 14, 2010, pp. 1-12, vol. 2, No. 27.

Cameron et al., "A Closed-Loop Artificial Pancreas Based on Risk Management," Journal of Diabetes Science and Technology, Mar. 2011, pp. 368-379, vol. 5, No. 2.

Percival et al., "Development of a Multi-Parametric Model Predictive Control Algorithm for Insulin Delivery in Type 1 Diabetes Mellitus Using Clinical Parameters," Journal of Process Control, 2011, pp. 391-404, vol. 21, No. 3.

(56) References Cited

OTHER PUBLICATIONS

Grosman et al., "Zone Model Predictive Control: A Strategy to Minimize Hyper- and Hypoglycemia Events," Journal of Diabetes Science and Technology, Jul. 2010, pp. 961-975, vol. 4, No. 4.

Castle et al., "Novel Use of Glucagon in a Closed-Loop System for Prevention of Hypoglycemia in Type 1 Diabetes," Diabetes Care, Published online Mar. 23, 2010, pp. 1282-1287, vol. 33, No. 6.

Erdin et al., "Further Development of Artificial Pancreas: Blocked by Patents?," Journal of Diabetes Science and Tehnology, Nov. 2008, pp. 971-976, vol. 2, No. 6.

Japanese Office Action dated May 19, 2014.

Ibbini et al., "A fuzzy logic based closed-loop control system for blood glucose level regulation in diabetics", Journal of Medical Engineering & Technology, vol. 29, No. 2, Mar./Apr. 2005, pp. 64-69.

Atlas et al., Appendix to "MD-logic artificial pancreas system: a pilot study in adults with type 1 diabetes", Diabetes Care 2010; 33:1072-1076.

\* cited by examiner

MONITORING DEVICE FOR MANAGEMENT OF INSULIN DELIVERY

This is a Continuation-in-Part of Application No. PCT/IL2010/000686 filed Aug. 24, 2010, which claims the benefit of U.S. Provisional Applications No. 61/247,017 filed Sep. 30, 2009 and 61/300,874 filed Feb. 3, 2010. The disclosure of the prior applications is hereby incorporated by reference herein in its entirety.

FIELD OF THE INVENTION

This invention is generally in the field of medical application and relates to a method and system for insulin delivery management.

REFERENCES

The following references are considered to be pertinent for the purpose of understanding the background of the present invention:

1. Steil G, Panteleon A, Rebrin K. Closed-loop insulin delivery—the path to physiological glucose control. Adv Drug Deliv Rev 2004; 56:125-144
2. Parker R, Doyle Fr, Peppas N. A model-based algorithm for blood glucose control in type I diabetic patients. IEEE Trans Biomed Eng 1999; 46:148-157
3. Hovorka R, Chassin L, Wilinska M, Canonico V, Akwi J, Federici M, Massi-Benedetti M, Hutzli I, Zaugg C, Kaufmann H, Both M, Vering T, Schaller H, Schaupp L, Bodenlenz M, Pieber T. Closing the loop: the adicol experience. Diabetes Technol Ther 2004; 6:307-318
4. Hovorka R, Canonico V, Chassin L, Haueter U, Massi-Benedetti M, Orsini Federici M, Pieber T, Schaller H, Schaupp L, Vering T, Wilinska M. Nonlinear model predictive control of glucose concentration in subjects with type 1 diabetes. Physiol Meas 2004; 25:905-920
5. Magni L, Raimondo D, Bossi L, Dalla Man C, De Nicolao G, Kovatchev B, Cobelli C. Model Predictive Control of Type 1 Diabetes: An In Silico Trai. J Diabetes Sei Technol 2007; 1:804-812
6. Pedrycz W, Gomide F. Fuzzy Systems Engineering Towards Human-Centeric Computing. Hoboken, N.J., John Wiley & Sons, Inc., 2007
7. Sincanandam S N, Sumathi S, Deepa S N. Introduction to Fuzzy Logic using MATLAB. Verlag Berlin Heidelberg, Springer, 2007
8. Sparacino G, Zanderigo F, Corazza S, Maran A, Facchinetti A, Cobelli C. Glucose concentration can be predicted ahead in time from continuous glucose monitoring sensor time-series. IEEE Trans Biomed Eng 2007; 54:931-937
9. Magni L, Raimondo D, Dalla Man C, Breton M, Patek S, De Nicolao G, Cobelli C, Kovatchev B. Evaluating the Efficacy of Closed-Loop Glucose Regulation via Control-Variability Grid Analysis. J Diabetes Sci Technol 2008; 2:630-635
10. Standards of medical care in diabetes—2009. Diabetes Care 2009; 32 Suppl 1:S13-61

BACKGROUND OF THE INVENTION

Type 1 diabetes is a chronic, life-threatening disease that is caused by failure of the pancreas to deliver the hormone insulin, which is otherwise made and secreted by the beta cells of the pancreatic islets of Langerhans. With the resulting absence of endogenous insulin, people with type 1 diabetes cannot regulate their blood glucose to euglycemic range without exogenous insulin administration. Therefore, it is necessary for people with type 1 diabetes to monitor their blood glucose and administer exogenous insulin several times a day in a relentless effort to maintain their blood glucose near euglycemic range.

The existing blood glucose management devices assist a diabetic patient in managing their blood glucose levels during everyday routine. Some of these devices are insulin pumps that provide continuous delivery of insulin throughout the day. Others are, for example: glucose monitoring devices which measure blood glucose levels along a certain time line i.e. to obtain blood glucose reading; and Artificial Pancreas (AP) systems which automatically modulate insulin delivery (optionally other hormones) according to measured glucose levels.

Insulin pump allows the physician to preset the pump settings to many different basal rates to allow for variation in the patient's lifestyle. In addition, the physician can predetermine the insulin bolus delivery (large dose of insulin) to cover the excess demands of carbohydrate ingestion or to correct high blood glucose levels. These pump settings include: bloods glucose target levels, insulin basal rate; carbohydrate ratio (CR) or factor; correction factor (CF) and constant insulin activity function.

Normally, the physician receives from the patient personalized information which includes the glucose past trace (measured by glucometer in discrete points or using continuous glucose sensor), the insulin that was previously delivered (the detailed log of how many insulin was delivered—in either basal or bolus—over time), and the detailed log of the amount and time of all meals and physical activity of the diabetic patients. The physician thus needs to conduct a retrospective analysis (i.e., look at the log data during the clinical visit) and determine the insulin pump settings based on this information.

Various techniques have been developed aimed at facilitating the operation of the insulin delivery pump device. Such techniques are disclosed for example in the following patent publications:

US Publication No. 2008/0228056 discloses an apparatus comprising a user interface configured to generate an electrical signal to start a basal insulin rate test when prompted by a user, an input configured to receive sampled blood glucose data of a patient that is obtained during a specified time duration, including a time duration during delivery of insulin according to a specified basal insulin rate pattern, and a controller communicatively coupled to the input and the user interface. The controller includes an insulin calculation module.

U.S. Pat. No. 7,751,907 discloses an apparatus comprising a controller; the controller includes an input/output (I/O) module and a rule module; the I/O module is configured to present a question for a patient when communicatively coupled to a user interface and receive patient information in response to the question via the user interface; the rule module is configured to apply a rule to the patient information and generate a suggested insulin pump setting from application of the rule.

US Publication No. 2008/0206799 discloses an apparatus comprising a user interface configured to generate an electrical signal to begin a carbohydrate ratio test when prompted by a user, an input configured to receive sampled blood glucose data of a patient that is obtained during specified time duration, and a controller in electrical communication with the input and the user interface. The controller includes a carbohydrate ratio suggestion module.

U.S. Pat. No. 7,734,323 discloses an apparatus comprising a user interface configured to generate an electrical signal to begin determination of an effective correction factor when prompted by a user, an input configured to receive sampled blood glucose data of a patient that is obtained during a specified time duration, and a controller in electrical communication with the input and the user interface. The controller includes a correction factor suggestion module.

On the other side, the artificial pancreas systems are usually based either on traditional linear control theory or rely on mathematical models of glucose-insulin dynamics. The most common techniques are based on proportional-integral-derivative control (PID) [1] and model predictive control (MPC) [2-5]. However, the nonlinearity, complexity and uncertainty of the biological system along with the inherited delay and deviation of the measuring devices, makes difficult to define a model and correctly evaluate the physiological behavior of the individual patient [1-3, 5]. In addition, because most of the control algorithms are not amenable to multiple inputs and multiple outputs, the measured blood glucose level is generally, the only input implemented, and insulin delivery is the only implemented output.

The PID control algorithm produces an insulin profile similar to the secretion profile done by the beta cells extrapolated by three components [1]. Some controllers include a subset of components, for example, a proportional-derivative (PD) controller includes the proportional and derivative components to improve robustness. Both PID and PD use the measured blood glucose (BG) level as the only input and ignore other parameters, such as previous administered insulin doses. The MPC is based on mathematical model and equations which describes the glucose level response to different insulin doses and carbohydrate consumption. As the response to different insulin treatment is implied by the set of equations, an optimal treatment may be found and applied accordingly. The mathematical model is subject specific, and depends upon system identification phase to estimate the required parameters [3]. The main drawback of MPC in relation to glucose control is the need of a good crisp mathematical model and a good method to estimate its parameters in order to describe the physiological behavior of the patient. However, due to the complexity of biological systems, these models are subject to extreme uncertainties, which make it very hard to evaluate and define the model properly. Most of the attempts in the past to develop Subcutaneous (S.C.) closed loop system used linear control methodology to control the non-linear biological system [2, 5] and disregarded the uncertainty of the biological system and the measuring devices. In addition, it is quite difficult to implement multiple inputs and multiple outputs using these methods.

GENERAL DESCRIPTION

There is a need in the art for a novel approach in management of the insulin delivery to patients. Such need is associated with the following.

Conventional insulin pumps initially require a physician to arrive to the required global pump settings and/or "request" a response from the patient to perform a test for the appropriateness of insulin pump settings (previously set by a physician). This, however, requires higher degree of expertise from the physician and also is based on an assumption that the patient responds correctly to the requests. Such global pump settings remain constant during operation of the insulin pump until such time that the physician or treated patient manually resets them. Insulin pump settings generated based on such conventional approach would thus unavoidably be too sensitive to the cooperation with the patient.

The present invention solves the above problems by providing according to one broad aspect a novel technique for accurate and reliable tailor made insulin pump settings derived from raw log data accumulating for example in conventional blood glucose monitoring device(s). The present invention therefore provides unsupervised determination of global insulin pump settings, e.g. even without human interpretation or assumptions as to the nature in which data was obtained. The technique of the present invention of such unsupervised determination of insulin pump settings from received data is actually absolutely independent from the need of cooperative participation on the part of the diabetic patient.

In contrast to standardized procedure for testing, which require active participation or cooperation of the part of the diabetic patient and/or a physician for arriving to accurate and accountable pump settings, the monitoring technique of the present invention conducts a retrospective analysis of the log/raw data, isolates informative data from raw residual data, and applies unsupervised learning procedures to arrive to the optimal global insulin pump settings. The technique of the present invention thus provides the capability to extract informative data from the raw data, which according to the known techniques is ignored or is exclusively subject to human expert analysis. It should be understood that retrospective analysis utilized in the invention is aimed at calculating global insulin pump settings extracted from historical measured data collected during a certain time interval of several days (at least two days) which forms the raw log data input to the unsupervised data processor. The minimal time interval for the purposes of the invention, i.e. for retrospective analysis, is actually defined by the collection of various types of information (as will be described further below) and the ability of the system (data processor) of identifying different information pieces. The inventors have found that, practically, a two-day data record is sufficient for the calculation of the pump settings. By settings the lower bound of 2 days for the time window for the unsupervised retrospective analysis, the present invention utilizes accumulation of substantial raw log data of the treated patient, however, accumulation of more information is preferred to permit analysis of plethora of data sections of patient information. The historical measured data comprises a plurality of data pieces which according to the invention is appropriately identified, sectioned, isolated and retrospectively analyzed to calculate global insulin pump settings from the historical performance in these data sections. It should also be understood that the invention provides for dealing with the raw data while enabling calculate global insulin pump settings, namely pump settings which are optimal and which should be maintained.

According to some embodiments of the present invention, the above monitoring system further includes a processing unit having additional components/modules (software and/or hardware) for additional processing of other relevant data. The processing unit receives the output of the unsupervised controller, and input parameters corresponding to the measured data, the first processed data and a reference data including said individualized patient's profile related data, individualized patient's treatment history related data. The processing unit is configured and operable for generating a treatment recommendation accordingly. The treatment recommendation may be either sent automatically to the insulin pump or may be presented to an authorized person (e.g. a physician or the patient) through a user interface for choosing whether to apply the treatment recommendation or not.

According to a broad aspect of the present invention, there is provided a monitoring system for use with diabetic treatment management, the monitoring system comprising:

a communication interface configured and operable to permit access to stored raw log data obtained over a certain time and being time spaced data points of glucose measurements, meals consumed and insulin delivery;

a control unit comprising an unsupervised learning controller configured and operable to receive and process said raw log data, to determine an informative data piece from residual log data portion of said raw log data and select said informative data piece for retrospective analysis to calculate individualized patient's profile related data comprising at least one of global insulin pump settings of basal rate (or basal plan), correction factor (CF), carbohydrate ratio (CR) and insulin activity curve (AIF).

In some embodiments, the raw log data is acquired in accordance with a preprogrammed sampling pattern. The unsupervised learning controller is configured and operable determine each of said parameters from a part of said informative data piece corresponding to a selected time slot of said certain time. Therefore, said informative data piece relating insulin pump settings are identified in the corresponding time slots.

The unsupervised learning controller is configured and operable for analyzing said informative data piece and selects the appropriate time slot for calculation of each of said parameters; the global insulin pump parameters being of basal rate (or basal plan), correction factor (CF), carbohydrate ratio (CR) and insulin activity curve parameters.

In some embodiments, the received raw log data corresponds to a memory image at the access time irrespective of any user interaction.

In another aspect, the present invention relates to a monitoring system for use with diabetic treatment management, the monitoring system comprising:

a communication interface configured and operable to permit access to stored data being time spaced data points of glucose measurements, meals consumed and insulin delivery;

a control unit comprising a data processor utility for providing retrospective analysis of said data and determining at least one global insulin pump setting of basal rate (or basal plan), correction factor (CF), carbohydrate ratio (CR) and insulin activity curve parameters, wherein said processor utility is operable to determine each of said parameters by processing a data piece of said received data corresponding to a selected time slot of said certain period of time.

In some embodiments, the processor utility is configured and operable for analyzing the received data and selects the time slot in said certain period of time for determination of each of said parameters.

In some embodiments, the control unit comprises a controller associated with said communication interface and preprogrammed for receiving said data according to a predetermined sampling time pattern.

The received stored data can be that of a memory image at the access time irrespective of any user interaction.

The system can comprise a memory module configured and operable to maintain the stored data.

The analyzing can include sectioning the stored data; thereby to obtain stored data within a predetermined time window. Where the predetermined time window is a Basal data Section (BaS) the calculated insulin pump settings being selected is basal rate or basal plan. Where said predetermined time window is a Meals data. Section (MS) the calculated insulin pump settings being selected from being Active Insulin Function (AIF), correction factor (CF) or carbohydrate ratio (CR). In case, the predetermined time window is a Bolus data Section (BS) the calculated insulin pump settings being selected from correction factor (CF) or Active Insulin Function (AIF). The stored data can be obtained from a remote controller such as for example from a controller or module of an insulin pump delivery device. In some embodiments, the stored data is accessible via random asynchronous operation which is independent of a user operation. In some embodiments, the stored data is a memory image of a remote controller independently accumulating the raw log data input. The remote controller(s) can independently accumulate said information which records the everyday routine of the treated patient. The information indicative glucose sensor readings, insulin delivery and meals recordation can be a file being obtained from the remote controller independently accumulating said information.

The file can be downloaded from a network and stored in the memory module.

In another aspect, the present invention relates to a method for use in determination of insulin pump settings, the method comprising: performing unsupervised learning of the insulin pump settings, said unsupervised learning comprising:

obtaining raw log data input accumulated on one or more glucose monitoring units recording glucose levels of a single treated patient along a certain time window;

determining informative data piece from raw log data input being sectioned to data sections, the informative data piece being determined from said data section; and calculating insulin pump settings from the informative data piece, wherein said settings include at least one parameter of basal plan, Carbohydrate Ratio (CR), Correction Factor (CF) or Active Insulin Function (AIF).

The sectioning procedure of the raw log data provides predetermined data sections which can be any of Basal Section (Bas), Bolus Section (BS), or Meal Section (MS). The method utilizes aligning procedure to provide plurality of data portions of said raw log data input along a shared time axis.

The method can further include determining a representative data point having both a value of aggregated blood glucose levels and a time stamp; the value of aggregated blood glucose level is thus paired to a selected basal period; the representative data point indicates a basal rate determination for the selected basal period.

In some embodiments, the raw log data input of said Basal Section (Bas) includes a series of basal rates as a function of time. The method can thus include:

determining a time delay characterizing the treated patient at said Basal Section (Bas), said time delay being between a basal treatment rate and changes in the glucose level;

obtaining a plurality of selected basal rates at a delivery time, a respective paired glucose level being at the time delay measured from the delivery time; and determining a resultant basal rate from the plurality of selected basal rates which minimizes a change in the glucose level.

In some embodiments the method comprises determining an Active Insulin Function (AIF) by carrying out the following method:

obtaining a set of glucose measurements and paired time stamps for the raw log data in the time section;

normalizing each glucose measurement of the set thereby obtaining a series of normalized glucose measurements and paired time stamp; and processing said normalized glucose measurements and paired time stamp into a substantially monotonic non-increasing series; thereby obtaining the Active Insulin Function (AIF).

In some embodiments, the method includes determining plurality of glucose level and paired practical carbohydrate ratios for the MS Section; the paired practical carbohydrate ratios being candidate carbohydrate ratios defining a curve. The final carbohydrate ratio (CR) setting is determined from the candidate practical carbohydrate ratios.

In some embodiments, a correction factor (CF) is determined for the meal and is calculated by processing the AIF to estimate the active insulin in the MS Section and a just-in-time carbohydrate ratio (CR).

The correction factor (CF) can be modified in accordance with the following parameters:
    a proportion between a minimum sensor reading during a time window or section, a lowest blood glucose reading recorded outside impending hypoglycaemia and hypoglycaemia time periods; and
    a maximum sensor reading in a time slot prior to obtaining the minimum sensor reading.

In some embodiments, a plurality of candidate correction factors (CF) are determined and the correction factor (CF) setting is determined by a voting procedure performed with those candidate correction factors (CF).

In another aspect, the present invention provides a method for determining an Active Insulin Function (AIF) for use in insulin treatment of a patient, the method comprising:
    obtaining raw log data obtained over a certain time and being indicative of glucose measurements of the patient, the raw log data being sectioned, containing data obtained at a time section;
    obtaining a set of glucose measurements and paired time stamps for the raw log data in the time section;
    normalizing each glucose measurement of the set thereby obtaining a series of normalized glucose measurements and paired time stamp; and
    processing said normalized glucose measurements and paired time stamp into a substantially monotonic non-increasing series; thereby obtaining the Active Insulin Function (AIF).

In another aspect, the present invention provides, a control unit for use with diabetic treatment management, the control unit comprising: a data processor utility configured and operable as an unsupervised learning controller preprogrammed for processing raw log data input obtained over a certain time and being indicative of glucose measurements, meals events and insulin delivery, the processing comprising determining an informative data piece from residual log data portion of said raw log data and selecting said informative data piece for further processing to determine at least one of basal rate (or basal plan), correction factor (CF), carbohydrate ratio (CR) and insulin activity curve parameters, and generating global insulin pump settings.

According to some embodiments of the present invention, the above-described monitoring system further comprises a processing unit comprising: a first processor module and a second processor module. The first processor module is configured for processing measured data indicative of blood glucose level and generating first processed data indicative thereof. The second processor module comprises at least one fuzzy logic module. The fuzzy logic module receives input parameters corresponding to the measured data, the first processed data and a reference data including said individualized patient's profile related data, individualized patient's treatment history related data, processes the received parameters to produce at least one qualitative output parameter indicative of patient's treatment parameters; such that said second processor module determines whether any of the treatment parameters is to be modified and generate corresponding output data which can be supplied directly to the pump and/or presented through a user interface to an authorized person (patient and/or physician) for a decision making and/or recording.

In a variant, input parameters include at least one of the following input parameters: past blood glucose level trend, current blood glucose level, future blood glucose level trend, future blood glucose level.

The at least one fuzzy logic module may be characterized by at least one of the following: (i) it comprises a set of rules associated with contribution factors and at least one fuzzy engine utilizing one or more member functions modeled for translating the input parameters into at least one qualitative output parameter; and (ii) is configured and operable to provide the at least one output parameter comprising data indicative of at least one of bolus glucagon, bolus insulin and basal insulin treatment, said second processor module thereby providing control to range output treatment suggestion based on the output parameter of the fuzzy logic module.

In another variant, said processing unit comprises a third processor module receiving said at least one qualitative output parameter of the fuzzy logic module and said input parameters corresponding to the measured data, the first processed data and the reference data, and processing said at least one output parameter said input parameters to determine whether any of the treatment parameters is to be modified and generate corresponding output data which can be supplied directly to the pump and/or presented through the user interface to an authorized person (patient and/or physician) for a decision making and/or recording, said treatment parameters comprising at least one of dosing of insulin and glucagon to be delivered.

In a further variant, the at least one output parameter of the at least one fuzzy logic module comprises data indicative of at least one of bolus glucagon, bolus insulin and basal insulin treatment, and said second processor module thereby provides control to range output treatment suggestion based on the output parameter of the fuzzy logic module, the third processor receiving the control to range output treatment suggestion, and determining said amount in accordance with at least one of a glucose target of the patient's profile, patient's insulin or glucagon pharmacodynamics, and said measured data.

In a further variant, the processing unit is operable to update and/or calibrate said individualized patient's profile related data during treatment or during monitoring procedure.

Optionally, said individualized patient's profile related data comprises parameters selected from at least one of global pump settings, insulin sensitivity, glucagon sensitivity, basal plan, insulin/glucagon pharmacokinetics associated data, glucose target level or target range level, and insulin/glucagon activity model.

Said individualized patient's treatment history related data may comprise patient's insulin delivery regimen given to the patient at different hours of the day.

According to some embodiments of the present invention, said second processor module comprises a fuzzy logic module operable in response to an event being invoked by a detector module analyzing at least one pattern of glucose levels indicative of at least one event, said event comprising at least one of sleep, meal, exercise and disease event or rest.

Said system may be configured and operable to alternate between at least two fuzzy logic modules, each handling a different event.

In a variant, said second processor module is operable as a meal treatment module and is configured to monitor the blood glucose level.

In another variant, the input parameters further include at least one of the following input parameters: time elapsed between detected special events, blood glucose level with respect to said special event.

Optionally, said measured data is obtained at a certain time, said measured data comprising at least one of current and past glucose levels relative to said certain time.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 21A shows the CGS readings (black line) and the reference measurements (black diamond). FIG. 21B shows the insulin treatment delivered by the monitoring system of the present invention. FIGS. 21C and 21D show results from control performances comparison between home care (circles) and by using the monitoring system of the present invention (rectangular) using the Control Variability Grid Analysis [9] during time period of 24 hours (FIG. 21C) and during night time (FIG. 21D).

DETAILED DESCRIPTION OF EMBODIMENTS

In accordance with the present invention, insulin pump settings are calculated on the basis of raw log data utilizing an unsupervised learning procedure carried out by a controller utility constructed and operable according to the invention. The controller analyses machine readable raw log data without supervision or human assisted analysis as well as without a need for any other pre-processing of said data. The invented technique permits an assignment of set of parameters which defines the patient's insulin pump treatment management and does not require human pre-processing or assistance.

All that is necessary for learning the raw log data is the provision of the raw log data input to the system or device of the present invention in a machine readable format.

The insulin pump settings include a set of parameters which defines the patient's insulin pump treatment management. Conventionally, these parameters are determined at least initially by a trained physician by retroactively manually analyzing past performance of patient's input data in the form of graphs and decision making by the physician based solely on his intuition and experience, being thus substantially subjective decision. Moreover, according to the conventional approach, such set of parameters (insulin pump settings) is tailored specifically for each patient by the physician in accordance with the retrospective analysis.

The insulin pump settings typically include the following:

Basal Plan, which is the constant infusion of insulin as planned for the hours/time of the day. It consists of several "basal rates" (typically in units of insulin per hour) and delivered at different times of the day. An exemplary, non limiting illustration can be understood from Table 1.

TABLE 1

The Basal Plan

| Hour of the day | Basal Rate [u/h] |
|---|---|
| 00:00 | 0.8 |
| 07:00 | 1.5 |
| 20:00 | 1 |

As shown in Table 1, the first column represents the delivery time or the time slot in which insulin is delivered. The second column shows the amount of insulin to be delivered. As the person skilled in the art would understand, plurality of data structures and memory utilities can maintain the basal plan related information. Essentially, the memory items maintaining such information comprise a pair of the following structures in the form of <time stamp, basal rate> or <a period of time/time slot, basal rate>. These pairs of data pieces is also shown and discussed herein.

Figure 1:
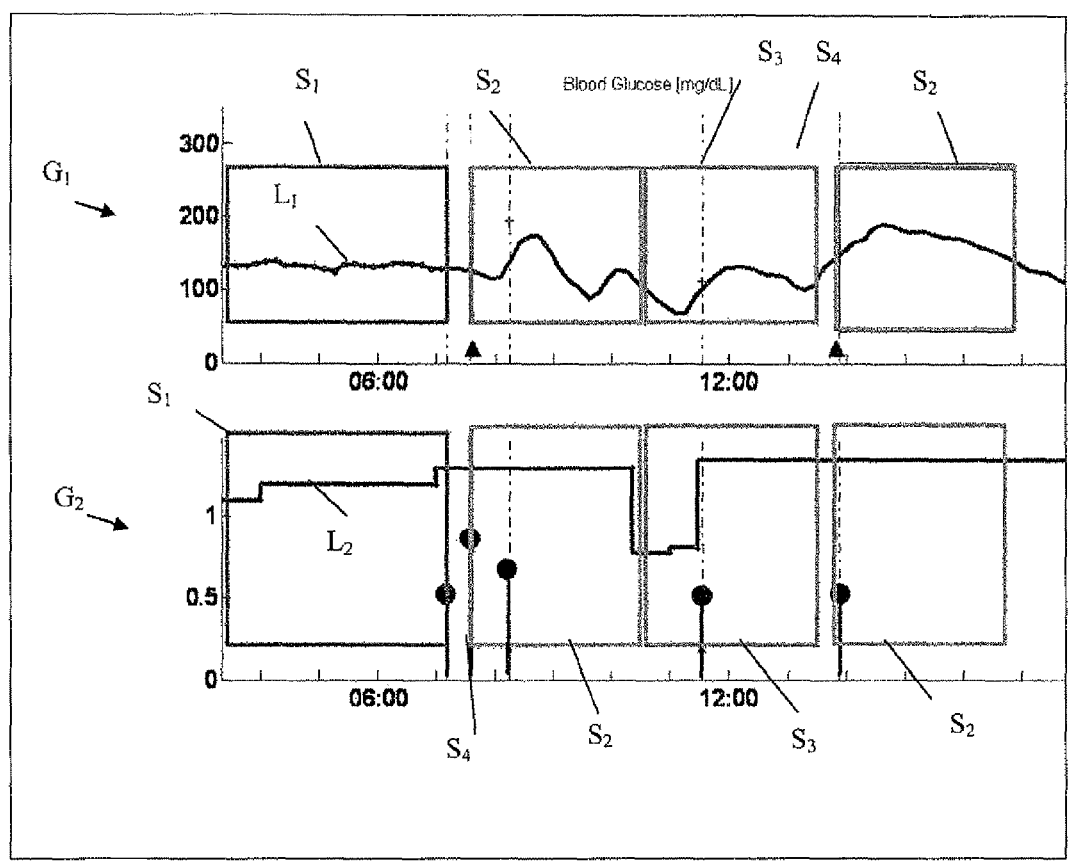
FIG. 1 is an illustration of raw log data used in the present invention, and exemplifies the principles of sectioning of this data into different data sections or data section types. The top graph $G_1$ presents the glucose level $L_1$ where meal events $S_4$ are marked by triangles. The bottom graph $G_2$ presents the insulin treatment, where the horizontal line $L_2$ is the basal rate and the vertical lines with circles are the boluses. The section $S_1$ corresponds to Basal data Section (BaS), section $S_2$ corresponds to Meal data Section MS and section $S_3$ corresponds to Bolus data Sections BS.

In this connection, reference is made to FIG. 1 showing a non-limiting example of blood glucose level measured data (graph $G_1$), and the insulin treatment (graph $G_2$) in which the horizontal line $L_2$ corresponds to the basal rate and the vertical lines with the black circle correspond to the boluses. These graphs will be described more specifically further below. With regard to the basal plan, the horizontal line $L_2$ in graph $G_2$ represents the above-discussed pairs <a period of time/time slot, basal rate>. The graph $G_2$ is illustrating the treatment as changing as a function of time. In FIG. 1, within the time slot from 00:00 to 02:00, 1.1 units/hour are planned to be delivered. The corresponding pair can be, for example, <00:00-02:00, 1.1>. The person skilled in the art would appreciate that there are variety of ways to encode such information and the particular encoding regime can be determined for such purpose.

Carbohydrate Ratio (CR) is a parameter of the insulin pump settings which is used to determine the required insulin bolus to compensate for carbohydrates (CHO) consumed in meals by the patient. CR is typically defined in gram of CHO per units of insulin. For example, the patient would eat a meal with CHO content of 50 grams and his CR is equal to 5 gr/units. In this scenario, the patient would require to receive an insulin bolus of 10 units (also termed as "meal insulin bolus" to emphasize that the bolus is required as a result of the meal).

Correction Factor (CF) is a parameter of the insulin pump settings used to determine or decide the needed insulin bolus to compensate for changes of the blood glucose level from a target blood glucose level. CF is defined in mg/dl per units of insulin. For example, the patient's blood glucose level is 250 mg/dl and the target blood glucose level is 100 mg/dl, in which case the CF is determined by the physician to be 50 mg/dl/units. In this scenario, the patient will require to deliver a correction insulin bolus of 3 units, i.e. in order to correct 150 mg/dl above the target threshold. Another example is when the blood glucose level is below a predefined target or threshold. For example, if the blood glucose level is 65 mg/dl, the patient will calculate a correction bolus of (−0.7) units, i.e. in order to correct 35 mg/dl below the target threshold. The patient can use this result and subtract it from the meal insulin bolus if he wishes to eat. In some scenarios, the meal bolus was originally 10 units, the patient can consider his low blood glucose level and deliver only 9.3 units (10-0.7 units).

The Insulin Activity Function (AIF) is another parameter of the insulin pump settings defining the percentage of insulin that is still active (i.e., Active Insulin, also termed as "AI") at (T) hours after delivery, e.g. typically as a function of time. The expression "still active" means that these units of insulin have an influence on the blood glucose level and insulin still actively participates in glucose regulation from the blood to the cells. The AIF defines the pharmacodynamics behavior of insulin for the patient. According to the conventional insulin delivery management technique, AIF is selected from constant predefined portfolios which were defined on the basis of data which relate to a class of patients and not to a specific patient being treated. The physician chooses from these predefined AIF the specific for use. For example, the following equation sometimes is describing the AIF:

$$AI = 100 - 20t \quad (1)$$

where AI is the percentage of active insulin, and t is the time (e.g. in hours) that passed since delivery of the insulin. For example, employing this function, where an insulin bolus in size of 4 units was delivered at t=0, than at t=1 hour, 80% of this bolus is still active, i.e. 3.6 units; and at t=5 hour, this bolus has no longer active.

It should be noted that some delivery pumps permit for subtracting an amount of active insulin from a calculated insulin bolus.

Blood glucose target level, which is the blood glucose level that the patient is aiming at, while a correction bolus is being determined.

Some insulin pumps have a bolus calculator which allows the patient to insert the CR, CF, AIF and targets to the pump and assists the patient in calculating the required bolus.

In order to optimize and improve the glucose level control of a treated patient, it is essential to appropriately tailor the pump settings, i.e. the blood glucose targets, insulin correction factor, carbohydrate ratio, basal plan and insulin activity function. These tailored pump settings can be further changed from time to time.

In normal practice, the physician receives from the patient (during the visit or over the web) the patient's input which includes the following data:

(a) The glucose trace (e.g. measured by glucometer in discrete points or using continuous glucose sensor). The case may be such that the physician obtains this information as a data record (typically in the form of a graph), e.g. from the memory component of a glucose monitoring unit or glucose management device. This information can be in the format of <time stamp(i), BG(i)>, where BG(i) is the measured blood glucose.

(b) The amount of insulin that has been delivered (e.g. the log of how many insulin units were delivered—in basal or bolus—over time). This information can be in the format of <time stamp(i), BasalRate(i)> and <time stamp(i), Bolus(i)>, where BasalRate(i) is the delivered basal insulin and Bolus(i) is the delivered bolus insulin; and (c) The meal/activity log(the detailed log of the amount and time of meals or activity). This information can be in the format of <time stamp(i), M(i)>, where M(i) is the amount of CHO consumed.

The person skilled in the art would appreciate that other data formats can by employed to represent data item (a), (b) and (c).

The present invention utilizes such data records, being actually raw log data, obtainable from the memory component of the insulin delivery pump or other measurement and/or storage apparatus used to record the data item (a), (b) and (c) and possibly other information during the everyday routine of the treated patient i.e. recordation of every day routine.

Raw log data therefore includes an analog or digital representation of measured signal(s) from the analyte sensor directly related to the measured glucose and data that was recorded by the patient's insulin pump as insulin delivery and meal consumed. For example, the raw data stream is digital data converted from an analog signal representative of the glucose concentration at a point in time, or a digital data representative of meal consumption at a point in time. The terms broadly encompass a plurality of time spaced data points from a substantially continuous analyte sensor (or continuous glucose sensor), each of which comprises individual measurements taken at time intervals ranging from fractions of a second up to, for example, 2, 4, or 10 minutes or longer. The time-spaced data points, in some embodiments, adhere to a preprogrammed sampling pattern.

The raw log data can be obtained or received from stored data (from a memory utility which may be associated with a remote computer system/database or with the measurement device of the patient). The stored data can be thus obtained as a memory image at the access time to the stored data. In this context, a memory image refers to data stored for example in an insulin delivery pump As-Is without further processing. Data collected at the patient's every day routine activity is different from that gathered while intentionally guiding the patient's activity. For the purposes of the invention, the raw log data may be continuously accumulated without any special attention of the monitored patient (other than being connected to the monitoring unit), as well as without any special attention of a clinical personnel. Recording these measurements over time is performed as a part of a monitoring phase, in any known suitable technique, which by itself does not form part of the present invention. The use of such raw log data used in the present invention does not include standardized procedure for testing which requires active participation from the patient or test time lines, i.e. the patient maintains normal every day activity and is not required, for example, to consume or to refrain from consuming any food matter. It is important to note that this raw log data is gathered over a time interval of several days during every day activity of the patient. The present invention provides a novel technique for determining insulin delivery pump settings from said raw log data being recorded during the everyday routine of the patient.

Comparing the above to the conventional approach, it should be understood that the invention eliminates a need for a physician to conduct any retrospective analysis (i.e., look at the data during the clinical visit) and subjectively conclude how to change the global insulin pump settings based on this information. This is advantageous because practically not all physicians have the needed expertise to fulfill this task properly. In addition, for those who have the needed expertise, this task is very time consuming. Sometimes analyzing the data becomes very difficult due to the fact the data has no clear pattern visible/identifiable for the human eye in order to arrive to the conclusion regarding the appropriate insulin pump settings.

Therefore, the present invention addresses the challenge of replacing the trained physician's retrospective analysis of the patient's input by providing an unsupervised system which is capable of properly analyzing the raw log data input. Such unsupervised system of the present invention organizes the data (i.e. isolates the informative essence from the subordinate), learns and determines insulin pump settings in order to optimize glucose level control. The inventors termed this property as "MD-Logic" system. The input to the system may include solely the stored raw log data obtained over a certain time window and being indicative of current insulin pump settings, glucose measurements, meals events and insulin delivery. The raw log data is processed by a control unit comprising an unsupervised learning controller configured and operable to receive and process the raw log data, determine an informative data piece from residual log data portion of said raw log data, and select said informative data piece for further processing aimed at determining at least one of basal rate, correction factor (CF), carbohydrate ratio (CR) and insulin activity curve parameters, and generating an insulin pump settings. The insulin pump settings are global insulin pump settings, i.e. constant settings which are not changed during operation.

Unsupervised learning procedure, in accordance with the embodiment of the present invention, includes the following processes:
  a) Initial data analysis and sectioning;
  b) Learning Basal Plan algorithm;
  c) Learning AIF algorithm;
  d) Learning CR algorithm;
  e) Learning CF algorithm;
  f) Updating the settings of the Settings the Targets.

It should be noted that the present invention is limited neither to the performance of all of the above listed procedures nor to an order in which they are listed above.

In some embodiments, the unsupervised learning controller is configured and operable to perform at least one of the unsupervised learning procedures or methods. The unsupervised learning procedures should be understood as those which determine insulin pump settings from raw log data as defined above without human participation during the raw log data collection and/or during the process performance which arrives to the determination of the insulin pump settings. As indicated above, raw log data is log recordation being performed during regular routine activity of the patient irrespective of any assumed testing or other premeditated assumption relating to the specific patient or physician (i.e. a user independent procedure/method).

The following is the more specific description of the examples of the invention for implementing each of the above procedures:

Initial Data Analysis and Sectioning

Raw log data contains data, for example, from one or more drug delivery devices (or monitoring device(s) recording the required measurements), and/or glucose measurement device (s) and/or the carbohydrate consumed by the patient. These data pieces may be collected for several days while the patient is maintaining his/her daily routine and insulin treatment.

The inventors have found that insulin pump settings' learning may be achieved by focusing on certain time slots in which the raw log data has been accumulated. In this respect, a time slot is a time window having a starting point and an end point. Raw log data being accumulated in a certain time slot refers to raw log data having a timestamp accrued in said time window, i.e. between the start and end points. The inventors have found that different insulin pump settings' parameters should be acquired at different time slots. In some embodiments, therefore, different components/parameters of the insulin pump settings require pre-processing of the entire raw log data to identify its matching/paired time slot. In some embodiments the data sections adhere to a preprogrammed sampling pattern. The inventors have found that the data sections and their associated or paired pump settings' parameters can be described as follows:

A) Basal data Sections (BaS)

Identification of the matching/paired time slot for the basal plan determination is based on the understanding that changes in the basal plan are particularly informative where boluses or meals do not affect the glucose measurements. Therefore, the BaS sections include data points that include only sensor log measurement and basal rates delivered, and are distant in time from the effect of insulin bolus or meals. A time window or zone including data indicative of the effect of meal and/or bolus injection can be determined automatically. The BaS sections can be defined as those which do not include the effect window of either meal or bolus. For example, the BaS section can be determined as three hours time slot following a bolus delivery or a meal. Optionally, the effect zone can be set (automatically or manually) to about 2, 3.5, 4, 6 or 8 hours following the bolus delivery or the meal, or even more. In some embodiments, BaS time slot starts about three hours after the last recorded bolus or meal and terminates at the occurrence of the next meal or bolus.

B) Meals data Sections (MS)

MS sections contain data points such that their time stamps are at most about 3 hours ahead of a meal data point. Each of MS sections can contain raw log data indicative of one or more meals, insulin boluses, basal rate and glucose measured levels.

C) Bolus data Sections (BS)

These sections contain data points that match the following criteria:

Starting point of BS section that can be determined as one of the following:
1) The end point of the MS section or BaS section; or
2) Insulin bolus data point which is not included in the MS section and which has its time stamp at most 3 hours ahead of the previous insulin bolus.

The ending point of this section could be one of the following (in all the below options, the time stamp of each option is always ahead of the above starting point):
(1) The beginning of the MS section or BaS section; or
(2) The latest option (in time scale) among the following:
  (a) 3 hours ahead of insulin bolus data point without any bolus insulin in that time frame of 3 hours; or
  (b) 3 hours after the starting point without any bolus insulin in that time frame of 3 hours.
(3) In any case, this section length will be not shorter than about 1 hour.

Turning back to FIG. 1, it provides examples for the different section types which were stated above and determined in accordance with the above sectioning procedures, i.e. Basal data Sections (BaS), Meals data Sections (MS) and Bolus data Sections (BS). The top graph $G_1$ in FIG. 1 presents the glucose level where meal events $S_4$ are marked using a black triangle. The bottom graph $G_2$ presents the insulin treatment, where the horizontal line $L_2$ is the basal rate and the vertical lines with the black circle is the boluses. The section $S_1$ corresponds to BaS, namely this section $S_1$ is used by the learning procedure to produce or determine the basal rate parameters. Section $S_2$ corresponds to MS, i.e. is used by the learning procedure to produce or determine the CR, AIF or CF parameters, as described below, and section $S_3$ corresponds to BS, namely is used by the learning procedure to produce or determine the AIF or CF parameters, as described below.

In some embodiments, the present invention relates to a sectioning module; the sectioning module is configured and operable to analyze raw log data being provided as input; the input is processed to produce output signal indicative of at least one data section of Basal Data Section (BaS), Meal data Section (MS) and Bolus data section (BS).

By way of non-limiting example, the BaS can be provided as input to a basal plan module to be processed and calculate the appropriate basal plan. The BS can be provided as input to any of the correction factor module and/or the AIF module. The MS can be provided as input to any of the carbohydrate ratio module, correction factor module and/or the AIF module.

Learning Insulin Pump Settings

Figure 10:
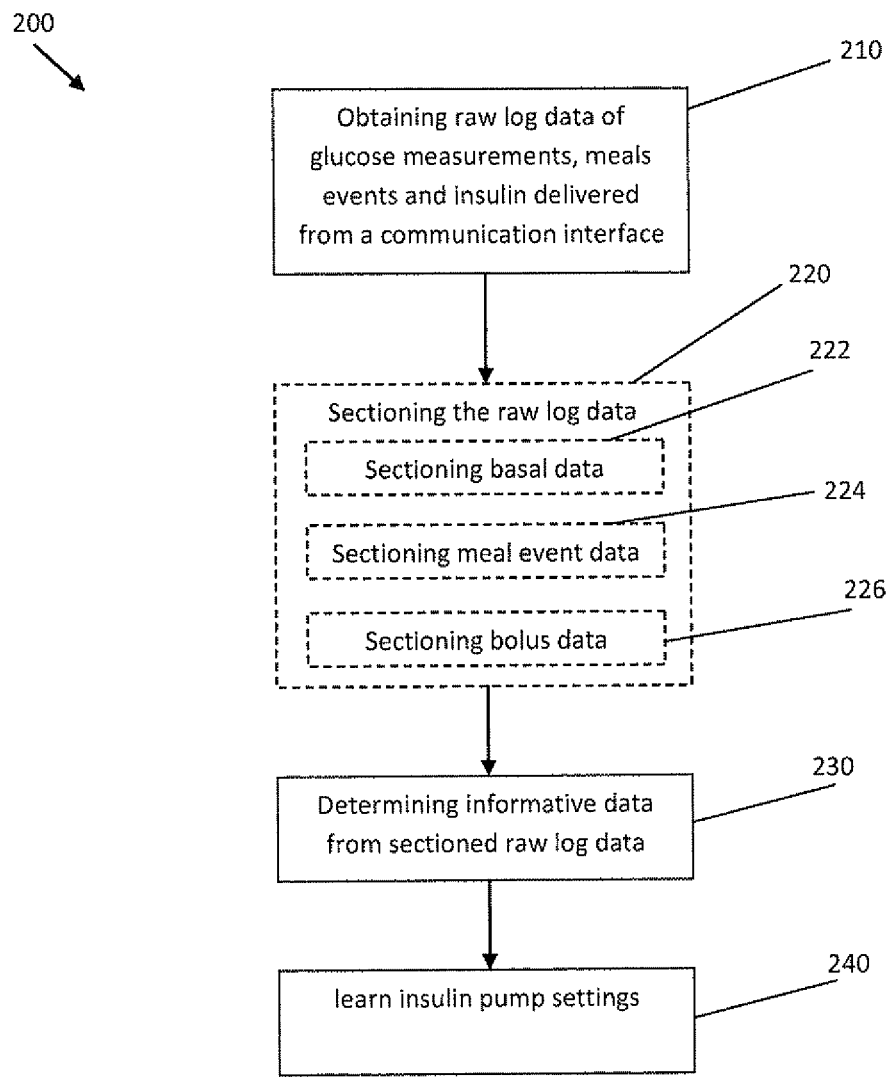
FIG. 10 is a flow chart illustrating a method for unsupervised determining insulin pump settings.

FIG. 10 is flow diagram 200 exemplifying the major procedures performed by the monitoring system of the invention (for example by system 100, discussed below) to learn and determine global insulin pump settings. The insulin pump settings can include at least one of basal plan, CR, CF and AIF. Specific techniques to determine basal plan, CR, CF or AIF is provided herein below.

The method comprises obtaining raw log data 210, as input data to the controller/processor of the invention. The raw log data input is machine readable data from which analysis is derived.

Learning insulin pump settings includes determining informative data piece(s) 230 from sectioned raw log data 210. Informative data piece includes those data items in the raw log data which comprise a reliable input for further learning techniques of insulin pump settings. In some embodiment, the informative data piece comprises glucose patterns or traces which can be relied upon in analysis. It can also include data being derived or enhanced from the raw log data. The informative data piece being identified can thereafter be used for further unsupervised learning (or determining) of the insulin pump settings 240. The insulin pump settings 240 can be any of carbohydrate ratio, basal plan and correction factor.

Therefore, method 200 permits unsupervised determination of insulin pump settings on the basis of raw data and without necessitating cooperation on the part of the user or a trained physician.

All that is necessary for the unsupervised learning and pump settings determination is the provision that the raw log data input has a machine readable format.

In some embodiments, the method 200 includes specific sectioning of the raw log data 220. The inventors found that each of the parameters or settings of the insulin pump can utilize different data portions of the raw log data input. In some embodiments, the raw log data is processed by sectioned portions which can be used for the determination of basal plan 222. The procedure to isolate or section the raw log data input to BaS section (i.e. basal related information) were described above.

In some embodiments, the method 200 includes sectioning the raw log data input to MS section 224 i.e. meal events related data. In some embodiments, the method 200 includes sectioning the raw log data input to BS section 226 i.e. bolus related data.

In addition, the inventors have found that accuracy of the insulin pump settings being determined can be enhanced by aligning the raw data and optionally aggregating the aligned data input. Such alignment procedure enhances and/or isolates informative data pieces from more varied input data. Thus, for example, raw log data input being collected "on the fly" can be used instead of for example, standardized test performed at predetermined conditions by the treated patient.

The sectioning techniques further permit data analysis of plurality of data sections, the plurality of data sections is utilized for determination of a specific insulin pump parameter, such as the CR, CF or the basal plan. Initial data analysis and sectioning was already described above.

The plurality of data sections is analyzed together to enhance those informative (and/or recurrent) data pieces implicit in those raw data of those sections. BaS sections are used for the analysis of basal rate parameters, BS sections are used for the analysis of CF or AIF parameters and MS sections are used for the analysis of CR, AIF or CF parameters.

Learning Basal Plan

Insulin that is delivered through the basal plan typically affects the dynamics of the glucose levels, but this effect is subtle compared to the observed effect of carbohydrates consumption (meals) and given insulin (boluses). Therefore, the raw log data of measured glucose levels can be "cleaned" by using informative segments or portions of the raw log data and selectively not using data segments of glucose levels that might be affected by meals or bolus insulin (MS or BS section). In some embodiments, the learning procedures of the present invention analyze the "cleaned" data or the informative segment of the raw log data. In some embodiments, the "cleaned" data is the raw log data of the BaS section. In other embodiments, where for example, such clean data is not available, and therefore other data segments are used to analyze insulin pump settings for basal insulin (elaborated below).

The basal plan can be represented as a series of individualized basal treatment rates as a function of time. The analysis of such data is performed separately for predefined periods of the day (i.e. Basal Periods). By way of an example, raw log data is separately analyzed for basal period 0000 h-0400 h separately from the other data.

Figure 11:
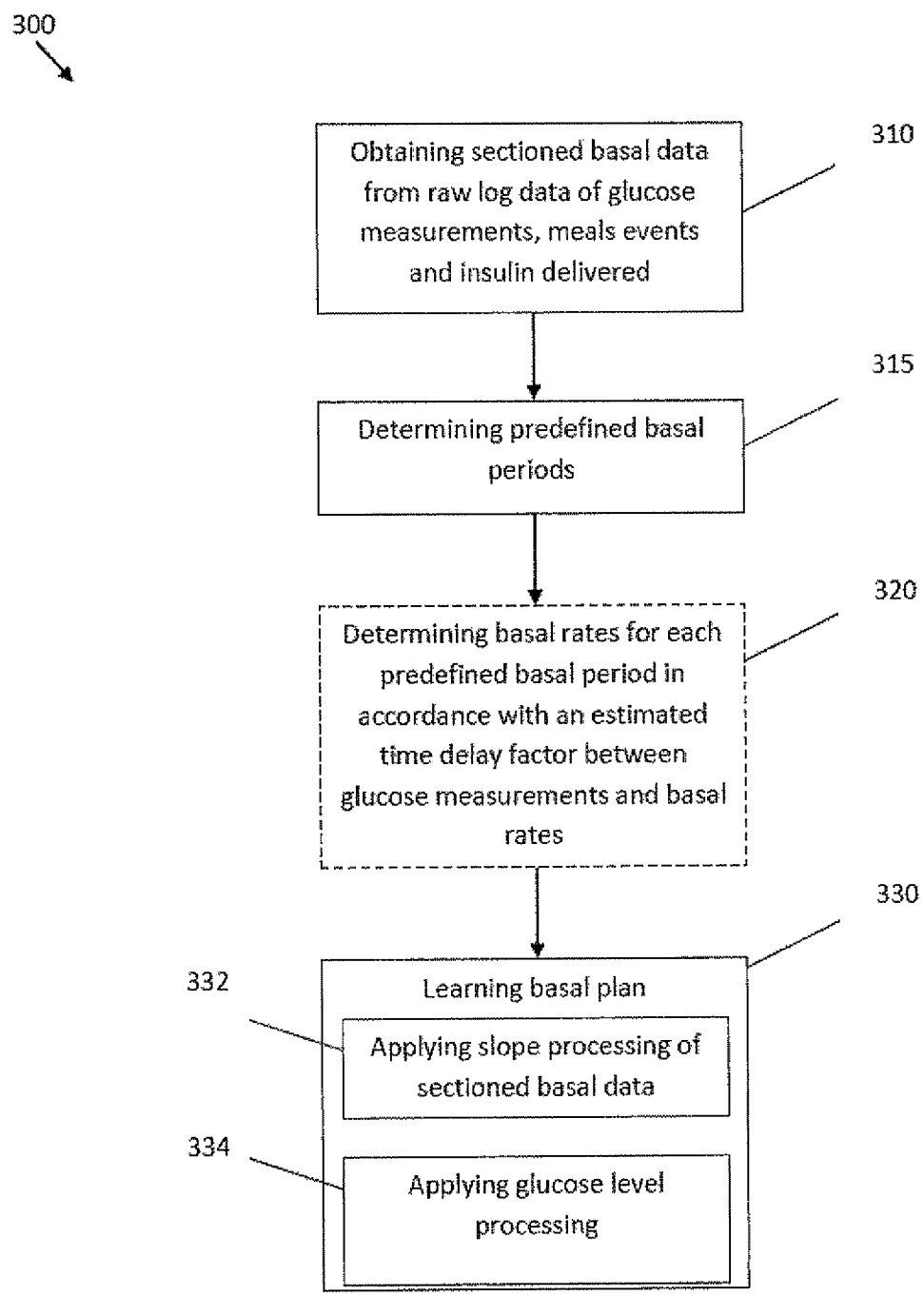
FIG. 11 is a flow chart illustrating a method for unsupervised determination of the basal plan.

FIG. 11 is a flow chart 300 describing a method for unsupervised learning of the basal plan in accordance with an embodiment of the present invention. The unsupervised learning method 300 includes obtaining sectioned basal data from the raw log data of glucose measurements, meals events and insulin delivered (step 310). The sectioning procedures were described above and are applicable in the present context as well. In some embodiments, the raw log data includes glucose measurements and insulin delivered, i.e. meal event is not mandatory in the embodiment.

The method 300 also includes determining predefined basal periods optionally, as time slots or periods along a day 315. The raw data inputs of those periods being collected in plurality of calendar days are aligned, as will be further elaborated below, to extract informative data specific for that/those period(s) of the day. Prior to analysis, the raw log data input can optionally be shifted with a time delay which can be calculated as described below.

In some embodiments, the method 300 performs a procedure 320 to determine the time delay characterizing a treated patient from insulin delivery and blood glucose changes (calculation of the time delay A was described herein). Following the determination of the time delay, determining basal rates for each predefined basal period in accordance with an estimated time delay factor between glucose measurements and basal rates can be performed. For example, in response to a time delay $A_0$ the raw log data input can be shifted accordingly at about the time delay $A_0$ to properly compensate for said delay characterizing the treated patient.

Following the obtaining of raw log data input, the method includes a learning basal plan procedure 330, Slope related algorithm 332, designed to determine whether the patient is in need for change of the basal plan, can be performed. This procedure is based on the value of dG and the glucose level at the end of each "clean data" section (e.g. the BaS section). Alternatively or in combination with the procedure of slope related algorithm 332, the glucose level algorithm 334 utilizing raw low data can be performed. The raw log data input needs not be cleaned or preprocessed, i.e. general log data of glucose level and basal rates are used.

In some embodiments, the learning procedure for determining the basal plan can be initiated by determining or calculating the current characterizing time delay of the specific patient being monitored/measured from occurrence of changes (or fluctuations) in blood glucose measurements and the basal rates delivered.

Glucose sensor readings (G(t) and the basal rates (B(t)) are obtained from BaS Section A change of glucose levels between two data points is thus determined, i.e., the difference between the glucose levels at the end of the section to the beginning of the section, and can be denoted by dG. A change of glucose levels in time (t) can be defined as follows: DG(t)=dG/dt.

Variable (A) denotes the time delay between the basal rates and the measured glucose level. Basal rates at B(t) affect DG(t+A) by the delay time caused by infusing. Parameter A can be derived as follows: A=argmax(A, E{B(t)DG(t+A)}), being the parameter which maximizes the expectancy of the multiplied series B(t)*DG(t+A).

Following the determination of the time delay (A), a series of [DG(t+A), B(t)] can be defined and used. Therefore, in some embodiments, the relationship between basal rates and a change of glucose level is represented by the series [DG(t+A), B(t)], thereby obtaining a series of basal treatment rates and corresponding changes in glucose level in a treated patient, a series from which basal rate can be calculated as disclosed herein In some embodiments, the basal periods are set or determined as follows. These basal periods can be defined manually or be automatically deducted from the data. By way of non-limiting example, predefined basal periods of the day can be set to: 0000 h-0300 h, 0300 h-0700 h, 0700 h-1100 h, 1100 h-1500 h, 1500 h-2000 h and 2000 h-2400 h. The learning procedures will produce the required basal rate for these basal periods. In some embodiments, the required basal rate is determined for each of these basal periods. Once the basal periods are defined or automatically deducted, the algorithm will match the BaS data or the raw data to each of the basal periods and conduct the analysis to calculate the needed basal rate for the basal periods.

Basal rate for a paired basal period, e.g. <time period, basal rate>, can be calculated as follows:

minimizing changes in blood glucose algorithm: the series [DG(t+A), B(t)] in the BaS section can be interpolated by using the series values to find B(t) corresponding to the condition that DG(t+A)=0, and selecting the basal treatment rate which minimizes a change in the glucose level (e.g. B(t)) from the series of basal treatment rates previously calculated).

Performing slope related algorithm: This procedure is designed to determine whether the patient is in need for change of the basal treatment rate based on the value of dG and the glucose level at the end of each "clean data" section (e.g. the BaS section). Where dG is above a predetermined threshold and glucose level at the end of the section is higher than a predetermined value, basal treatment rate needs to be increased at a corresponding preset insulin treatment. Where dG is below a predetermined threshold and glucose level at the end of the section is lower than a predetermined value, basal treatment rate needs to be decreased at a corresponding preset insulin treatment. By way of non-limiting example, in case dG>–40 mg/dl and the glucose level at the end of the section is higher than 120 mg/dl, the basal treatment rate needs to be increased. Another example can be provided as follows. In case dG <–40 mg/dl and the glucose level at the end of the section is lower than 150 mg/dl, the basal treatment rate needs to be increased. The amount of the decrease or increase (i.e. corresponding preset insulin treatment) can be set as a constant amount in units/hour. Alternatively, it can be set as a percentage from the previous basal treatment or can be as function of dG and the previous basal treatment.

Performing glucose level algorithm: This procedure utilizes raw low data which need not be cleaned or preprocessed, i.e. general log data of glucose level and basal are used. Thus, the present invention uses raw data to support and/or adjust clean data sections. This procedure is designed to determine whether there is a need to change the basal treatment rate based on accumulation of data during specific basal periods as defined above. Informative raw data is enhanced by accumulation of data in shared time slots or periods.

Therefore, the procedure aligns and optionally aggregates raw glucose level data of plurality of basal periods, thereby enhancing essential information embedded in the raw data. In some embodiments, the glucose level data of two or more days is aligned. Alignment can be in the form of matching a first glucose level data point of a shared basal period with paired (or second) glucose level data point of the shared basal period, where $(r_1, x)$ is aligned with $(r_2, x)$, $r_1$ being a glucose reading of $day_1$ and $r_2$ being a glucose reading of $day_2$, and x is the shared basal period. In some embodiments, alignment can be in the form of matching a first glucose level data point of a shared timestamp in a first day with a paired (or second) glucose level data point of about the same timestamp in a second day. e.g. $(r_1, x)$ is aligned with $(r_2, x)$, $r_1$ being a glucose reading of $day_1$ and $r_2$ being a glucose reading of $day_2$, and x is the shared timestamp. In some embodiments, the alignment procedure exposes unique expressed glucose patterns. The aligned glucose data is processed to determine, for example, a representative glucose level for the shared basal periods or shared timestamps. The representative glucose level can be selected to be the median glucose level of the aligned glucose levels in the basal period. The representative glucose level can be selected to be an aggregated value of the aligned glucose levels in the basal period. In some embodiments, the difference between the median glucose level and target glucose level is determined.

Figure 2:
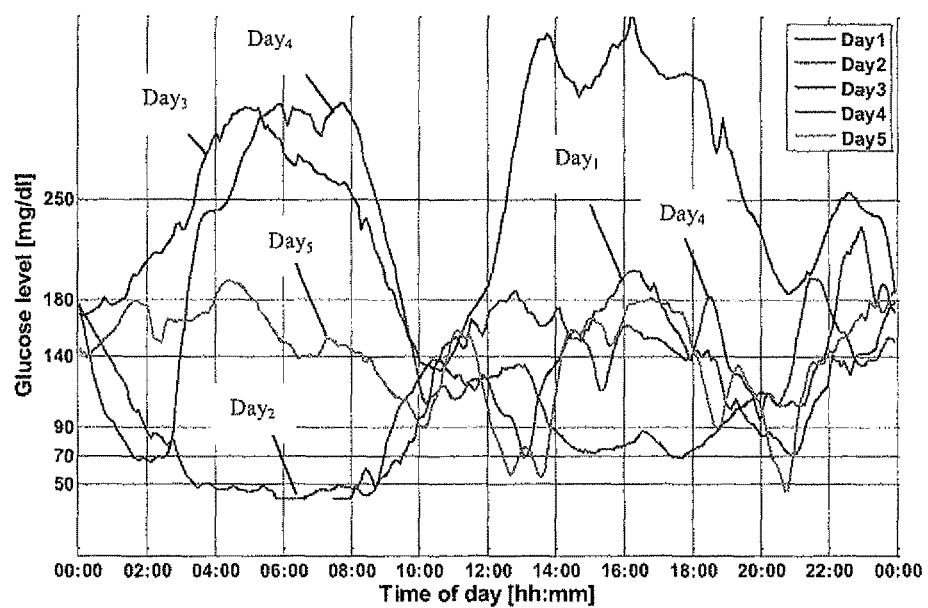
FIG. 2 is an exemplified glucose analysis for the glucose level procedure to determine the setting of the basal plan. The figure indicates division and aggregation of the raw log data prior to the analysis.
Figure 3:
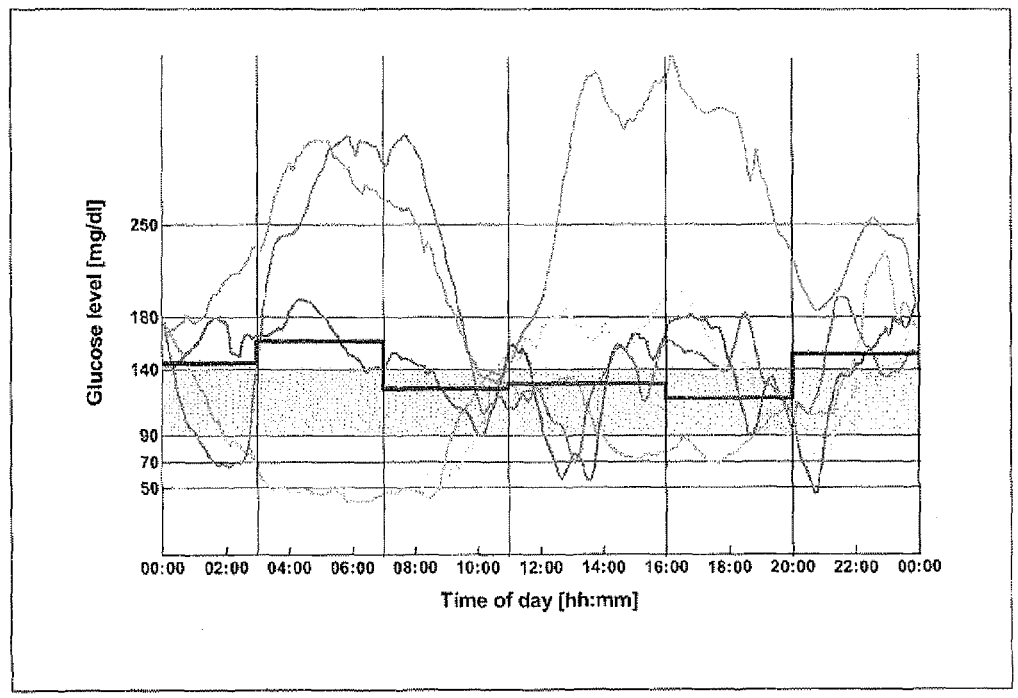
FIG. 3 is an exemplified glucose analysis for the glucose level procedure to determine the setting of the basal plan. The time line of the raw log glucose readings data after division and aggregation is presented with light lines. In this example, the basal periods are set to 00:00, 03:00, 07:00, 11:00, 15:00 and 20:00. The figure also provides the median glucose level (bold line) for each basal period and the target range (shaded area) which is set to 90-140 mg/dl.

In an exemplary embodiment, the Glucose level algorithm may be as follows:

(a) glucose level data of several calendar days is aligned; and the data is aggregated according to the basal period of day. In this connection, reference is made to FIG. 2 which is an example of the glucose analysis for the glucose level procedure to determine the setting of the basal plan. The figure indicates alignment of divided periods and aggregation of the raw log data prior to further analysis. FIG. 2 exemplifies the aligned glucose level data. The aligned glucose data points in FIG. 2 are shown in the form of a graph. The inventors have found that aligning glucose level data isolates and unravels informative elements of the glucose level data which otherwise could be overlooked. Additionally, it permits unsupervised determination of insulin pump settings by exposing the informative elements of glucose data to further analysis;

(b) determination of the average glucose level for the basal periods for each calendar day;

(c) determination of the median of the average glucose level for the basal periods for calendar days as a representative value for further analysis. Turning back to FIG. 3, it shows an example of the glucose analysis where the time line of the raw log data was divided to basal periods/section of (00:00, 03:00, 07:00, 11:00, 15:00 and 20:00). The figure also provides the determined median glucose level for each basal period and the target range which is set to 90-140 mg/dl. The median glucose levels were calculated as described above;

(d) evaluation of the difference between the determined median values and the target range for each basal period, as follows:

(d.1) if the difference is within the target range, the basal rate for this basal period remains unchanged;

(d.2) if the difference is above the target range, the basal rate for this basal period is increased; and (d.3) if the difference is below the target range, the basal rate for this basal period is decreased.

The amount of the reduction or increase can be set as a constant amount in units/hour, or can be set as a percentage from the previous basal treatment, or can be a function of the difference between the median and the target glucose level and the previous basal treatment. In the example shown in FIG. 3, the procedure will recommend to increase the basal rate in the basal period 03:00-07:00 and 20:00-00:00 before considering the time delay calculated as mentioned above.

The basal plan settings of the insulin pump can be set according to a weighted average of the Glucose level procedure, Slope related algorithm and/or Minimizing changes in blood glucose algorithm. The obtained basal treatment rate, taken as one or a weighted average (of Glucose level procedure, Slope related algorithm and/or Minimizing changes in blood glucose algorithm), can be used to modify the basal plan of the treated patient, e.g. by modifying the basal plan of an insulin pump.

In some embodiments, basal plan settings of the insulin pump can be set according to the Glucose level procedure. In some embodiments, basal plan settings of the insulin pump can be set according to the minimizing changes in the blood glucose algorithm.

In some embodiments, the present invention relates to a basal plan module; the basal plan module is configured and operable to perform the procedures for unsupervised learning of the basal plan or rate; the basal plan module is configured and operable to analyze BaS being provided as input; the input is processed to produce output signal indicative of global insulin pump settings of basal plan. In other embodiments, the basal plan module is configured and operable to analyze raw log data provided as input; the input is processed to produce output signal indicative of global insulin pump settings of basal plan. In other embodiments, the basal plan module is configured and operable to analyze Bas and raw log data both being provided as input; the input is processed to produce output signal indicative of global insulin pump settings of basal plan.

Learning Active Insulin AIF Algorithm

The present invention permits the unsupervised learning of the active insulin function (AIF) tailored specifically for the treated patient. In some embodiments, the present invention thus provides methodologies, devices and systems which can obtain a patient dependent active insulin function (AIF) instead of the conventional trial and error procedures adopted by the physicians.

In general, AIF describes the amount of the insulin "active" in the blood at a certain time. AIF is a measure for the specific pharmacodynamics characteristics for insulin (denoted as active insulin). In the present invention, AIF is a measure for the specific pharmacodynamics for the treated patient Active insulin can be defined with reference to a specific meal, to a series of meals, to a specific insulin bolus event or a series of insulin bolus events. In some embodiments, therefore AIF is determined from BS and MS Sections.

Figure 14:
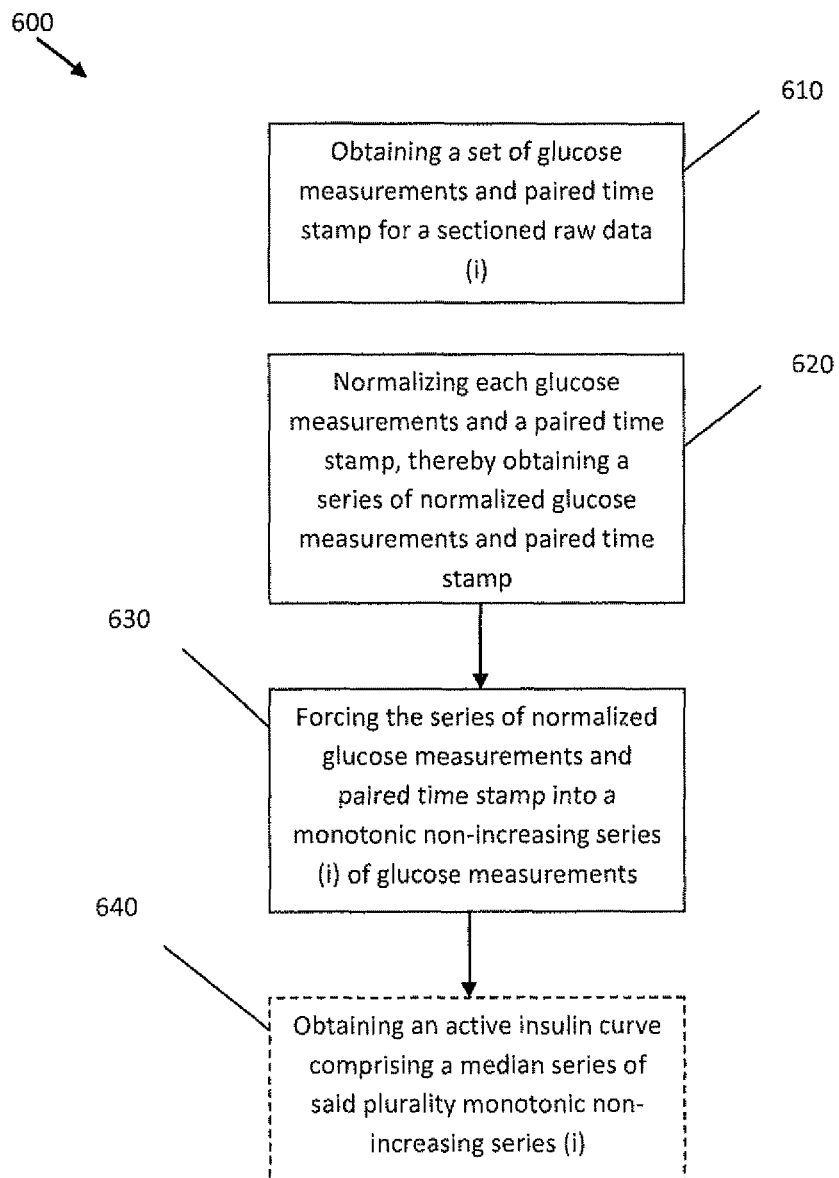
FIG. 14 shows a flow chart of a procedure for unsupervised determination of the active insulin function, according to an embodiment of the invention.

Reference is made to FIG. 14 which is a flow chart 600 illustrating a procedure for unsupervised determination of the active insulin function. This procedure 600 includes obtaining a set of glucose measurements and paired time stamp for a specific sectioned raw which can be denoted as (i) (step 610). These glucose measurements and paired time can be obtained from raw log data. The set of glucose measurements are thereafter normalized thereby obtaining a series of normalized glucose measurements and paired time stamp (step 620). The informative data piece such as the active insulin functions or curves can be thus obtained as follows.

The input glucose measurement data, either normalized or not, is then processed for normalizing each of the glucose measurements and paired time stamp into a monotonic non-increasing series (i) of glucose measurements and paired time stamps (step 630), or into a substantially monotonic non-increasing series (tolerating about +/−10 percent divergences from the monotonic non-increasing series). The inventors have found that the substantially monotonic non-increasing (or the monotonic non-increasing) series well defines the active insulin characteristic of the treated patient 640 (user dependant pharmacodynamics behavior instead of the fixed constant or fixed function which is conventionally used).

In some embodiments, a plurality of active insulin functions or curves is obtained from analysis of plurality of sectioned raw data. This can be followed by determination of the median series of said plurality of monotonic non-increasing series. The median series represent the AIF for the plurality of sectioned raw data (or plurality of sections of raw data).

Therefore, in some embodiments, AIF is determined in accordance with the procedure comprising the following.

AIi is defined as the active insulin for event (i) which is, optionally, meal or insulin bolus event. The time of the event is denoted as $(T_0)$. Any event has a starting time point and an ending time point. These points define a first time window. In some embodiments, for each event, the starting time point is defined as starting from the specific event $(T_0)$ as being provided from home care data (log data). The event is ended where, for example, the next event starting time occurs or following about seven hours from the starting time point (the earlier of the two).

As used herein, peak sensor value following the event is identified and denoted as $S_{mmax}$. Minimum sensor value which occurred following the peak is denoted as $S_{mmin}$. The respective time tag when the peaks where obtained is typically recorded, defining a second time window between the time $S_{mmax}$ and $S_{mmin}$.

Sensor data (e.g. raw log sensor data) during the second time window is obtained. The obtained sensor data can be represented by a series of $[T_i, V_i]$, where $(T_i)$ are the time tags of sensor readings measured at the beginning of the meal $(T_0)$, and $(V_i)$ are sensor values measured at their respective $(T_i)$.

In some embodiments, the measured sensor data is normalized to values ranging between 0 and 1. $(N_i)$ represents the normalized value of the respective $(V_i)$ and can be calculated as follows:

$Ni = Vi/(S_{mmax} - S_{mmin})$.

Normalized series [Ti, Ni] can thus be obtained.

In some embodiments, the series (either [Ti, Vi] or [Ti, Ni]) are modified (or "forced") into a monotonic series such as a monotonic non-increasing series. Thus, a non-increasing series is obtained by associating each $(N_i)$ to a minimum normalized $(N_j)$, j=1 to i.

This can be performed by sequentially inserting the items of the series (either [Ti, Vi] or [Ti, Ni]) into the non-increasing monotonic series if the sensor values in those items do not exceed any of the sensor values previously inserted e.g. discarding those breaching values. In this regard, sequentially implies processing from a starting time point to an ending time point.

In other words, $(N_i)$ can be obtained as follows, $Ni = \min(\{Nj\}, j=1:i)$.

By way of a non-limiting example, for the series $N_j = \{1, 0.9, 0.8, 1.2, 0.7\}$, $N_i$ will be $\{1, 0.9, 0.8, 0.8, 0.7\}$.

The meal peak value, i.e. at $(T_0)$, can be added. Thus, $[T_0, 1]$ is added at the beginning of the series $[T_i, N_i]$.

The series thus obtained represents the active insulin AIi for a specific meal or a bolus insulin event.

Where more than one meal took place or where more than one bolus event took place or where one had several meal and bolus insulin events, the active insulin series for a set of events can be obtained. The active insulin for a set of events is the median of all the meal series {AIi}. The resultant series, denoted as AI_total, represents an active insulin curve applicable to all events. The values in AI_total represent the percentage of insulin which is still active in the treated patient. For example, elements of [t=25, v=0.8], within the AI_total series, can indicate that 25 minutes after injecting a bolus, 80% percent of insulin was still active.

In some embodiments, the present invention relates to an AIF module; the AIF module is configured and operable to perform the procedures for unsupervised learning of the active insulin curve or function; the AIF module is configured and operable to analyze MS being provided as input; the input is processed to produce output signal indicative of global insulin pump settings of insulin activity curve parameter. In some embodiments, the AIF module is configured and operable to analyze BS being provided as input; the input is processed to produce output signal indicative of global insulin pump settings of insulin activity curve parameter. In some embodiments, the AIF module is configured and operable to analyze BS and MS both being provided as input; the input is processed to produce output signal indicative of global insulin pump settings of insulin activity curve parameter.

Learning CR Algorithm

The carbohydrate ratio (CR) is measured in units of [gram/Units]. The carbohydrate ratio (CR) assesses or quantifies the exact amount of insulin needed to compensate for the consumed CHO. Optionally, the assessed CR adjusts the time (in the present invention preferably 3 hours) anticipated for the glucose levels to return to the level that was at the meal time. In practice, patients are not consistent in the daily routine (which sometime causes the settings inserted in the pump to be inappropriate). In many cases, the appropriate CHO to insulin ratio will vary and diverge from parameter being set in the insulin pump. In many times, this diverge relates to the fact the patients do not estimate correctly the amount of CHO in the meals they consume. Hence, the unsupervised learning CR algorithm of the present invention addresses the need for CR determination with is determined or adjusts accordingly.

Figure 12:
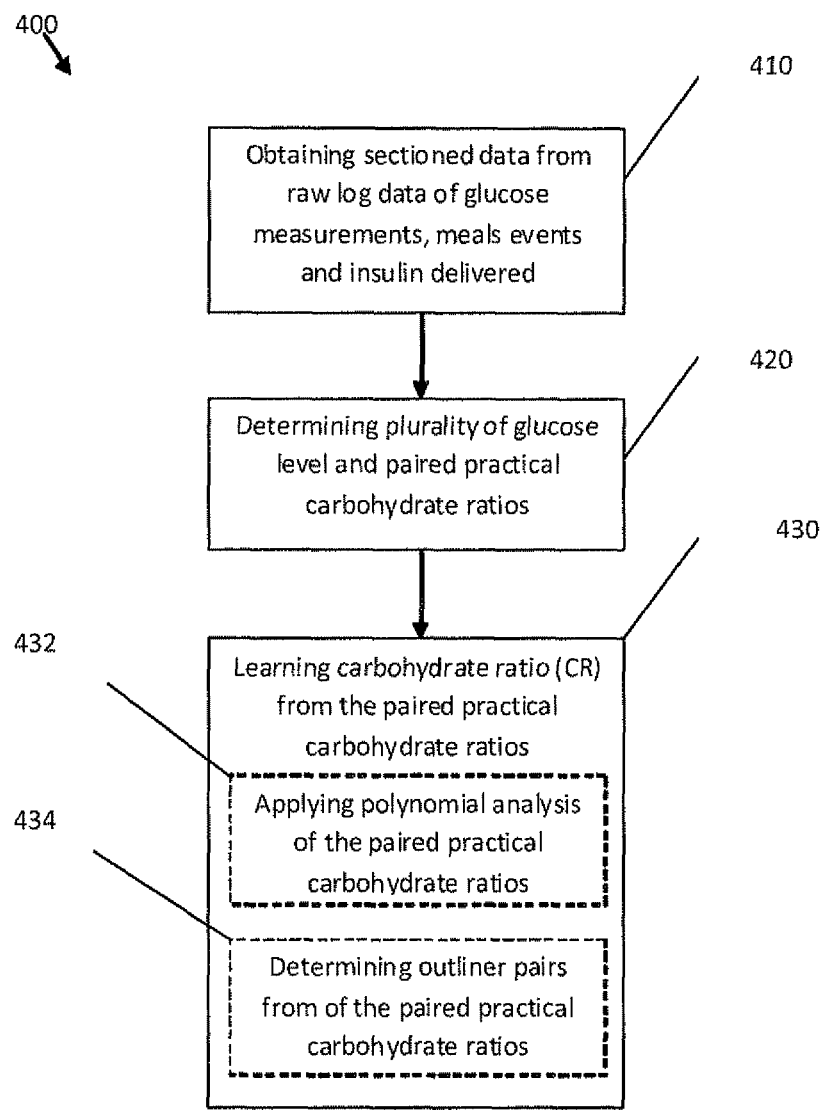
FIG. 12 is a flow chart illustrating a method for unsupervised determination of the carbohydrate ratio (CR).

FIG. 12 is a flow chart 400 illustrating a method for unsupervised learning of the carbohydrate ratio (CR) in accordance with an embodiment of the invention. The unsupervised CR learning method 400 includes obtaining sectioned data from the raw log data of glucose measurements, meal events and insulin delivered 410. CR learning method 400 can use the MS Sections of the data to obtain informative data pieces as follows. The sectioning procedures were provided above and are applicable in the present context. The method 400 further includes determining plurality of glucose level and paired practical carbohydrate ratios. The application of the method 400 thus produces pairs of glucose level and candidate carbohydrate ratio 420. In procedure 430, carbohydrate ratio (CR) is learned from the candidate practical carbohydrate ratios which were previously determined. These candidate practical carbohydrate ratios are informative pieces with are further processed to obtain final CR as follows. In some embodiments, polynomial analysis 432 of the paired practical carbohydrate ratios is applied. In other embodiments, outliner pairs from the paired candidate carbohydrate ratios are determined and optionally removed before performing the polynomial analysis 434. The resultant candidate carbohydrate ratios can be also selected by a voting procedure (not shown) in which the agreed majority of candidate carbohydrate ratios is used or selected as the CR. In other embodiments, combination (such as weighted combination) of both polynomial analysis and voting procedure is used for the determination of a final CR. Specific example of the procedure of determining CR was provided above and is applicable in this respect.

In one more specific but non-limiting embodiment, carbohydrate ratio (CR) is determined according to the procedure comprising the following:

calculating the practical CR (pracCR) per MS section.

Practical CR (pracCR) denotes the ratio of CHO to the actually delivered insulin. In some embodiments, the practical CR (pracCR) is determined for the paired MS section (pracCR in the MS section). In some embodiments, the practical CR (pracCR) is determined for each paired MS section. These procedures result with series of paired values: Ser={Diff(i), pracCR(i)}, (i) being a data section enumeration, as defined below.

i) Practical Carbohydrate Ratio (PracCR) in Meal Sections:

The following method determines the pracCR for each MS section. The method addresses the required separation or isolation of meal effect from a bolus effect.

For each meal section, MS (i), in the MS sections which were previously determined, perform a procedure comprising:

(1) obtain the total insulin boluses given in MS (i), denote as $B_{tot}$;

(2) calculate the active insulin (AI) at the beginning of the section, in MS (i), denote as $AI_{start}$; AI is determined in accordance with an active insulin function (AIF) of the treated patient, as can be determined from open-loop measured data (defined herein above);

(3) determine the active insulin (AI) at the end of the section, in MS (i), denote as $AI_{end}$;

(4) calculate the insulin in section with RelIns(i)=$B_{tot}$+$AI_{start}$−$AI_{end}$;

(5) obtain the glucose sensor value at the beginning of the section, MS (i), denote as $S_{start}$. In one embodiment, a single glucose sensor value is obtained. In other embodiments, an average of several glucose sensor values is obtained;

(6) obtain the sensor value at the end of the section, denote as $S_{end}$. In one embodiment, a single glucose sensor value is obtained. In other embodiments, an average of several glucose sensor values is obtained;

(7) calculate the difference between start and end points as follows: Diff(i)=$S_{end}$−$S_{start}$;

(8) obtain the total carbohydrates consumed in the section, denote as $C_{tot}(i)$;

(9) determine the practical CR for the section, pracCR(i)=$C_{tot}(i)$/RelIns(i).

The active insulin function (AIF) of the treated patient can be a just-in-time AIF setting to estimate the active insulin in the MS Section. The just-in-time AIF can be an AIF parameter just being calculated in time proximity to the CR calculation e.g. AIF setting calculated for the MS section.

Following the application on meal section (i), the following series results: Ser={DiffBG(i), pracCR(i)}. The series comprises blood glucose changes in a meal section and paired determined practical carbohydrate ratio.

Methods and procedure are employed to extract final carbohydrate ratio (CR) from the above obtained series. In some embodiments, prior to use the CR extraction methods, outlier pairs are removed, thereby obtaining series Ser which can be denoted as Ser_out={$DiffBG_{out}(i)$, $pracCR_{out}(i)$}, i.e. series with omitted outliner. While the embodiment described below uses the Ser_out series, it should be understood that in some embodiments the Ser series can be used.

Polynomial CR Extraction Method:

A polynomial equation of order K can be fitted for the series Ser_out, and the resulting function F(*) will produce CR_k=F(Diff). Extracted CR can be calculated from the obtained fitted function e.g. by providing a desired input DiffBG to output the resulting CR from the fitted function. The desired difference, DiffBG, for a treated patient is typically −0 (e.g. DiffBG=0). The extracted CR can be calculated from fitted for optimal BG difference which is DiffBG=0, as the function input. The resulted CR_m=F(DiffBG) for DiffBG=0 is the desired CR.

Voting Cr Extraction Method:

The minimal possible $CR_k$ such that for any CR>=$CR_k$, 75% of matching DiffBG{i} will be with DiffBG{i}>ThreshVal (for the desired ThreshVal>0). The $CR_k$ that was found is the desired CR of this extraction methods. It should be noted that the procedure is not restricted to 75% of matching DiffBG{i} but other rates could be used.

In some embodiments, the final learned CR can be obtained as one or as a weighted average of the above extraction embodiments.

Figure 4:
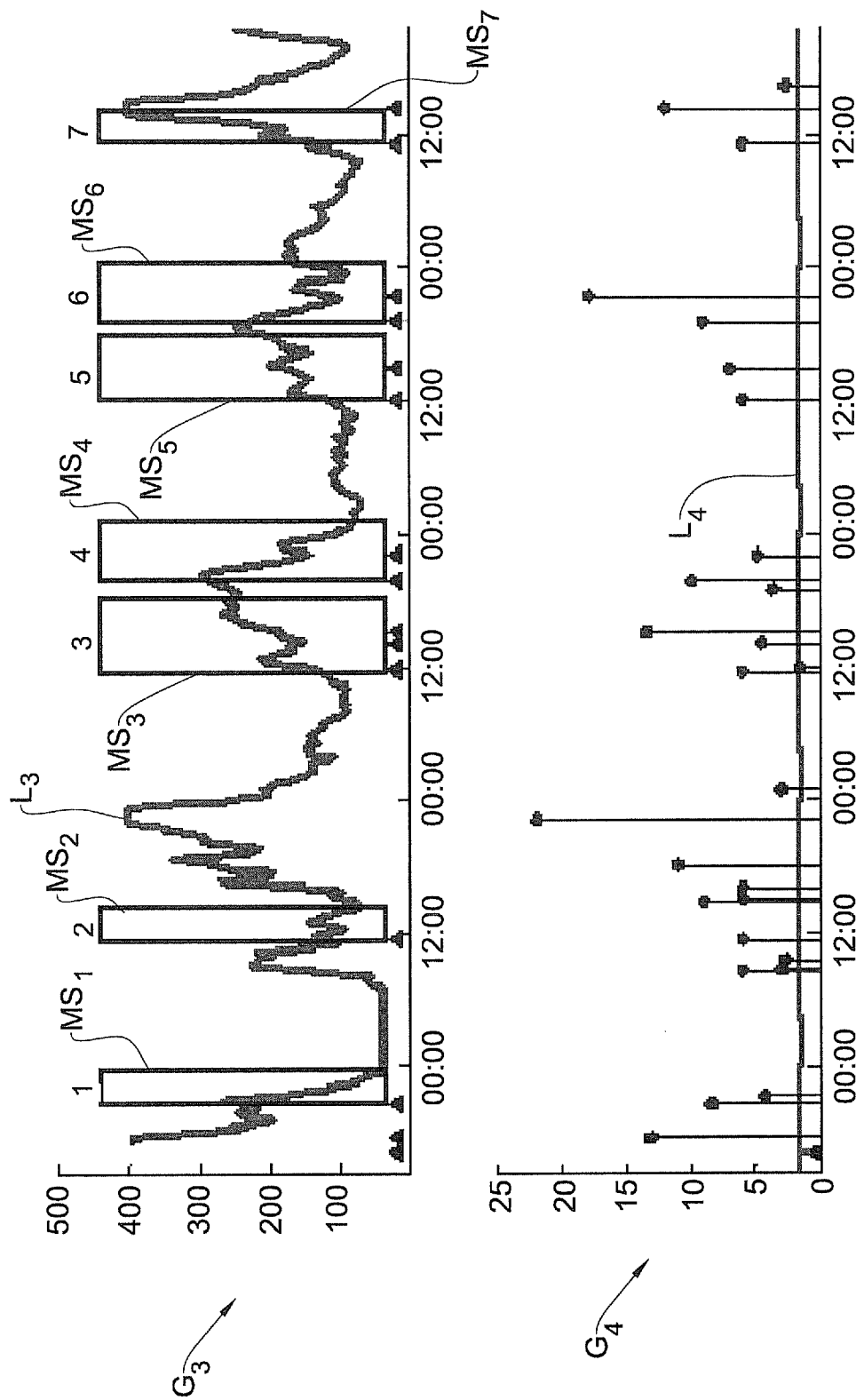
FIG. 4 is an exemplary meal section derived from Meal Sections (MSs: $MS_1$-$MS_7$) for calculating the recommended carbohydrate ratio (CR). The top graph $G_3$ presents the glucose level (blue line, $L_3$) where meal events are marked using a black triangle. The bottom graph $G_4$ presents the insulin treatment, where the horizontal line $L_4$ is the basal rate and the vertical lines with the black circle are the boluses. The sections are marked in numbers and with black frame.

The following non-limiting example illustrates the unsupervised procedures for determining the final carbohydrate ratio (CR). FIG. 4 is an exemplary meal section derived from Meal Sections (MSs) for calculating the recommended carbohydrate ratio (CR). The data shown in FIG. 4 comprises raw log data of continuous glucose sensor readings, insulin pump delivery over time, and meal data. The top graph $G_3$ presents the glucose level where meal events are marked using a black triangle. The bottom graph $G_4$ presents the insulin treatment, where the horizontal line $L_4$ is the basal rate and the vertical lines with the black circle is the boluses. The sections are marked in numbers and with black frame.

Figure 5:
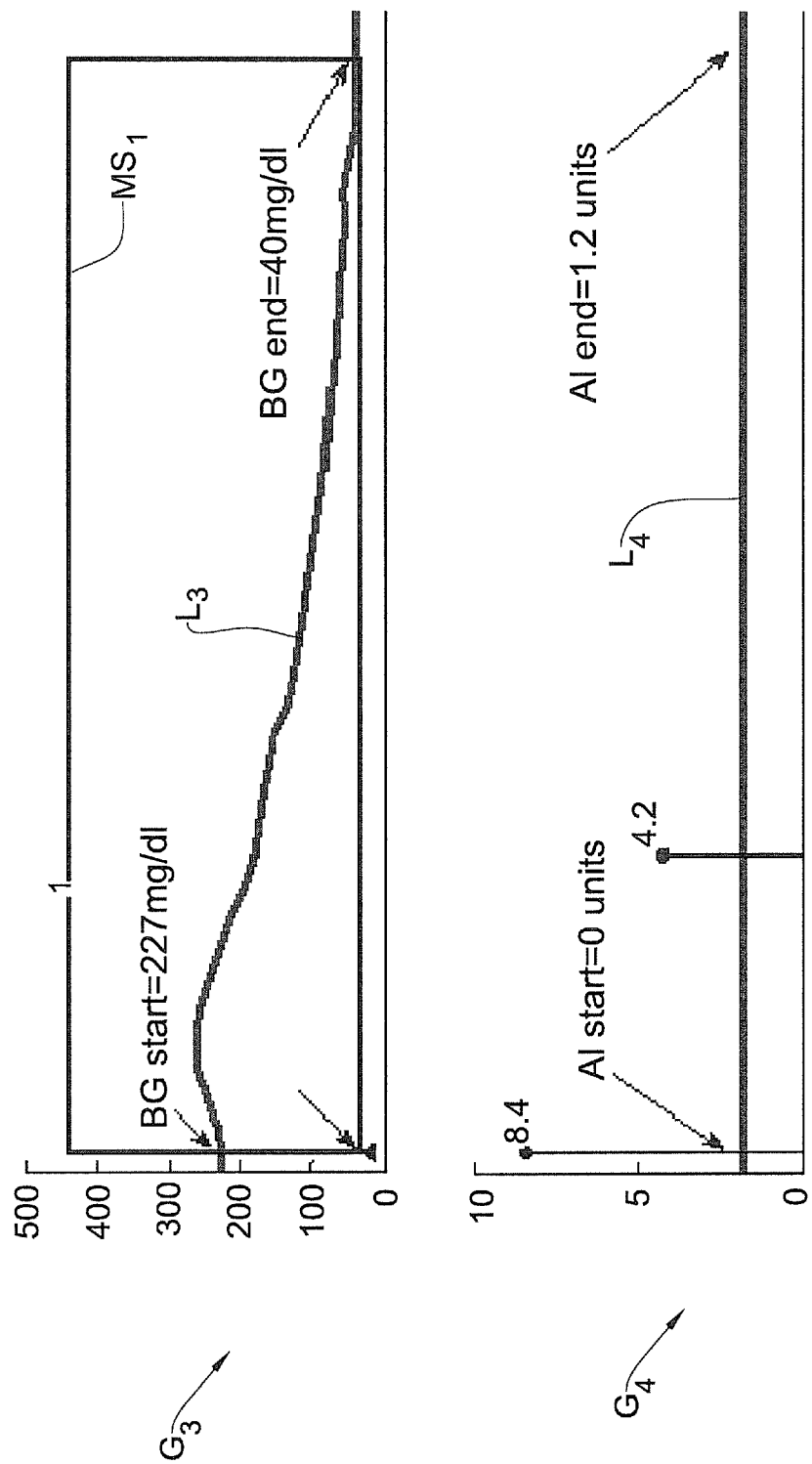
FIG. 5 is an illustration in which section $MS_1$ of FIG. 4 is focused on. The top graph $G_3$ presents the glucose level (blue line $L_3$) where meal events are marked using a black triangle, $MS_1$. The bottom graph $G_4$ presents the insulin treatment, where to the horizontal line $L_4$ is the basal rate and the vertical lines with the black circle are the boluses.

In the current example, the initial CR setting in the insulin pump of this patient is 7 gram/units. FIG. 4 also shows the identified meal sections (MS) sections for this log data set marked as $MS_1$-$MS_7$. In FIG. 5 section $MS_1$ of FIG. 4 is focused on. FIG. 5 shows the calculation for the pracCR and DiffBG for section $MS_1$. As shown, FIG. 5 contains only one meal. Employing the above described method with the data marked on the figure, the following pair is determined: pracCR=7 gram/units and DiffBG=−187 mg/dl.

Figure 6:
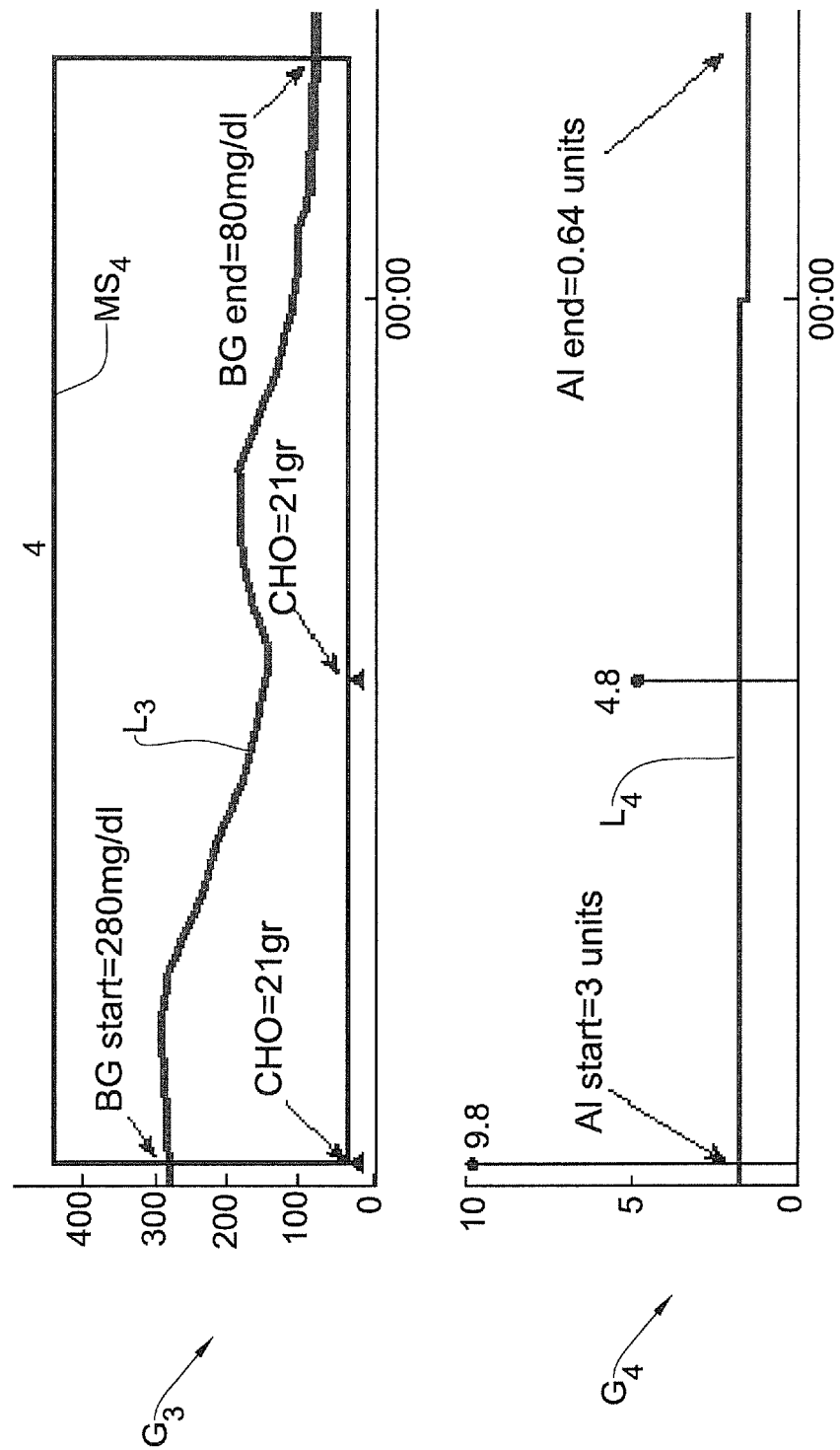
FIG. 6 is an illustration in which section $MS_4$ of FIG. 4 is focused on. The top graph $G_3$ presents the glucose level (blue line $L_3$) where meal events are marked using a black triangle. The bottom graph $G_4$ presents the insulin treatment, where the horizontal line $L_4$ is the basal rate and the vertical lines with the black circle are the boluses.

In FIG. 6 section $MS_4$ of FIG. 4 is focused on. FIG. 6 shows $MS_4$ which is an example for a meal section that contains more than one meal. The top graph $G_3$ presents the glucose level where meal events are marked using a black triangle. The bottom graph $G_4$ presents the insulin treatment, where the horizontal $L_4$ line is the basal rate and the vertical lines with the black circle is the boluses. Employing the above described method with the data marked on the figure, the following pair is determined: pracCR=2 gram/units and DiffBG=−200 mg/dl.

Figure 7:
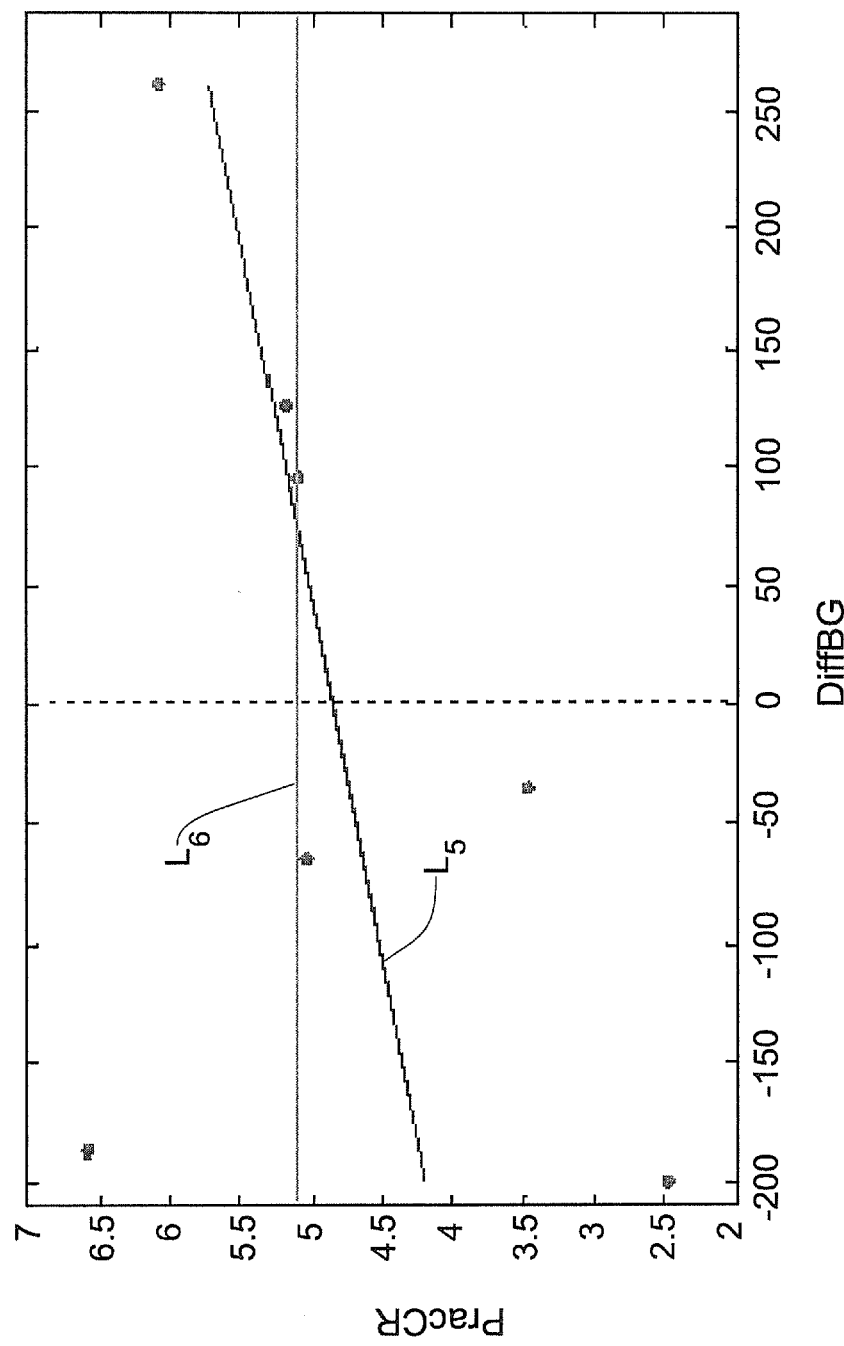
FIG. 7 is an illustrative plot diagram of the pairs Ser={DiffBG(i), pracCR(i)} (red dots). The blue line $L_5$ is the result of the polynomial analysis while the green line $L_6$ is the result of the voting analysis and the dash line marks the line of DiffBG=0.

FIG. 7 is a plot diagram of the pairs Ser={DiffBG(i), pracCR(i)} calculated for MSs, $MS_1$-$MS_7$. The blue line $L_5$ is the result of the polynomial analysis while the horizontal green line $L_6$ is the result of the voting analysis. After conducting determining the Ser={DiffBG(i), pracCR(i)} of $MS_1$-$MS_7$ in accordance with the above methods the final CR can further be derived. FIG. 7 shows the scatter plot of Ser, with the analysis of polynomial method (resulting with graph $L_5$) and the voting method (resulting with graph $L_6$). The determined final CR for this example is about 5 gram/units resulting from weighted combination of both polynomial method and the voting methods.

By way of a non-limiting example, for the determination of CR, polynomial and voting technique can then be applied to identify a representative or final CR, techniques which have already been discussed. The selected final CR settings statistical significance stems from the fact that it was obtained from sampled raw data sections which are sectioned specifically for that determination and because of partial contribution of the different data pieces in the sectioned data input.

In some embodiments, the present invention relates to a carbohydrate ratio module; the carbohydrate ratio module is configured and operable to perform the procedures for unsupervised learning of the carbohydrate ratio; the carbohydrate ratio module is configured and operable to analyze MS being provided as input; the input is processed to produce output signal indicative of global insulin pump settings of carbohydrate ratio (CR) parameter.

Learning CF Algorithm

The correction factor (CF) is measured in units of [1 ng/dL/Unit]. The learning procedures of the present invention are provided herein below and address CF extraction in several scenarios (or data sections).

Figure 13:
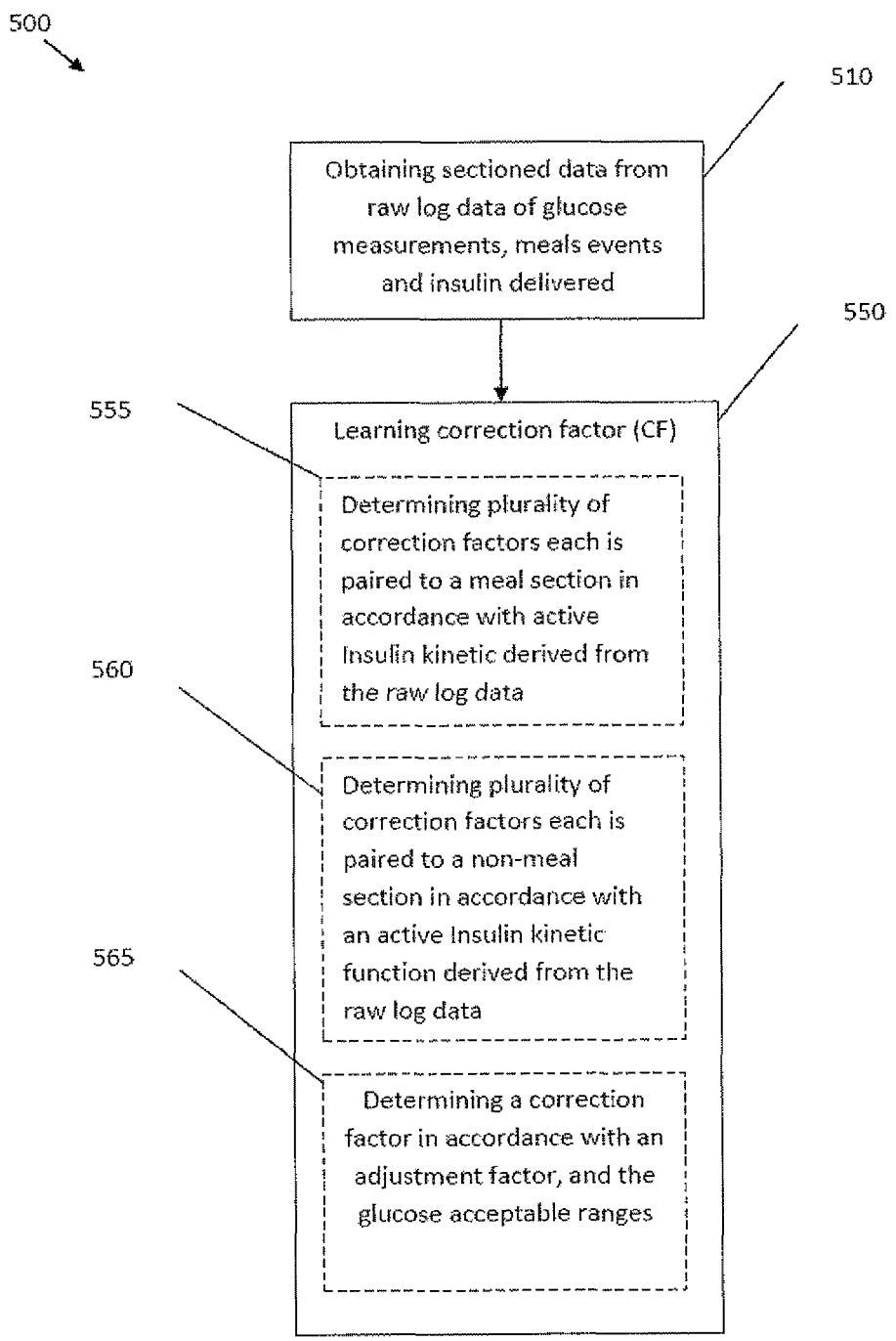
FIG. 13 is a flow chart illustrating a method for unsupervised determination of the carbohydrate ratio (CF) settings.

FIG. 13 is a flow chart 500 illustrating a method for unsupervised learning of the carbohydrate ratio (CF) settings in an embodiment of the present invention. The unsupervised CF learning method 500 includes obtaining sectioned meal and non-meal sections from raw log data of glucose measurements, meals events and insulin delivered 510. CF learning method 500 can utilize MS and BS data sections to obtain informative data pieces as follows. The obtained information pieces are used for the performance of a procedure 550 which determines the final correction factor setting. In some embodiments, the method 500 comprises determining plurality of correction factors each being paired to a meal section or a non-meal section, in accordance with active Insulin kinetics derived from the raw log data (555, 560 respectively).

In some embodiments, the method 500 comprises determining a correction factor in accordance with an adjustment factor which is determined, and the glucose acceptable ranges 565.

In some embodiments, final CF pump setting is selected from the plurality of correction factors. In other embodiments, correction factors of the plurality of correction factors are weighted and the combination of weighted correction factors can be used to produce a final CF pump setting.

CF extraction in several scenarios and/or data sections is provided as follows:

A. CF extraction from meal sections (MS) (denoted as $CF_{from\_MS}$): raw log data from this MS sections as well as the new calculated CR are used for the CF extraction.

In general, when a treated patient consumes a meal, the amount of insulin to be delivered includes two parts: (i) meal bolus (calculated with the CR settings of the insulin pump) and (ii) correction bolus (calculated with the current blood glucose (BG) level of the treated patient, CF settings of the insulin pump and the preset target level).

Normally, a correction bolus will be added only if the BG level at the beginning of the meal event is out of the target range. In case the amount of insulin that was delivered is sufficient, the glucose level following several hours from the meal time should be close to the target level. In case the blood glucose following several hours is (optionally 3 hours) is not close to the target, a modified CF is required. As the CR as described above is accurate, the meal bolus component is accurate, and therefore deviation from the glucose target is attributed to the second CF dependant component.

Correction factor determination for section MS (i) can be performed by employing the following method:

(1) determining the Insulin that was given at section MS (i) which can be optionally calculated as follows:

$$I_{given,i} = A.I_{start,i} + \sum_{in\_section} \text{Insulin\_Bolus}_i - A.I_{end,i}$$

where: $A.I_{start}$ and $A.I_{end}$ is the active insulin at the beginning and at the end of section MS(i), calculated using the patient dependant AIF or other methods for determining AIF disclosed herein.

(2) determining the amount of insulin that should be delivered to cover the CHO in section MS (i); In some embodiments, the insulin to be delivered is determined according to the following formula:

$$I_{modified\_for\_meal,i} = \frac{\text{Total\_Carb}_i}{CR_{New}}$$

In some embodiments, $CR_{new}$ is being the final CR determined in accordance with the CR learning procedure disclosed herein.

(3) In case the glucose level at the beginning of section MS; is not in the target zone, i.e. in case there is a need for correction bolus, the following calculation is used:

$$I_{additional\_correction,i} = \frac{BG_{end,i} - \text{Target}}{CF_{original}}$$

$$I_{estimated\_correction\_needed,i} = I_{given,i} - I_{modified\_for\_meal,i} + I_{additional\_correction,i}$$

$$CF_{new,i} = \frac{BG_{start,i} - \text{Target}}{I_{estimated\_correction\_needed,i}}$$

The resulted $CF_{from\_MS}$ can be used for setting the insulin pump accordingly. The resulted $CF_{from\_MS}$ for the above procedure can be the average of several $CF_{new,i}$ being calculated according to the above procedure.

In some embodiments, a correction factor (CF) is determined for the meal and is calculated by processing the AIF to estimate the active insulin in the MS Section and a just-in-time carbohydrate ratio (CR), previously denoted as $CR_{new}$. The utilization of a just-in-time carbohydrate ratio allows for better estimation of the CF being calculated as the calculation is based on an updated value of the CR.

Figure 8:
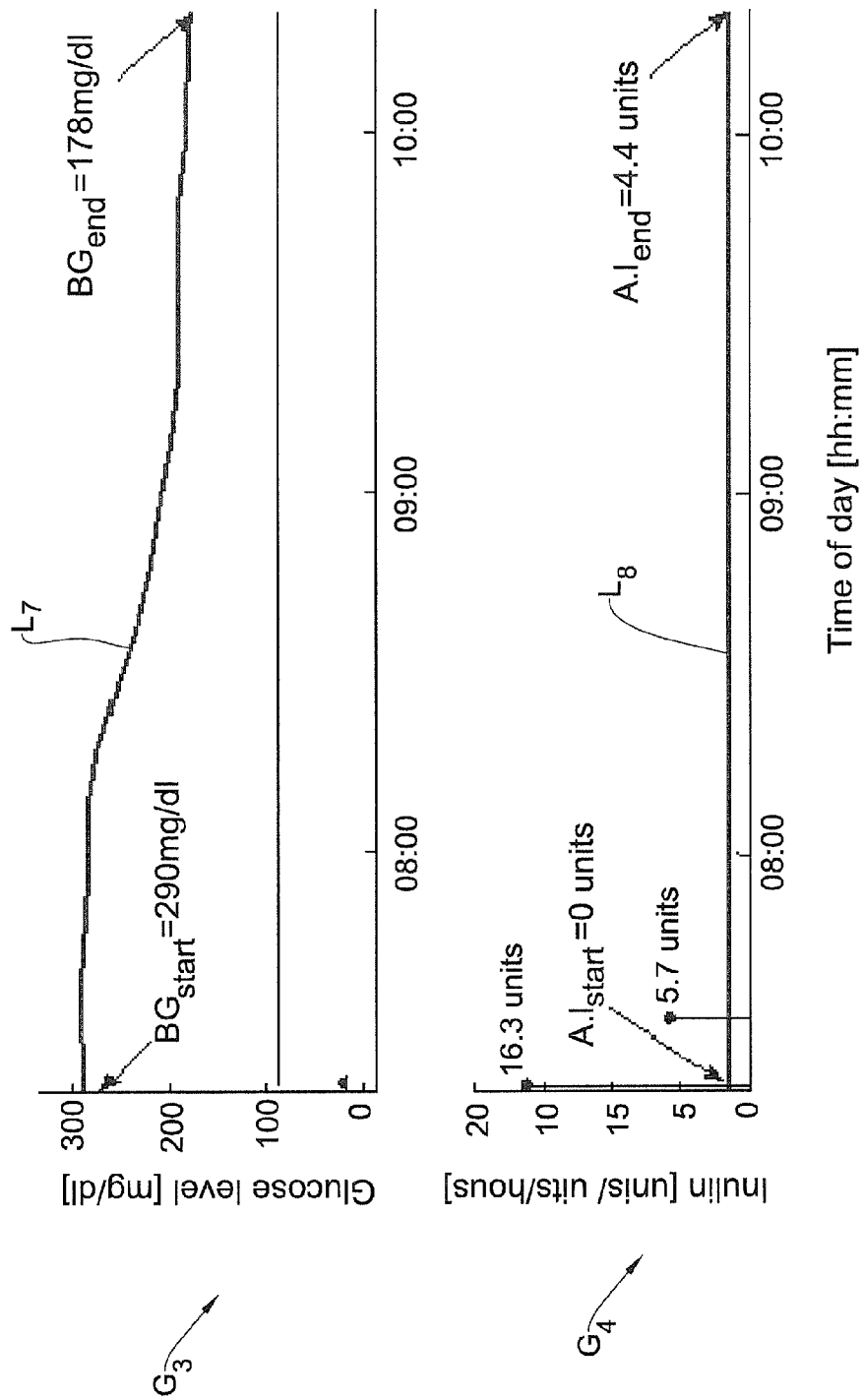
FIG. 8 provides an illustration MS section analysis resulting with calculating CF settings. The MS time stretch was determined in accordance with a MS sectioning procedure. The top graph $G_5$ presents the glucose level (blue line $L_7$) where meal events are marked using a black triangle. The bottom graph $G_6$ presents the insulin treatment, where the horizontal line $L_8$ is the basal rate and the vertical lines with the black circle are the boluses.

FIG. 8 presents a non limiting example for calculating the CF for a meal section according to this algorithm. The top graph $G_5$ presents the glucose level (line $L_7$) where meal events are marked using a black triangle. The bottom graph $G_6$ presents the insulin treatment, where the horizontal line $L_8$ is the basal rate and the vertical lines with the black circle is the boluses.

The inputs in the example of FIG. 8 are as followed: $CF_{original}$=16 mg/dl/units; $CR_{original}$=7 gram/units; $CR_{New}$=5 gram/units; Carb=80 gram; and Target=110 mg/dl.

Application of the above CF extraction procedure is produced the following determinations:

$$I_{given,i} = \sum_{in\_section} \text{Insulin\_Bolus} = 16.3 + 5.7 = 22$$

$$I_{modified\_for\_meal,i} = \frac{\text{Total\_Carb}_i}{CR_{New}} = \frac{80}{5} = 16$$

$$I_{additional\_correction,i} = \frac{BG_{end,i} - \text{Target}}{CF_{original}} = \frac{178 - 110}{16} = 4.25$$

$$I_{estimated\_correction\_needed,i} =$$

$$I_{given,i} - I_{modified\_for\_meal,i} + I_{additional\_correction,i} = 17.6 - 16 + 4.25 = 5.85$$

$$CF_{new,i} = \frac{BG_{start,i} - \text{Target}}{I_{estimated\_correction\_needed,i}} = \frac{290 - 110}{5.85} = 30$$

It should be noted that although the treated patient requires more units of insulin in order to come near the target level, the CF is increasing. It can be explained from the fact that some of the missing insulin units can be traced back to the meal component (since the CR changed from 7 to 5, thus the meal component of insulin increases). Therefore, the system decides to deliver less for the correction portion of insulin.

The above example with reference to FIG. 8 shows determination of the CF for a single MS section. Following the analysis of all meal sections, the $CF_{From\_MS}$ obtained was 19 (not shown).

B. CF extraction from non-meal sections (denoted as $CF_{non\_meal}$): raw log data from non-meal sections are used for the CF extraction. This method uses as input raw log data sections being BS sections or other sections which do not have the effect of meal. CF is extracted from the response to different dosing of boluses. The method comprises the following procedures. For a BS(i) section:

(1) determining the active insulin at the beginning of the BS(i) section using an AIF. $AI_{start}$ denotes the active insulin at the beginning of the BS(i) section. In some embodiments, the AIF is the patient dependent AIF which was previous determined. In some embodiments, the AIF is determined by employing the method disclosed herein for the determination of an AIF, at the beginning of the section (2) determining the active insulin at the end of the BS(i) section, denoted as $AI_{end}$.

(3) determining the total insulin boluses given in the BS(i) section, denoted as $B_{tit}$.

(4) determining the sensor value at the beginning of the BS(i) section, denoted as $S_{start}$.

(5) determining the sensor value at the end of the BS(i) section, denoted as $S_{end}$.

(6) Determining CFsec(i) using the following equation:

$$CF_{sec}(i) = (S_{end} - S_{start})/(B_{tot} + AI_{start} - AI_{end})$$

Optionally, the above procedure is performed for each BS(i) section.

In some embodiments, the final $CF_{non-meal}$ is an average over the positive elements in $CF_{sec}(i)$. In some embodiments, the final $CF_{non-meal}$ is $CF_{sec}(i)$ of the BS(i) section.

C. Fixed CF extraction with glucose levels adjustment (denoted as $CF_{BG\_Analysis}$): The method estimates the CF using a fixed ratio of dC and analyzes the glucose control performances of the patient in order to modify the fixed ratio calculation. In some embodiments, an initial CF, denoted as $CF_{initial}$, can be determined according to carbohydrate amount consumed, glucose measurements and insulin related data (insulin delivered, the basal plan and/or insulin bolus). The determination of $CF_{BG\_Analysis}$ can be performed as follows: (1) determining the initial Correction Factor. $CF_{Initial}$, in accordance with carbohydrate amount consumed, glucose measurements and insulin related data:

$$CF_{initial} = \frac{G_e - G_s + dC \cdot C}{B},$$

where $G_e$ is the last sensor reading [mg/dl] of the available data (could be one point or average of several points); $G_s$ is the first sensor reading [mg/dl] of the available data (could be one point or average of several points); dC is a glucose to carbohydrate ratio. The ratio of glucose to carbohydrate can be 3.33, (based on empirical knowledge); C is amount of carbohydrate consumed [e.g. gr] during the available data; and B is the amount of bolus insulin provided [units of insulin] during the available data. The use of dC is done in order to estimate an effect of the consumed CHO on the glucose levels.

$G_e$ and $G_s$ are being measured at two different time points. Therefore, the time interval between the two glucose sensor readings can be defined as a time window.

Such estimation can be performed by obtaining an amount of carbohydrate consumed in the time window and transforming the carbohydrate amount by determining a coefficient defining the proportion of consumed carbohydrate to glucose (dC above). By multiplying the coefficient with the amount of carbohydrate consumed in the time window, the glucose derived from the consumed carbohydrate is determined.

The unsupervised learning procedure of the present invention can include modification of the $CF_{initial}$ (or a current Correction Factor) based on analysis of the quality of glucose control of the patient using the raw log data that was collected while the patient was at home in his daily routine.

For example, the $CF_{initial}$ is modified in accordance with the minimum sensor reading or the lowest blood glucose reading recorded. In a specific example, the $CF_{initial}$ is modified in accordance with proportion between minimum sensor reading during the time window and the lowest blood glucose reading recorded. In some embodiments, the insulin sensitivity is modified in accordance to the maximum sensor reading in a time interval prior to obtaining the minimum sensor reading (an example is shown below). Therefore, $CF_{initial}$ can further be modified in accordance with certain factor (a) to produce a modified correction factor $C_{BG\_Analysis}$ in accordance with the formula: $CF_{BG\_Analysis} = aCF_{Initial}$ wherein factor (a) is defined as the factor of modification of $CF_{initial}$ (or a current Correction Factor). The below procedure can be performed with respect to sectioned data.

Factor (a) may be determined, according to the following procedure:

```
If T_hypo > 0 or T_ihypo > 1
    If (S_peak > S_min) and (S_peak > UpperLimit)
        a = (S_peak − S_min)/ (S_peak − UpperLimit);
    Else
        a = UpperLimit/S_min;
    End
Else
``` wherein $T_{hypo}$ is a percent of time spent in a defined hypoglycemia range during the relevant period/section; $T_{ihypo}$ is a percent of time spent in defined impending hypoglycemia range during the relevant period; $S_{min}$ is a minimum sensor reading during the relevant period; $S_{mean}$ is the average sensor readings during the relevant period; $S_{max}$ is a maximum sensor reading during the relevant period; $S_{peak}$ is a maximum sensor level in time range of up to three hours before the $S_{min}$ time, during the relevant period/section; UpperLimit is the lowest blood glucose reading that is recorded neither during impending hypoglycemia nor hypoglycemia; Sn_low is the lower boundary of "strict normal" glucose range (can be empirically defined as the glucose range in the range of about 80-120 mg/dl), which is typically set to be 80; Sn_high is the higher boundary of "strict normal" glucose range, which can be set to be 120; dN is the subtraction Sn_high−Sn_low.

A histogram (or alternatively, a distribution function) can be determined by using the measured glucose levels of the treated patient. The histogram is a function representing occurrences of each measured glucose level of the patient during a certain time window or section. Parameter P can be defined as the summation of the occurrences (or an accumulated measured glucose levels) at an interval of a specific width (dN representing glucose measurement interval), wherein v is the initial glucose reading in the specific window, individualized for the treated patient.

val=arg $max_v$ {P(v,v+dN)}, where P(v,v+dN) is the percentage of glucose readings with the range [v,v+dN]; arg-$max_v$, means determining the v where P reaches maximum value.

Factor (a) may be thus determined as follows:

$$a = 0.57 \cdot a\_Tsn + 0.28 \cdot a\_Hyper + 0.15 \cdot a\_Mean$$

where $a_{13}$ Tsn=sn_low/val; $a_{13}$ Hyper=180/Smax; typically defined empirically; and $a_{13}$ Mean=110/Smean; typically defined empirically; W=[0.57 0.28 0.15], is a weighing vector/coefficients, typically defined empirically.
End The person skilled in the art would appreciate that the weighing vector can be adjusted or modified to suit particular insulin treatments. In some embodiments, a histogram representing the occurrence of measured glucose level of the patient during a certain time window can thus be determined. The local maximum (or peak) in a glucose measurement interval can then be obtained, for example by maximizing the function P(v,v+dN) as exemplified above.

In some embodiments, final CF is calculated as one or as a weighted average of the above calculated CF values (i.e. $CF_{from\_MS}$, $CF_{non\_mcal}$, $CF_{BG\_Analysis}$) with majority similar trend. In this respect, similar trend means that all CFs values recommend either increasing or decreasing the value of the CF compared to the current patient's CF. In some embodiments, final CF is calculated as one or as a weighted average of the above calculated positive CF values. In some embodiments, final CF is calculated as one or as a weighted average of the above calculated CF values which determine increase of the CF. In some embodiments, final CF is calculated as one or as a weighted average of the above calculated CF values which determine decrease of the CF.

Settings the Glucose Targets

In some embodiments, the above described technique of the invention utilizes the glucose ranges presented below which have been arrived empirically.

TABLE 2

| High | Low | Hours | Pump target settings Age Group [Years] |
|------|-----|-------|----------------------------------------|
| 150  | 110 | 00:00-19:00 | 0-6 |
| 150  | 150 | 19:00-00:00 |     |
| 120  | 100 | 00:00-20:00 | 6-12 |
| 150  | 150 | 20:00-00:00 |     |
| 110  | 90  | 00:00-21:00 | 12-19 |
| 130  | 130 | 21:00-00:00 |     |
| 100  | 90  | 00:00-22:00 | Adult (19+) |
| 120  | 120 | 22:00-00:00 |     |

Table 2 represents general clinical guidelines for treated patients pump settings using the technique of the present invention.

In some embodiments, the present invention relates to an CF module; the CF module is configured and operable to perform the procedures for unsupervised learning of correction factor (CF); the CF module is configured and operable to analyze MS being provided as input; the input is processed to produce output signal indicative of global insulin pump settings of correction factor (CF) parameter. In some embodiments, the CF module is configured and operable to analyze BS being provided as input; the input is processed to produce output signal indicative of global insulin pump settings of correction factor (CF) parameter. In some embodiments, the CF module is configured and operable to analyze BS and MS both being provided as input; the input is processed to produce output signal indicative of global insulin pump settings of correction factor (CF) parameter.

Monitoring System

Figure 9:
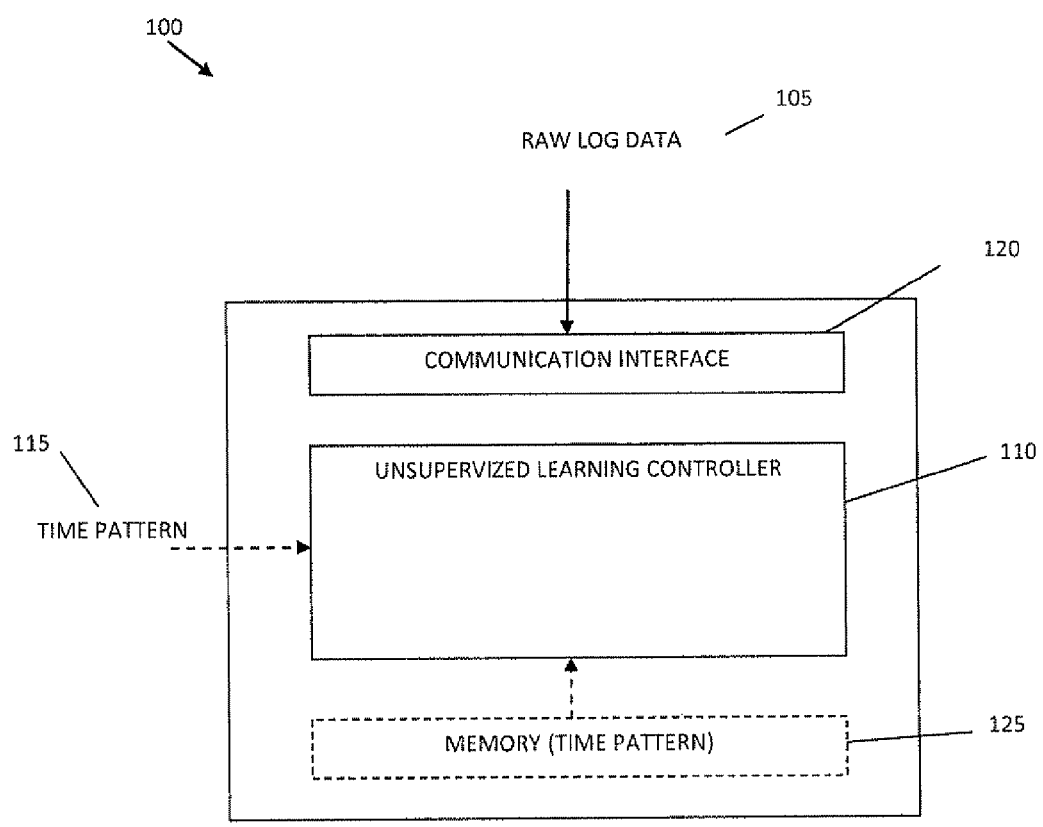
FIG. 9 is a schematic block diagram illustrating in a non-limiting manner the component a device (or system) for monitoring a diabetic treatment of a diabetic patient.

Reference is made to FIG. 9 which is a schematic block diagram illustrating a non-limiting example of a monitoring system (or device) 100 in accordance with one embodiment of the present invention. The device 100 is typically processor-based and includes inter alia a memory utility 125, data input and output utilities (not shown), and a data processor utility. The latter is configured as or comprises as a part thereof an unsupervised learning controller 110 of the invention which provides retrospective analysis of raw log data 105, which is input into the device 100 while in a machine readable format, via a communication interface 120. The input to the controller 110 is unsupervised input, and the controller calculates the global insulin pump settings from the unsupervised input i.e. raw data input.

The communication interface 120 is appropriately configured for connecting the to processor utility 110, via wires or wireless signal transmission (e.g. via communication network(s)), to either a measurement device supplying the raw log data or to an external memory (database) where such raw log data have been previously stored (being supplied to from measurement device(s)), In some embodiments, the raw log data 105 includes one of glucose sensor reading/levels as a function of time, meal event data as a function of time, and insulin delivery data as a function of time. Therefore, the raw log data 105 can be in the form of time space data points.

The raw log data 105, in some embodiments, adheres to or is in the form of a predetermined time pattern 125. The time pattern 125 typically comprises plurality of timestamps. A timestamp, as described herein, is a string or other object which is used to connote time such as day, hour, minutes etc' along a certain time window. The plurality of timestamps is used to obtain raw log data 105 including items corresponding to the time pattern 125. By way of a non-limiting example, raw log data of basal rate can take the form of <time stamp, basal rate> or <a period of time/time slot, basal rate>. Raw log data 105 of insulin delivery can be provided in the form of <time stamp, insulin dose>. Raw log data 105 of meal event can be provided in the form of <time stamp, COH consumed>. The person skilled in the art would appreciate that there are variety of ways to encode such information and the particular encoding regime can be determined for such purpose. In some embodiments, raw log data 105 adheres to a predetermined time pattern 115 which is externally provided i.e. being communicated to the device 100 by wired or wireless means.

The learning controller of device 100 can perform procedures and analysis without human supervision of cooperation. In this connection, it should be understood that the unsupervised learning controller of device 100 can calculate the global insulin pump settings from input raw log data and not from manually input data by a user (touch pad or key pad input). In other words, the system of the invention can be configured for automatic or semi-automatic operation via direct contact with the data records where the raw log data can be accessed. The calculation procedure does not include variable assignment(s) of manual input queries or responses to queries from users to the controller (patient or physician). In some embodiments, the unsupervised learning controller of device 100 calculates the global insulin pump settings during one continuous time window which is initiated at acquiring the raw log data and terminates after calculating any of the global insulin pump settings i.e. not enabling interruptions (e.g. asynchronous) for obtaining user input to the controller during the calculation procedure.

The unsupervised learning controller is configured and operable to receive and process said raw log data, to determine an informative data piece from residual log data portion of said raw log data and select said informative data piece for retrospectively analyzing and calculating at least one of basal rate or basal plan, correction factor (CF), carbohydrate ratio (CR) and insulin activity curve parameters and generate an update for insulin pump settings.

In some embodiments, the device 100 is used for diabetic treatment management and comprising a communication interface 120 configured and operable to permit access to stored data being time spaced data points of glucose measurements, meals consumed and insulin delivery. The device 100 further includes a control unit comprising a data processor utility or processor 110 for providing retrospective analysis of said data and determining at least one global insulin pump setting of basal rate (or basal plan), correction factor (CF), carbohydrate ratio (CR) and insulin activity curve parameters, wherein said processor utility is operable to determine each of said parameters by processing a data piece of said received data corresponding to a selected time slot of said certain period of time. The manner of obtaining data corresponding to a selected time was already referred to above with regard to Initial Data Analysis and Sectioning.

The analysis being performed by the unsupervised controller can thus include sectioning the stored data or the raw log data input, thus, obtaining stored data within a predetermined time window. Where the predetermined time window is a Basal data Section (BaS), the calculated insulin pump settings being selected is basal rate or basal plan. Where said predetermined time window is a Meals data Section (MS) the calculated insulin pump settings being selected from being Active Insulin Function (AIF), correction factor (CF) or carbohydrate ratio (CR). In case, the predetermined time window is a Bolus data Section (BS) the calculated insulin pump settings being selected from correction factor (CF) or Active Insulin Function (AIF).

In some embodiments, the system (or device) 100 or the unsupervised learning controller 110 is configured and operable to perform at least one of the unsupervised learning retrospective analysis procedures or methods, for example, those of methods 200, 300, 400, 500 or 600. The unsupervised learning procedures should be understood as those which determine insulin pump settings from raw log data as defined above without human participation during analysis which arrives to the final calculation. The unsupervised learning controller 100 merely requires raw data being accumulated during the everyday routine activities of the treated patient without any special procedural requirement. In this respect, raw log data is log recordation being performed during regular routine activity of the patient irrespective of any assumed testing or other premeditated assumption relating to the specific patient or physician (i.e. a unsupervised controller permitting analysis of user independent procedure/method or with a user cooperation/participation).

A computer program is also provided optionally recordable on a storage medium and comprising a machine readable format, the computer program being configured and operable to, when being accesses, carry out at least one of the unsupervised learning retrospective analysis procedures or methods, for example, those of methods 200, 300, 400, 500 or 600. In some embodiments, the computer program is being configured and operable to carry out identifying raw log data input corresponding to a certain time period and comprising glucose measurements, meals events and insulin delivery; determining an informative data piece and residual log data portion of said raw log data; selecting said informative data piece and calculating therefrom at least one of basal rate, correction factor (CF), carbohydrate ratio (CR) and insulin activity curve parameters, and generating output data comprising values for global insulin pump settings The terms processor module and micro/processor unit are used herein interchangeably, and furthermore refer to a computer system, state machine, processor, or the like designed to perform arithmetic or logic operations using logic circuitry that responds to and processes the instructions and that drive a computer.

In one embodiment, the device is an insulin pump. In some embodiments, the device provides a close-loop insulin management for the user. The unsupervised control unit automatically can determine the insulin pump settings such as at least one of basal rate (or basal plan), correction factor (CF), carbohydrate ratio (CR) and insulin activity curve parameters.

The techniques and system of the present invention can find applicability in variety of computing or processing environments such a computer or a process based environments.

The techniques may be implemented in a combination of the software and hardware. The techniques may be implemented in programs executing on programmable machines such as stationary computers being configured to obtain raw log data as also been described above. The techniques may be implemented by similar devices that include a processor, a storage medium readable by the processor, at least one input device to manage raw log data, and one or more output devices to determine of insulin pump settings. Program code is applied to the data entered using the input device to perform the techniques described and to generate the output information. The output information can then be applied to one or more output devices.

Each program may be implemented in a high level procedural or object oriented programming language to communicate with a processed based system. However, the programs can be implemented in assembly or machine language, if desired.

In other embodiments, the methods and systems of the present invention can be utilized over a network computing system and/or environment. Number of computer systems could be coupled together via a network, such as a local area network (LAN), a wide area network (WAN) or the interne. Each method or techniques of the present invention such as that of 200, 300, 400, 500 or 600 as a whole or a functional step thereof could be thus implemented by a remote network computer or a combination of several. Thus, any functional part of system 100 can be provided or connected via a computer network. By way of non-limiting example, the system may be remote to provide the insulin pump settings over the network optionally to a network user. In addition, the unsupervised processor module can also be remotely providing the processor services over a network. In this respect, service relates to such as that of methods 200, 300, 400, 500 or 600.

In some embodiments, the system (or device) 100 include the sectioning module. In some embodiments, the unsupervised learning controller 110 comprises the sectioning module.

In some embodiments, the system (or device) 100 include the basal plan module. In some embodiments, the unsupervised learning controller 110 comprises the basal plan module.

In some embodiments, the system (or device) 100 include the carbohydrate ratio module. In some embodiments, the unsupervised learning controller 110 comprises the carbohydrate ratio module.

In some embodiments, the system (or device) 100 include the AIF module. In some embodiments, the unsupervised learning controller 110 comprises the AIF module.

In some embodiments, the system (or device) 100 include the CF module. In some embodiments, the unsupervised learning controller 110 comprises the CF module.

In one embodiment, a monitoring system for use with diabetic treatment management is provided such that it is deployed on a network computer such as a server which permits communication with user across the network. The monitoring system includes a communication interface configured and operable to permit access to stored raw log data obtained over a certain time and being indicative of glucose measurements, meals events and insulin delivery. The raw log data input can thus be communicated to the server over the network. This can take the form of uploading the entire or part of raw log data input to the monitoring system. The system further includes a control unit comprising an unsupervised learning controller (or module) configured and operable to receive and process said raw log data, to determine an informative data piece from residual log data portion of said raw log data and select said informative data piece for processing to determine at least one of basal rate (or basal plan), correction factor (CF), carbohydrate ratio (CR) and insulin activity curve parameters and generate an update for insulin pump settings.

Each such program may be stored on a storage medium or device, e.g., compact disc read only memory (CD-ROM), hard disk, magnetic diskette, or similar medium or device, that is readable by a general or special purpose programmable machine for configuring and operating the machine when the storage medium or device is read by the computer to perform the procedures described in this document. The system may also be implemented as a machine-readable storage medium, configured with a program, where the storage medium so configured causes a machine to operate in a specific and predefined manner.

Referring now to the following figures, there are described embodiments of the present invention, relating to a monitoring system which includes the control unit of the system 100 described above, as well as additional components for additional processing of other relevant data. Such components receive the output of the system 100 and are configured for generating a treatment recommendation accordingly. The treatment recommendation may be either sent automatically to the insulin pump 24 or may be presented to an authorized person (e.g. a physician or the patient) through a user interface for choosing whether to apply the treatment recommendation or not.

Figure 15:
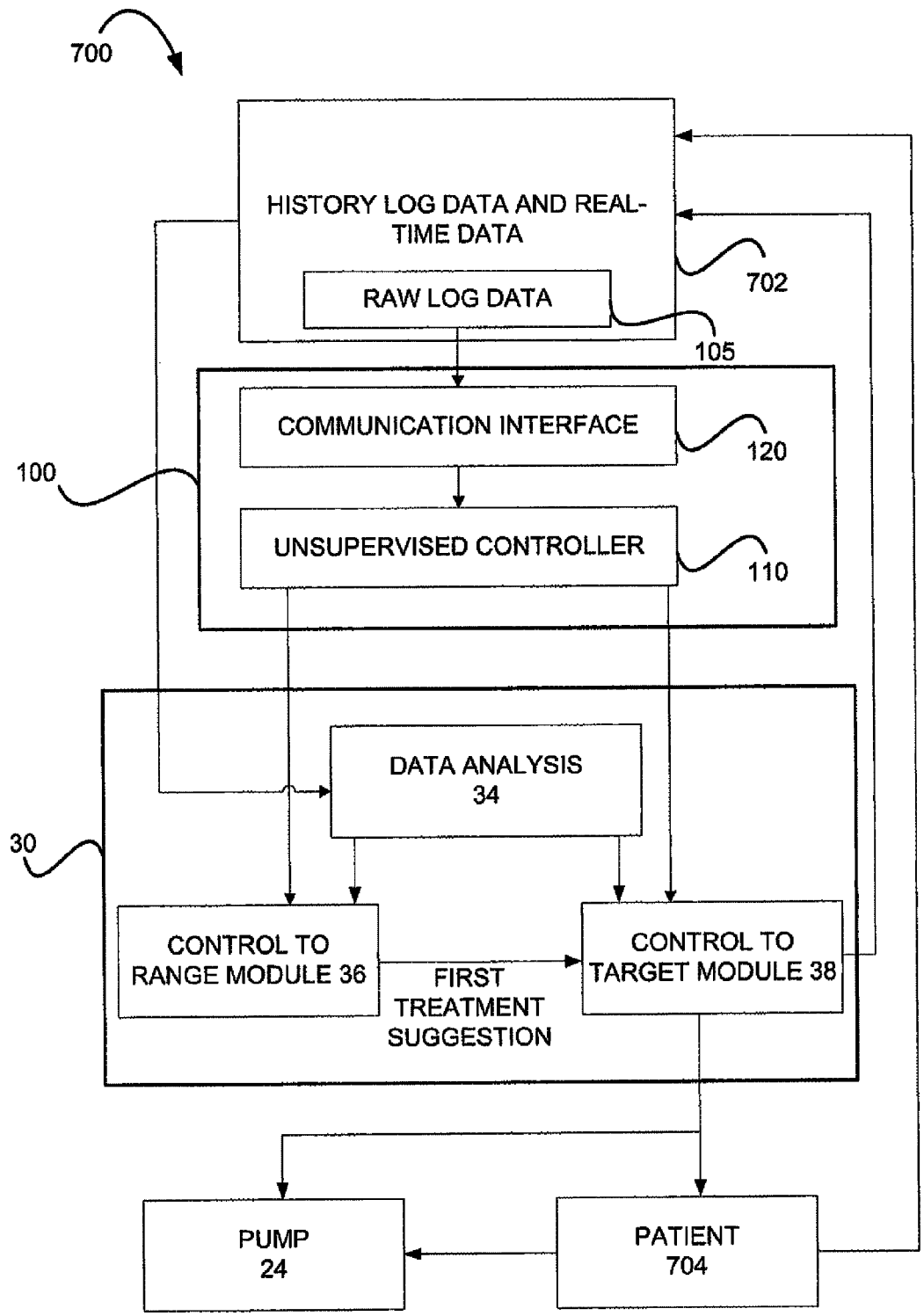
FIG. 15 is a schematic diagram of an embodiment of the present invention utilizing a monitoring system configured for generating a treatment recommendation, and communicating the treatment recommendation either to the pump or to an authorized user (such as a patient)

Referring to FIG. 15, a non limiting example of another embodiment of a monitoring system 700 is shown. The global insulin pump settings are determined by the procedure described above, based on Raw log data 105 that is sent to the unsupervised learning controller 110 via the communication interface 120, and processed by the unsupervised learning controller 110.

In addition to the global insulin pump settings, other relevant data stored in a memory utility 702 (denoted as history log data and real-time data 702) is entered together with the global pump settings into further processing in the additional processing unit (software/hardware utility) 30. The other relevant data comprises reference data, including individualized patient's profile related data, and individualized patient's treatment history related data, such as insulin sensitivity, glucagon sensitivity, insulin/glucagon pharmacokinetics associated data, and glucose target level or target range level. The processing unit 30 comprises a first processor module 34 (referred in the figure as Data Analysis), and a second processor module 36, herein also denoted as control to range module (CRM).

The first processor module 34 is configured for processing measured data indicative of blood glucose level and generating first processed data indicative thereof. The second processor module comprises a fuzzy logic module; the fuzzy logic module receives input parameters corresponding to the measured data (data measured in real time, optionally stored in the memory utility 702), the first processed data (data processed by the data analysis module 34) and the reference data (including the global pump settings data from the unsupervised controller 110). The fuzzy logic module then processes the received parameters to produce at least one qualitative output parameter indicative of patient's treatment parameters, which in some embodiments can be a first treatment suggestion followed by more processing. The processing unit 30 may also include a control to target module (CTM) 38 for final determining whether any of the patient's conditions/treatment is to be modified. As explained above, the final output is may be sent directly and automatically to the pump 24 or the drug injection device, or can be presented as a recommendation, through a suitable user interface, visually, audibly or else, to let the user (e.g., a patient 704 or a medical professional) decide whether to accept and apply the recommendation or not.

Measured blood glucose (13G) level from a measurement device (either directly measured or predicted from measured tissue glucose level, as the case may be) enters the processing unit 30.

The second processor 36 receives quantitative input parameters corresponding to the measured data, the first processed data and the reference data (including the global pump settings data), and processes the received quantitative parameters to produce qualitative output parameters indicative of patient's conditions and enabling to determine whether any of these conditions is to be modified, Output of the data analysis module 34 (first processed data) is processed by the fuzzy module of the second processor 36. The qualitative output parameters of the fuzzy logic module 36 are then processed by a third processor module which can be also denoted as the CTM 38 to determine whether any of the patient's conditions/treatment is to be modified. The final decision relating data from module 38 may be used for updating reference data in the memory utility 702.

Measured data may also include special event, such as meals, physical activity, sleep time etc.

Figure 16:
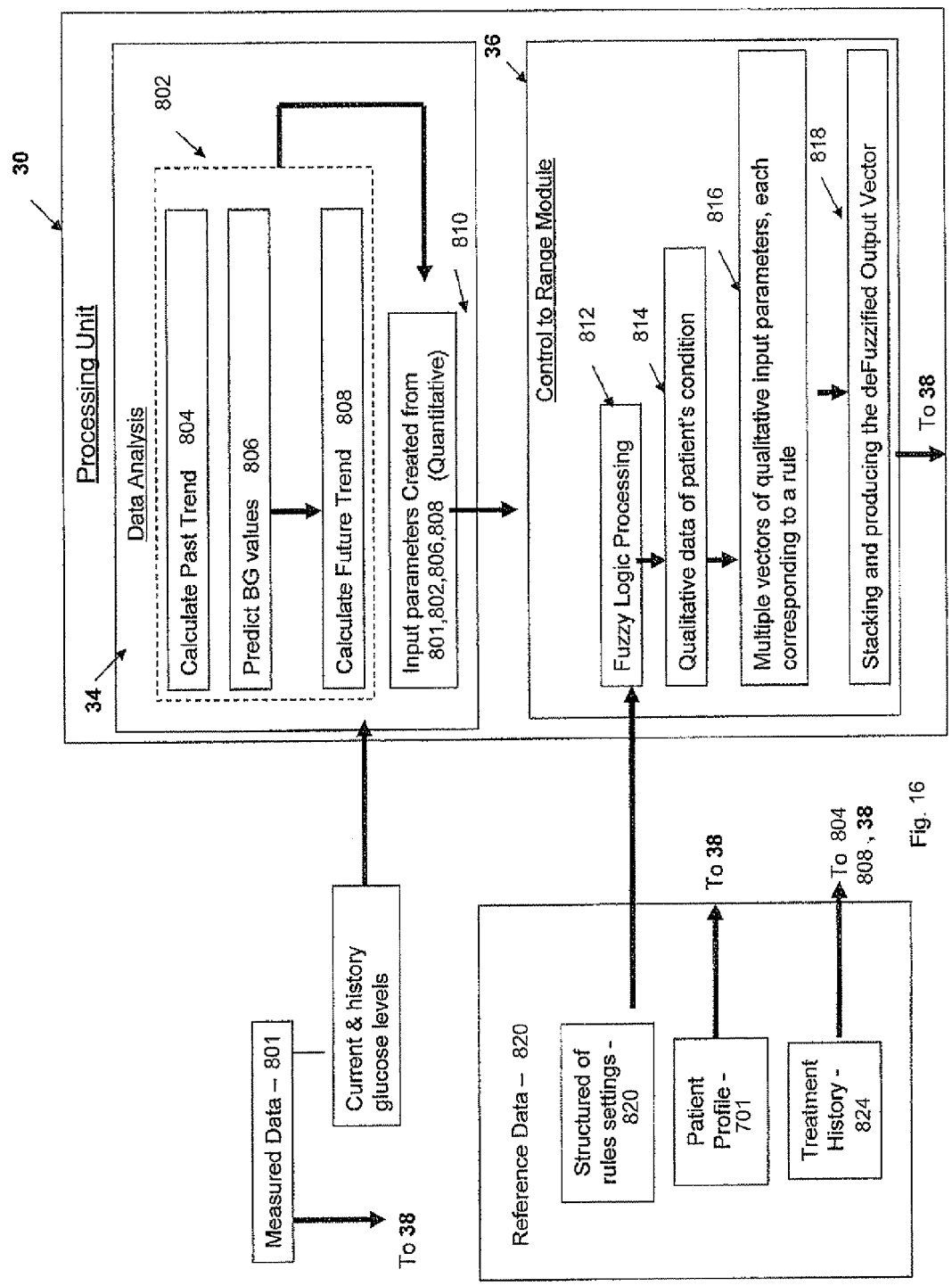
FIG. 16 is a flow diagram of a method of the present invention for monitoring diabetes treatment of a patient and generating a treatment recommendation.
Figure 16:
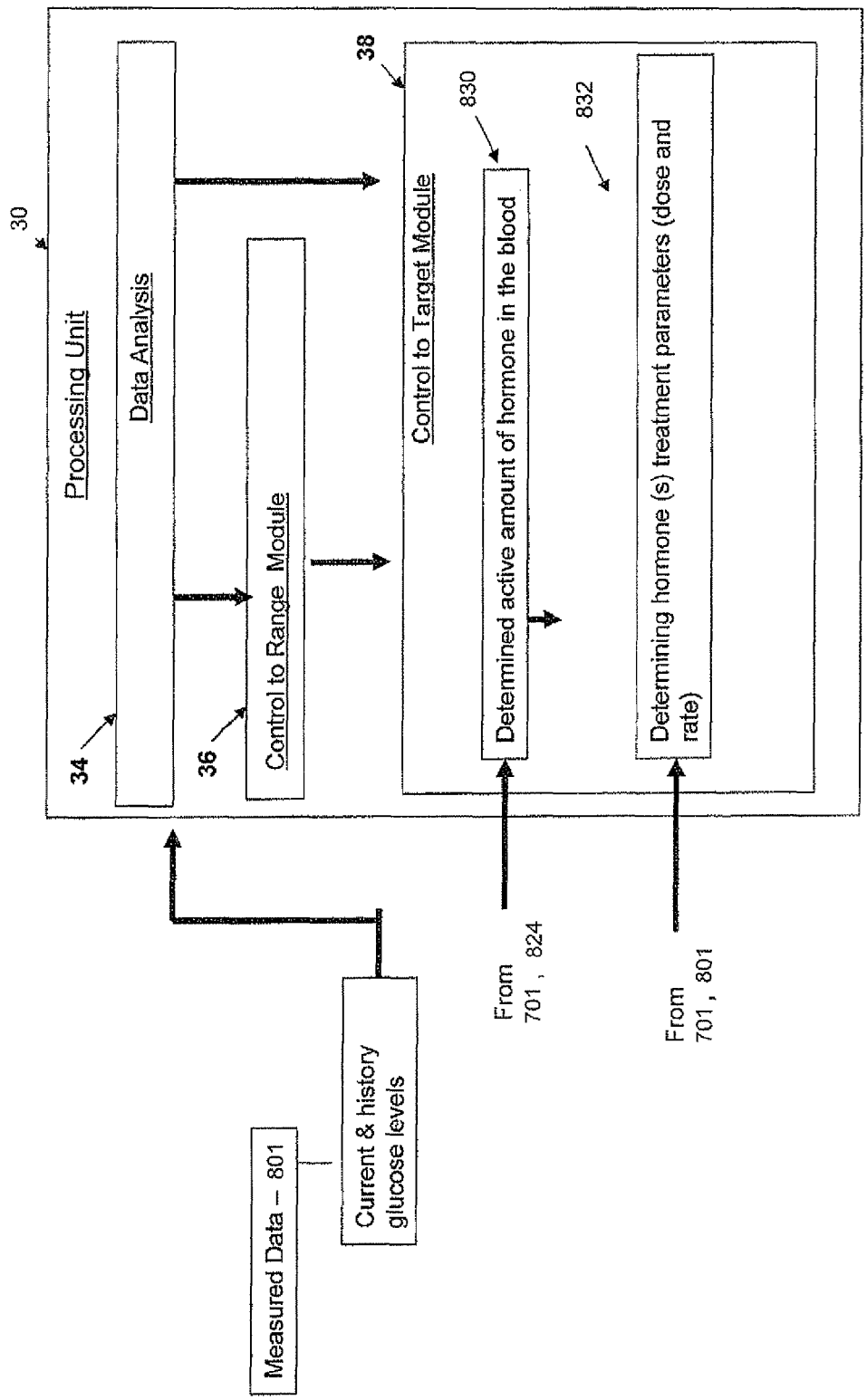

Reference is now made to FIG. 16 exemplifying a flow diagram of a method of the present invention for automatic monitoring of diabetes-related treatment. FIG. 16 particularly relates to the operation of the processing unit 30. Generally, the method comprises analyzing data generated by at least one of drug delivery devices and glucose measurement devices; identifying patient's conditions; and deciding about treatment modification by controlling the operation of the drug injection devices to enable real-time automatic individualized monitoring of the treatment procedure.

In some embodiments, analyzing the data comprises providing reference data (step 820). The reference data includes patient's profile related data 701; treatment history related data 824, and a structure of rules or "table of rules" settings 822. The structure of rules settings are based on the physician approach of evaluating the measurements. The patient's profile related data 701 includes a set of parameters (and calibratable or updatable during the monitoring procedure or during the treatment) about the patient's condition. The patient profile related data 701 is extracted from collecting data several days prior to connecting the patient to the monitoring system, and includes the global pump settings data from the unsupervised controller 110.

In some embodiments, the set of parameters is automatically modified by a learning algorithm.

In some embodiments, the treatment modification comprises at least one of the followings: controlling an individualized basal plan; controlling patient specific insulin sensitivity for glucose levels (referred as a "correction factor") indicative of the correction of the current blood glucose level to a target level and of the amount of insulin/and or glucagon to be delivered; controlling the individualized blood glucose target level; controlling the insulin and/or glucagon pharmacokinetics settings to determine the sensitivity of each patient to insulin and/or glucagon respectively.

More specifically, at least one of the followings conditions is controlled:

(1) Basal Plan: The rate of insulin to be injected to the patient during an entire day, according to the time of the day. For example, type 1 patient receives a continuous dose of insulin during the day. This dose can be changed during the day, depending on the change in the patient sensitivity to insulin. Basal Plan can be represented as a series of individualized basal treatment rates as a function of time. The role of the basal treatment is to treat with the endogenic release of glucose by the liver. Therefore, an optimal basal plan will keep the glucose levels stable.

(2) Correction Factor (CF) Insulin/Glucagon Plan: The following equation (1) is used to correct the current BG level to the target level (defined as a reference level for Insulin/glucagon calculation) and to calculate the Insulin/Glucagon bolus:

$$CorrectionBolus(\text{Insulin}/\text{Glucagon}) = \frac{\text{abs}(CurrentBG - \text{Target})}{CF} \quad (1)$$

Due to the change insensitivity to Insulin/Glucagon, the CF can be set for each hormone according to the time of the day.

(3) BG Target—The blood glucose level target is defined per patient as a reference level to be used for example for the correction of the Insulin/Glucagon bolus.

(4) Insulin/Glucagon Pharmacokinetics (PK) Settings: A precaution curve is developed to determine the sensitivity of each patient to Insulin/Glucagon, as will be detailed below.

(5) Optionally, the structure of rules settings of the fuzzy logic module such as categorized blood levels (e.g. very low, low, normal, normal high, high and very high) to as will be detailed below.

Turning back to FIG. 16, the measured data 801 (being a part of the data 702 of FIG. 15) is indicative of the BG level at a certain period of time, being directly measured in the blood or the subcutaneous tissue.

The analyzing of the data is carried out by processing measured data 801 in the data analysis 34 and generating first processed data indicative thereof (step 802). A fuzzy logic model is applied (step 812) to quantitative input parameters (step 810) corresponding to the measured data 801, the first processed data by using a structure of rules settings to produce qualitative output parameters indicative of patient's conditions.

In some embodiments, processing of the measured data (step 802) includes calculation of a past trend in a glucose level change (step 804), predict the future BG level value (step 806), and using the prediction results to calculate a future trend (step 808).

In this connection, it should be understood that the glucose past/future trend is a parameter influenced by three factors: (i) the average rate of change in the glucose level in mg/dl per minute in a certain time window (i.e. the average rate of change), (ii) the course of change (i.e. ascending or descending) and (iii) the duration of this course.

The quantitative input is a vector of parameters supplied from the measured data relating modules 801, 804, 806 and 808.

For example, the quantitative input include the followings four parameters: the past trend, the future trend, the current BO level and the predicted level of the BG.

The fuzzy logic processing 812 is utilized to transform, using the structured of rules settings, the quantitative input vector to qualitative output vector (e.g. multiple vector) (step 814) denoted as Fuzzified input vectors indicative of the patient's condition. In some cases, multiple Fuzzified input vectors are obtained from the fuzzy logic processing and each Fuzzified input vector is associated with a matching rule (step 816) of the "table of rules" defined above. In these cases, each matching rule is assigned with a statistical agreement factor which describes to what degree each rule is applied. All applied rules are stacked according to their statistical agreement and a deFuzzy Function calculates the deFuzzified Output Vector (step 818) which includes the fuzzy logic recommendation to changes in the treatment in percentages.

For example, the following input vector: [0.7 110 2 170] is interpreted as follows: in the last 20 minutes, the trend was 0.7 [mg/dl/min], the current blood glucose level is 110 [mg/dl], the predicted trend of the blood glucose level is 2 [mg/dl/min] and the predicted value in the 30 minutes is 170 [mg/dl]. When this input vector goes through the fuzzy logic module of the CRM 36, it is translated to the following Fuzzified input vectors:
1. [High Normal VeryHigh NormalHigh]
2. [High Normal VeryHigh High]

These Fuzzified Input Vectors match rule number 73 (73% agreement) and rule number 204 (27% agreement). Both of these rules outputs take into consideration and their output member functions be stacked according to their weight (i.e. their statistical agreement percent).

The deFuzzy Function calculates the center of weight of those stacked functions (for each of the outputs separately) to weight all the relevant rules and gives the following deFuzzified Output Vector: [50 2.59 0]

Generally, each rule includes a modification of the current treatment delivered to the patient, adapted to a specific patient condition indicated by the Fuzzified input vector. As described above, the treatment parameters (i.e. deFuzzified output vector) include at least one of the following parameters: the modification of the basal rate and/or the insulin glucagon bolus percentage. Each rule is also associated with a contribution factor (weight) which designates the likelihood of the patient's condition being associated with the specific rule. More specifically, the weight is the probability of such rule to occur in real life, quantized to a number between 04. The weight can also be determined in accordance with the importance assigned to the rule. In addition, the weight may also be in accordance with a special event handled by the fuzzy logic engine.

The initial recommendation received from the CRM 34 is in percentage. To determine the dosing amount of the two outputs in units or units/hour, the CTM 36 considers the recommendation of the CRM 34 as well as the glucose target level. Special glucose dynamics analysis is then applied, assuming the dosing regimen history and safety constraints related to the insulin pharmacodynamics, and amount of glucagon and/or insulin active to yield the final dosing recommendation.

Figure 17:
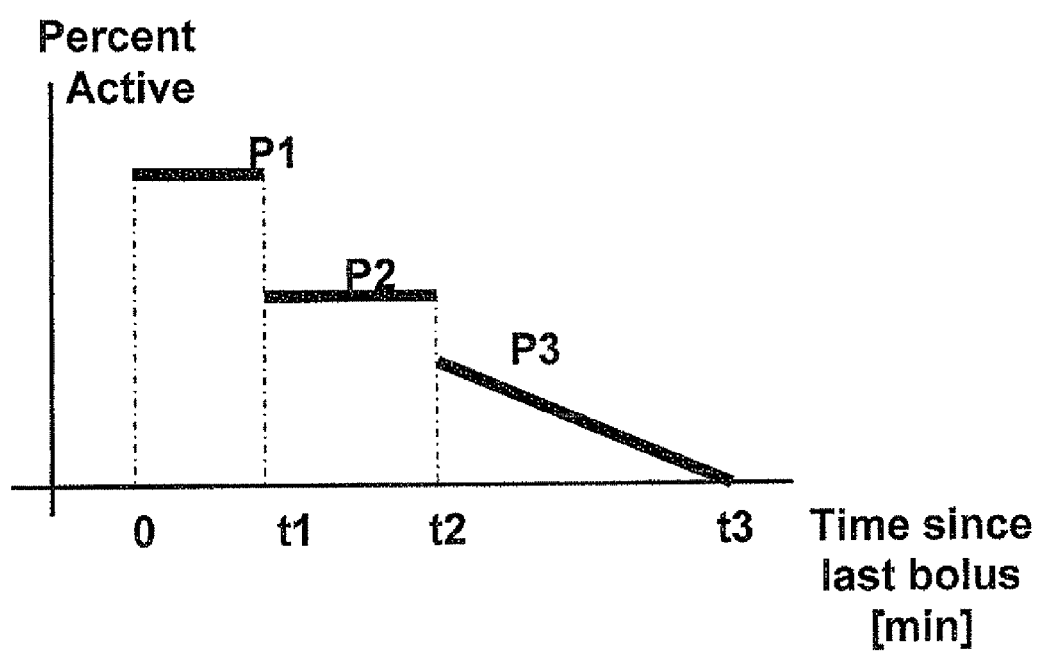
FIG. 17 is a graph illustrating the percentage of insulin active in the blood after a bolus injection.

The current amount of glucagon and/or insulin active ($G_{active}$, $I_{active}$) section in the blood is determined according to the patient's profile 701 (step 830), as exemplified in FIG. 17, illustrating the precaution curve determining the pharmacodynamics of a to patient to insulin/glucagon. This curve is indicative of the percentage of the insulin/glucagon "active" in the blood at a certain time after the delivery of the insulin/glucagon bolus. The present invention therefore provides a system for use in monitoring diabetes treatment of a patient, the system is configured and operable to modify or provide a treatment (i.e. insulin/glucagons bolus or basal treatment) in accordance to the insulin/glucagons pharmacodynamics of the treated patient. In some embodiments, insulin/glucagons pharmacodynamics is represented by a curve or a function describing the percentage (or otherwise amount) of the insulin/glucagon "active" in the blood at a certain time after the delivery of the insulin/glucagon bolus. Moreover, the present invention also provides a method for use in monitoring diabetes treatment of a patient. The method comprises obtaining insulin/glucagons pharmacodynamics of the treated patient; and adjusting a treatment (i.e. insulin/glucagons bolus or basal treatment) in accordance to the insulin/glucagons pharmacodynamics of the treated patient.

The amount of insulin (e.g. percentage) present in the blood is represented at three different period of times (P1, P2, P3) characterizing the activity of the insulin since the last bolus injection. Similar graphs, specific to each patient, designating the patient's absorbance (i.e. decay rates) of insulin/glucagon after bolus or basal treatment, can be generally included in the patient's profile. These decays rates may be used together with the treatment history to determine the amount of active insulin/glucagon present in the blood.

The calculation of the active insulin and active glucagon is done by the CTM module 38 using insulin and glucagon treatment history 824 and the patient's individual pharmacodynamics of glucagon and insulin taken from the patient profile 701, as detailed above.

The calculation of the active glucagon at the current moment is performed as follows: The times and doses of glucagon are given, denoted as TG and VG, both vectors of size N. The current time is denoted by $t_0$. The active glucagon is denoted by $G_{active}$. The activity function of the glucagon $f_G(t)$ is determined by the patient individual settings:

$$f_G(t) = \begin{cases} P_1 & t \leq t_1 \\ P_2 & t_1 < t \leq t_2 \\ \frac{P_3(t-t_3)}{(t_3-t_2)} & t_2 < t \leq t_3 \\ 0 & t_3 < t \end{cases}$$

Where $t_{1-3}$, $P_{1-3}$ are Glucagon time constants which are individually set for each patient, and can be learned and updated automatically by a self-learning algorithm.

The active glucagon is calculated as follows:

$$G_{active} = \sum_{i=1}^{N} VG[i] \cdot f_G(t_0 - TG[i])$$

Similarly, the active insulin can also be calculated at the current moment:

The times and doses of insulin are given, denoted by TI and VI, both vectors of size K. The current time is denoted by $t_0$ The active insulin is denoted by $I_{active}$.

The activity function of the insulin $f_I(t)$ is determined by the patient individual settings:

$$f_I(t) = \begin{cases} P_4 & t \leq t_4 \\ P_5 & t_4 < t \leq t_5 \\ \frac{P_6(t-t_6)}{(t_6-t_5)} & t_5 < t \leq t_6 \\ 0 & t_6 < t \end{cases}$$

where $t_{4-6}$ $P_{4-6}$ are insulin time constants which are individually set for each patient, and can be learned and updated automatically by a learning algorithm.

$$I_{active} = \sum_{i=1}^{K} VI[i] \cdot f_I(t_0 - TI[i])$$

The active glucagon is calculated as:

The amounts of hormones (i.e. insulin and/or glucagon) to be delivered is determined (step 832) by the CTM module 38 based on the initial recommendation received from the fuzzy logic module 36 (in percentage unit), the patient's treatment history 824, the insulin/glucagon sensitivity (from the patient profile 701) and the amount of hormones active in the blood 830, for example as follows:

The fuzzy logic output vectors are indicative of $G_p$, $B_p$ and $Ba_p$ being the percentage recommendations for the Glucagon, Bolus Insulin and Basal Insulin respectively. ($G_p$ varies from 0 to 100 [%], $B_p$ varies from 0 to 100 [%] and $Ba_p$ varies from −100 to 100 [%]). The corresponding amounts of Glucagon, Bolus Insulin and Basal Insulin to be received by the drug delivery device are denoted as $G_a$, $B_a$ and $Ba_a$. S is the last sensor reading. $CF_G$ and $CF_I$ are the glucagon and bolus insulin sensitivity factors, which are a part of the patient's profile and set individually for each patient and can be learned in real-time. They are time-dependent and change for different times of the days to reflect natural changes in glucagon and/or insulin sensitivity.

GT is the patient individual glucose target level.

Basically the amount of glucagon and insulin dose treatment is defined respectively as follows:

$$G_s = \frac{S - GT}{CF_G} * G_p * 0.01 - G_{active},$$

$$B_s = \frac{S - GT}{CF_I} * B_p * 0.01 - I_{active}$$

$G_{active}$, $I_{active}$ being the active glucagon and insulin whose calculation was defined above. If $G_s$ is negative or $G_p$ is lower than 50%, $G_s$ is 0. If $B_s$ is negative, $B_s$ is 0.

Similarly, the basal treatment is defined as follows: $Ba_s = f_{BA} * (1 + 0.01 * Ba_p)$, $f_{BA}$ is the patient's basal plan indicative of the basal rate for each hour of the day. The function is defined in the patient's profile and can be defined individually for each patient. In addition, this function can be updated by a given data set indicative of the precedent modified treatments using the teachings of the present invention.

Determining the glucagon bolus, basal rate and the bolus treatment, recent treatments are taken into account. $t_G$ and $t_B$ are the time which passed since the last glucagon delivery and the last bolus insulin delivery, respectively. In case, there was no glucagon delivery or no bolus insulin delivery, $t_G = \infty$, and $t_B = \infty$. $t_0$ is the current time. The response time to glucagon/insulin absorption are the constant times $t_i$ determined by the activity time of the glucagon and insulin.

These are individual settings for each patient, for example as follows:

If $t_G \leq t_1$ $G_a = G_s, B_a = 0$ and $Ba_a = 0$

If $t_1 < t_G \leq t_2$ $G_a = G_s, B_a = 0$ and $Ba_a = Ba_s = 0$

If $t_3 < t_G$, the following approach has to be adopted: BT is the glucose level threshold which allows bolus delivery. FB is defined as the first bolus to be delivered typically having a relatively high value. SB is defined as the second bolus to be delivered typically having a lower value than FB.

FB is true if S>BT and $B_2$>0.5 and $t_B \leq t_4$. Otherwise FB is false.

SB is true if S>BT and $B_s$>0.25 and $t_B$>$t_4$. Otherwise FB is false.

If SB is true or FB is true then $G_a = 0$, $B_a = B_s$ and $Ba_a = Ba_s$. Otherwise $G_a = 0$, $B_a = 0$ and $Ba_a = Ba_s$.

Figure 18:
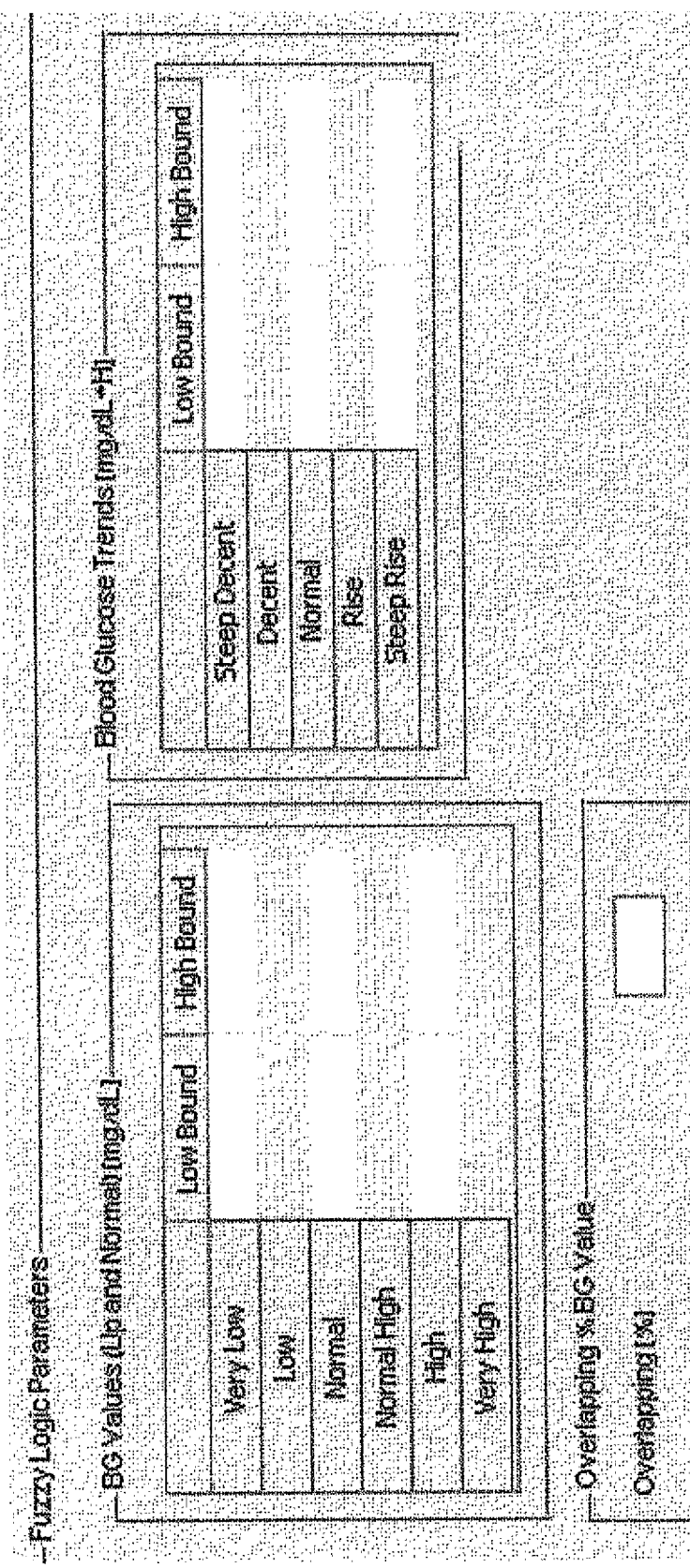
FIG. 18 exemplifies the parameters of the fuzzy logic module.

Reference is made to FIG. 18, illustrating the qualitative input parameters definition of the fuzzy-logic module 38. These parameters are individualized (i.e. adaptable to each patient) and they can be automatically changed by the control unit.

For example, the qualitative input parameters include fuzzy values of the BG values in mg/dL categorized in six levels (very low, low, normal, normal high, high and very high) and having a low bound and a high bound. The qualitative input parameters also include fuzzy trend of the BG trends in mg/dL/min categorized in five levels (Steep Descent, Descent, Normal, Rise and Steep Rise).

The first processor module 34 preprocess the measured data 801 to calculate trends in the glucose traces (past trend 804 and future trend 808) and predict the future glucose trace 808 in a certain horizon.

Trend of glucose level is determined as follows. Trend of glucose level can be determined in accordance with the average rate of change in glucose levels in a certain time window. The average rate of change in glucose level in a certain time window (Avg Ġ[$t_i$]), for example, can be calculated with a moving average method to determine the amplitude (to quantify the trend) and the course of the trend. The trend of glucose level can be used in turn to select a qualitative input parameter which suitably describes the trend as detailed herein. A trend of glucose level determined with respect to a time zone prior to a present time is denoted as past trend. Therefore, past trend can relate to a trend preceding a contemporary measured glucose level.

The trend duration factor can be employed to provide the trend a time measure of coefficient. The trend duration factor $\tau_{TD}$ can thus be defined as follows:

$$\tau_{TD} = \begin{cases} 1, 0 \leq T_{SLTC} \leq \tau_1 \\ 2\left(\frac{T_{SLTC} - \tau_1}{\tau_2}\right) + 1, \tau_1 < T_{SLTC} \leq \tau_3 \\ 3, T_{SLTC} > \tau_3 \end{cases} \quad (1.1)$$

where $T_{SLTC}$ [min] is the point in time when the glucose trend changes from descent to ascent or vice versa, and $\tau_i$ is a time constant. The trend parameter is defined as a function of Avg Ġ[$t_i$] and $\tau_{TD}$. For example, the trend parameter can be determined as follows: calculated trend=Avg Ġ[$t_i$]×$\tau_{TD}$.

For example, if the past BG levels in the past 20 minutes were BG=[153, 140, 137, 128, 120], and the time difference between each glucose reading is 5 minutes; the Avg Ġ[$t_i$] will be −1.33 mg/dl/min. Since this Avg Ġ[$t_i$] has a negative sign, it means the glucose levels are descending. For example, if the $T_{SLTC}$ is 45 minutes (i.e. the glucose levels are descending for 45 minutes) then $\tau_{TD}$ is 2. Thus, the calculated trend will be −2.66 mg/dl/min.

To predict future glucose levels, several prediction models may be used independently or as a combination with the monitoring technique of the present invention. The prediction models enable to overcome sensing and delivery delays. The predictor output is used by the fuzzy logic module.

As indicated above, the CRM 36 uses the reference data 820 and may be a Mamdani-type fuzzy logic controller with four inputs: past and future glucose trend (ḂG$_{Past}$ and ḂG̃$_{Future}$) as well as current and future glucose level (BG$_{Curr}$ and and BG̃Future). For example, a set of treatment rules was developed, with two outputs for each rule: (a) change in basal rate ($Ba_p$) and (b) portion of insulin bolus ($B_p$) (in percents from the patient's basal plan and the calculated bolus, respectively). To translate the clinical meaning of the input parameters using the fuzzy sets of rules, each member function for the input parameters had to have an interval in which the function's value is 1, followed by a smooth decrease to 0 outside this interval. Therefore, two-sided Gaussian curve member functions were selected. For the output parameters, Gaussian member functions were selected in order to prevent redundancy and to maintain the smooth transition between member functions.

The fuzzy rules were phrased in collaboration with the medical staff. The rules were designed to keep the glucose levels stable within the 80-120 mg/dl range. To evaluate the rule antecedents (i.e. the IF part of the rules), the AND fuzzy operation was used. The output (defuzzification) was calculated by a centroid method. The CRM output treatment suggestion was then transferred to the CTM 38.

By way of non-limiting examples, the fuzzy logic modules of the present invention can be implemented by using computerized engines such as MATLAB by MathWorks. Where exemplification relates to MATLAB, reference to member function (MF) shall refer to build-in member function provided therein.

The followings inputs are examples of the qualitative parameters that may be used in the fuzzy logic module of the present invention.

Input 1: past trend indicative of the calculated trend of the blood glucose level, based on data recorded by the sensor in the past 20 minutes.

Input 2: future trend indicative of the calculated trend of the blood glucose level for the next 30 minutes, based on the predicted data.

The past trend and future trend values are classified as follow:

Steep descent—The range is defined from −5 [mg/dl/min] to −2 [mg/dl/min]. The member function is defined as a Z-shaped function using the range borders −0.1/+0.1 respectively as the Z-Shaped function parameters.

Descent—The range is defined from −2 [mg/dl/min] to −0.5 [mg/dl/min].

The member function is defined as a Gauss2 function using the range borders +0.1/−0.1 respectively and 0.075 as the variance.

Stable—The range is defined from −0.5 [mg/dl/min] to +0.5 [mg/dl/min].

The member function is defined as a Gauss2 function using the range borders +0.1/−0.1 respectively and 0.075 as the variance.

Rise—The range is defined from +0.5 [mg/dl/min] to +2 [mg/dl/min].

The member function is defined as Gauss2 function using the range borders +0.1/−0.1 respectively and 0.075 as the variance.

Steep rise—The range is defined from +2 [mg/dl/min] to +5 [mg/dl/min].

The member function is defined as an S-Shaped function using the range borders +0.1/10.1 respectively as the S-Shaped function parameters.

The person skilled in the art would appreciate that the ranges and time interval can also be modified in accordance to a particular treatment to be envisaged.

Input 3: current blood glucose level indicative of the last blood glucose level recorded by the sensor.

Input 4: future level indicative of the predict blood glucose level in the next 30 minutes.

The current blood glucose level and the future level indicative of the blood glucose level are classified as follow:

Very Low—The range is defined from 50 [mg/dl] to 70 [mg/dl]

The member function is defined as a Z Shaped function.

Low—The range is defined from 70 [mg/dl] to 90 [mg/dl]

The member function is defined as a Gauss2 function.

Normal—The range is defined from 90 [mg/dl] to 140 [mg/dl]

The member function is defined as a Gauss2 function.

Normal High—The range is defined from 140 [mg/dl] to 170 [mg/dl]

The member function is defined as a Gauss2 function.

High—The range is defined from 170 [mg/dl] to 250 [mg/dl]

The member function is defined as a Gauss2 function.

Very High—The range is defined from 250 [mg/dl] to 500 [mg/dl]

The member function is defined as an S Shaped function.

All the parameters (S-Shaped and Z-Shaped functions parameters, Expectancy and Variance for the Gauss2 functions) for the member functions are calculated to meet the following rules: (1) the S-Shaped and Z-Shaped functions have to meet at y=0.5; and (2) S-Shaped and Z-Shaped functions have 5% of overlapping.

The person skilled in the art would appreciate that the ranges and time interval can also be modified in accordance to a particular treatment to be envisaged. The followings outputs are examples of the qualitative output parameters:

Output 1: Percentage of change of basal rate i.e. basal rate indicative of the recommended change, in percents relatively to the default contemporary basal rate (0%), in the delivered basal rate. The percent change can be between −100% (stopping insulin delivery) to 100% (double the default contemporary basal rate). This range can be quantized into equally separated steps.

Output 2: Percentage of bolus indicative of the suggested percent of the calculated insulin bolus. The percent change can be between 0% (No bolus) to 100% (All bolus). This range can be quantized into equally separated steps wise ranges.

Output 3: Optionally, glucagon indicative of the suggested percent of the calculated glucagon. The percent change can be between 0% (No Glucagon) to 100% (All Glucagon). This range can be quantized into equally separated steps wise ranges.

The number of input may be from one to four inputs and the number of outputs may be from one to three outputs.

The structures set of rules can comprise a combination of treatment strategies that can be modified according to each treatment procedure. The strategies may for example overlap while other strategies may be independent from each other. These strategies are represented by a certain relationship between the qualitative input parameters and the corresponding output parameters. The monitoring system of the present invention can determine which appropriate set of rules (appropriate number and combination) can be used to suggest optimal output parameter(s).

For example, the set of rules includes 96 rules, such as:

Rule #7: If the Current Blood Glucose Level is Low than do not give any bolus;

Rule #22: If Current Blood Glucose Level is Normal and the Future Trend of Blood Glucose is Descent than decrease the basal rate by 60%;

Rule #28: If the Current Blood Glucose Level is Normal than do not change the basal rate;

Rule #53: If the Current Blood Glucose Level is Normal-High and the Predicted Blood Glucose Level is at NormalHigh than increase the basal rate by 60%;

Rule #55: If Past Trend of Blood Glucose is Not Descending, the Current Blood Glucose Level is at NormalHigh, the Future Trend of Blood Glucose is Stable and the Predicted Blood Glucose Level is AboveNormal than give 50% of the suggested bolus.

Generally, each rule includes a relationship (e.g. modification) between the current specific patient's condition deduced from the values of the input parameters and the appropriate treatment to be delivered to the patient. In particular, the rules can define a relationship between qualitative parameters and a suggested treatment to the patient. For example, the rule can provide relationship between past traces or patterns of glucose measurements to the appropriate treatment. In another example, rule can provide relationship between predicted traces or patterns of glucose measurements to the appropriate treatment. The appropriate treatment can accommodate bringing the range of measured glucose level to a desired range. The patterns or traces (past or predicted) can be represented by a calculated trend. In respect, glucose traces or patterns can be represented by a series of glucose measurements each obtained at a certain time. Thus, glucose traces or patterns can also be represented by at least two glucose measurements obtain at a time interval. Predicted trends can be deduced from the past traces or patterns i.e. past traces or patterns can be used to determine a predicted traces or patterns. Such determination is typically performed by employing a prediction model, some of which are known in the art. Moreover, one element (a glucose level) of a predicted trace or pattern can be selected to be the predicted blood glucose level or a future level.

Figure 19:
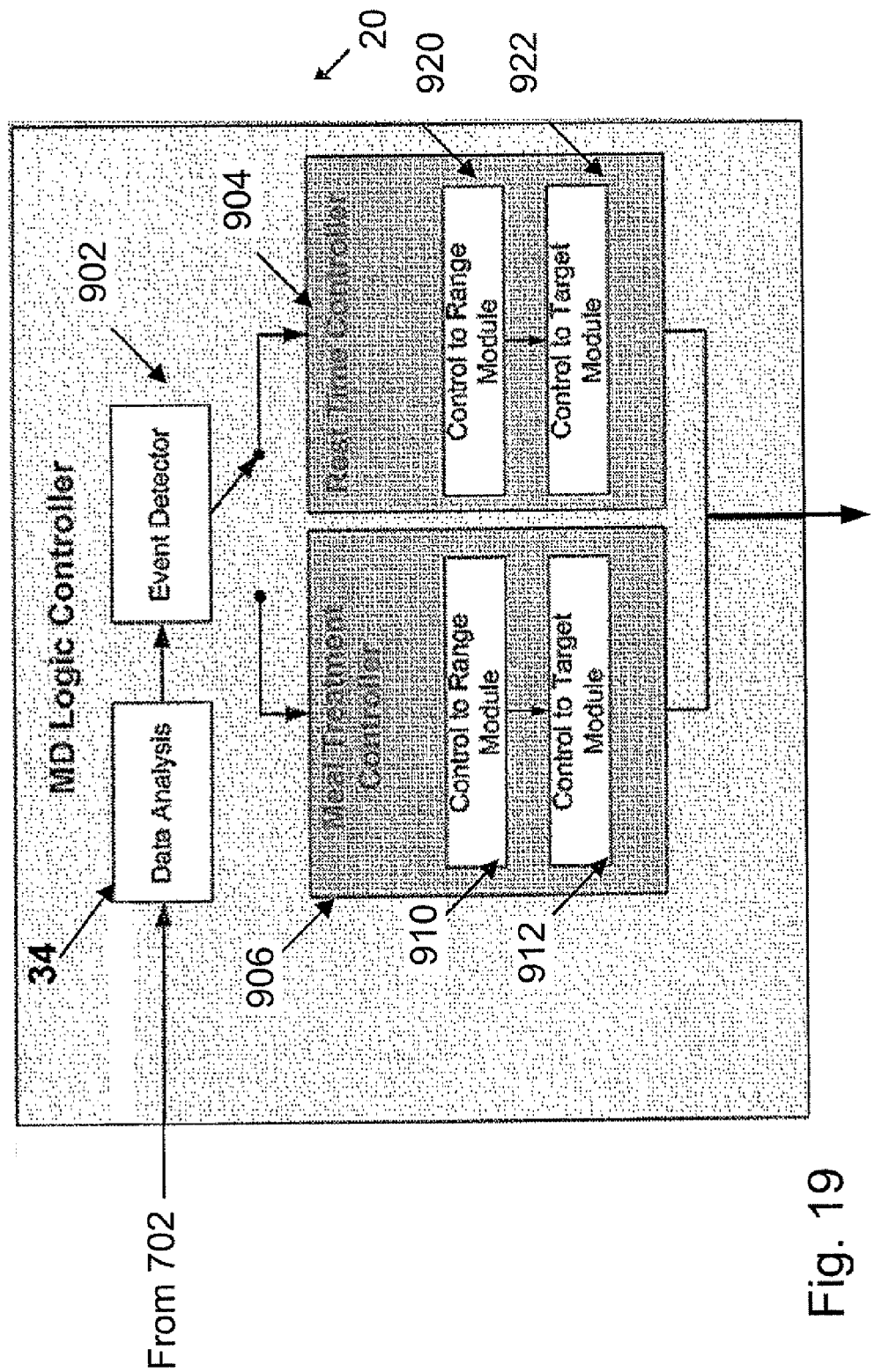
FIG. 19 is a schematic diagram of a treatment system utilizing a monitoring system of the present invention, including an event detector.

Reference is now made to FIG. 19 exemplifying a flow diagram within the processing unit 30 of a treatment system utilizing a monitoring system of the present invention according to one embodiment of the present invention.

In some embodiments, the system comprises an event detector module 902 operable to determine the occurrence of an event or the probability of the patient to be in a special event as a function of a time. The special event may be sleep, meal, exercise or disease event. The event detector module is designed to detect such special dynamics associated with each special event. Based on the event that was detected, the proper CRM and CTM are selected.

In some embodiments, at least two controllers are used: rest time controller (for example, the fuzzy logic engine previously discussed above) and a controller designed to deal with the special event, such as a meal, which is referred to as meal treatment module/meal time controller. Therefore, the present invention provides for alternating between at least two fuzzy logic engines (rest time controller and meal time controller).

According to some embodiments of the present invention the processing unit 30 comprises an event detector 902 capable for detecting meal events. In case a meal event was detected, a meal treatment module 906 configured and operable to generate an analysis of the meal event is activated. The meal treatment module 906 if needed provides a treatment modification of the patient conditions to suite the meal events. In other cases, when no meal event was detected, the Rest Time Controller 904 is operable. Each controller has its own CRM (910 and 920) and CTM (912 and 922), respectively. The CRM 920 and CTM 922 of the Rest Time Controller 904 are similar to the modules described above. The CRM 910 of the meal treatment module 906 runs a different table of rules.

Each rule can comprise a proposed modification of the possible insulin/glucagon treatment during meal.

Specifically, an event detection module 902 is utilized to detect an event which requires specialized treatment. For example, a meal detection module can be used in order to allow a treatment suitable to an event of meal. This module monitors the blood glucose level and analyzes pattern(s) or traces of glucose levels. In some embodiments, the meal event detector can use the definitions of the glucose qualitative parameters as they were defined for the fuzzy logic module above. On detection of an abnormality in the blood glucose level, a special event is invoked allowing the system and providing the required resources of time (or otherwise) to handle the event.

In addition, a procedure or test can be used to detect the occurrence of a special event such as a meal event. Several tests can be employed in this respect. A test can also be employed to deny a meal event from the patient. In some embodiments, a meal event is determined in accordance to a pattern or trace of glucose measurements.

The following terms are used in the followings possible tests:

The term "Relevant Trend for Special Event Long" refers to the trend of the blood glucose level log/pattern as determined in N samples, typically the recent or last N samples. Optionally, the trend can be determined in accordance to method previously elaborated herein. The trend(s) can conveniently be denoted as $a_1 \ldots a_N$ and the relative times are $\tau_1 \ldots \tau_N$ while $\tau_i > \tau_{i+1}$.

The term "Relevant Trend for Special Event Short" refers to the trend of the blood glucose log/pattern as determined in M samples while M<N. Typically the recent or last M samples are used in this event. The trend(s) are $a_1 \ldots a_M$ and the relative times are $\tau_1 \ldots \tau_M$ while $\tau_i > \tau_{i+1}$. Optionally, the trend is can be determined in accordance to method previously elaborated herein The term "Duration" refers to a predefined number of sample which represents the amount of samples used for analysis.

The term "Differential for Special Event Long" refers to the slope (or derivative) of the blood glucose log/pattern as determined in N samples, typically the recent or last N samples. The trend(s) are $d_1 \ldots d_N$ and the corresponding sample times of the trend(s) are $\tau_1 \ldots \tau_N$ while $\tau_i > \tau_{i+1}$.

The term "Differential for Special Event Short" refers to the slope (or derivative) of the blood glucose log/pattern as determined in M samples while M<N. Typically, the recent or last M samples are used in this event. The trends are $d_1 \ldots d_M$ and the corresponding sample times are $\tau_1 \ldots \tau_M$ while $\tau_i > \tau_{i+1}$.

In some embodiments, an event is determined in accordance to pattern or traces of glucose level measurements. In some embodiments, occurrence of the event is determined in accordance to a trend of pattern or traces of glucose measurements. The event can be a meal event or a default stable glucose level (i.e. a steady state of measured glucose level). In some embodiments, the trend is any of Relevant Trend for Special Event Long or Relevant Trend for Special Event Short.

Specifically, an event (such as a meal event) can be determined in case the trend exceeds a defined threshold or a threshold of defined qualitative input parameters. Optionally, the event can be determined if the calculated trend exceeds a preceding trend of traces of glucose measurements. In some embodiments, an event can be determined if the calculated trend exceeds a defined threshold for a defined duration.

In addition, an event (such as an exercise event) can be determined in case the trend decreases below a defined threshold or a threshold of defined qualitative input parameters. The occurrence of the event can be determined if the calculated trend decreases below a preceding trend of traces of glucose measurements. In some embodiments, the event can be determined where the calculated trend decreases below a defined threshold for a defined duration. For example, test A positively identifies a meal event if the following condition is satisfied ∀a∈Relevant Trend for Special Event Short:

i. $a_i \geq a_{i+1}$ ii. $a_1 \geq w \cdot$(Low Boundary of Steep Rise)$+(1-w)\cdot$(Low Bound of Rise),, 0<w<1.

where, w is a weight factor which will be set empirically; The qualitative parameters may be defined as low boundary of steep rise and low bound of rise set empirically by the user or automatically by an automated procedure Test B will positively detect a meal event if the following conditions are satisfied ∀a∈Relevant Trend for Special Event Long:

iii. At least for Duration of the samples $a_i \geq$Stable iv. $a_1$>Stable and $a_2$>Stable where, the definition of Stable can be according to the definition of Stable member functions in the fuzzy engine or otherwise set by the user.

Test C will positive detect a meal event if the following terms are satisfied ∀a∈Relevant Trend for Special Event Short: The difference between the blood glucose level at $\tau_1$ and the blood glucose level a $\tau_M$ is at least X v. The difference between the blood glucose level at and the blood glucose level at $\tau_N$ is at least Y, while Y≥X Test D will positively identify a meal event if the following terms are satisfied $\forall a_i | i=1, 2, 3, a_i > w \cdot$(Low Boundry of Steep Rise)$+(1-w) \cdot$(Low Bound of Rise), where, w is a weight factor which will be set empirically or by automated procedure.

Test E checks that slope of the last (or previous) sample is smaller than Low Bound Rise. Test E can be used to deny a meal possibility from the patient.

At each testing point during the operation of the systems or method disclosed herein, one or more of the above tests above may be satisfied. Other test can also be devised in that respect. A meal/event detection module can be configured and operable to detect an event such as a meal by performing the detection tests. By running the meal detection module on a large set of measured data, the probability of each single test to detect the meal/event (i.e. the test's positive predictive value) can be ascertained, as well as the probability combination of tests to detect the meal/event at the same sample time. In addition, conditional probability of single test and/or combination of test(s) to detect the meal/event given a previous sample can be ascertained. The meal detection module can be tested on empirically data in order to calculate each test's positive predictive value. The result of the calculation can then be used as the probability for each test to positively detect a meal event. The absence of a meal event can also be detected in similar manner.

The following table provides an example for the probabilities of each test (that were described above) and tests combinations that were calculated using the 10 adult group from the training version of the UVa/Padova simulator [5]. The test or test combination frequency of use (1—most frequently used and 14—rarely used) is a parameter which scales the tests according to the number of times in which they were activated. For example, the probability of Test A to positively detect a meal is 100% however it is rarely activated.

| Test Combination | Probability to positively detect a meal event | Test's frequency of use |
|---|---|---|
| A | 100% | 13 |
| AB | 88% | 12 |
| ABC | 72% | 4 |
| ABCD | 90% | 1 |
| ABD | 0% | 14 |
| AC | 84% | 5 |
| ACD | 100% | 10 |
| AD | 0% | 14 |
| B | 23% | 8 |
| BC | 28% | 6 |
| BCD | 72% | 2 |
| BD | 54% | 9 |
| C | 43% | 3 |
| CD | 83% | 11 |
| D | 67% | 7 |

The output of the meal detection module can be either positive or negative. In addition, the output of the meal detection module will be the probability that a special event, i.e. meal or sudden rise of the blood glucose levels, occurs.

A threshold probability (P %) can be determined for the occurrence of the special event. Once the system recognizes that the probably for a special event exceeded the determined threshold, it can switch the CRM and CTM previously used i.e. either a default CRM and CTM (referred in FIG. 5 as Rest Time Controller 904) or another treatment module designed for other special events.

The CRM 910 of the meal treatment module 906 uses a fuzzy logic engine which typically has the same working principles described for the rest time CRM 920. It may differ in the input parameters and it may have the same output parameters or modified output parameters. A possible strategy for meal related CRM fuzzy logic engine ("special event fuzzy engine") is based on the time elapsed from the first detected special event of a measured series. It can thus allow application of treatment rules comprising greater amount of insulin in a first stage in order to deal with the special event. On the other hand, it allows the system to be more decisive on decreasing the basal rate and even stopping the insulin infusion in order to prevent hypoglycemia.

There are several conditions which can control the switching or alternating between the meal treatment module 906 and Rest time controller 904.

For example, if the last used module is the rest time controller, the conditions can be as follows:

1. Obtaining the blood glucose level reading;

2. If the probably of special event is P % or higher, switching to the special event fuzzy engine, otherwise continue with the rest time controller For example, if the last used controller is the meal treatment module:

1. Get the blood glucose level ([$BG_{i-N}$:$BG_i$]) reading and past glucose trend ([$\overset{\circ}{BG}_{i-N}$:$\overset{\circ}{BG}_i$]) for time samples [$t_{i-N}$:$t_i$];

2. if one of the following conditions is satisfied—switching to the rest time controller;

a. If each value [$\overset{\circ}{BG}_{i-N}$:$\overset{\circ}{BG}_i$] is the range of Stable AND each of the samples [$BG_{i-N}$:$BG_i$] is lower than a threshold, for example, 130 mg/dl;

b. If each of the samples [$BG_{i-N}$:$BG_i$] is in the blood glucose range of [Blood Glucose Target−Y %, Blood Glucose Target+Z %] AND each of the samples [$\overset{\circ}{BG}_{i-N}$:$\overset{\circ}{BG}_i$] is lower than high boundary of the Stable range;

3. Otherwise, if there has been more than T minutes from the first detected special event of the previous/last series and at current sample, a special event was detected as well; set the current sample as the first detected special event of a new series and continue using the meal treatment module;

4. If none of the above conditions is satisfied, use meal treatment module; The input parameters for the special event fuzzy engine are as follows: Blood glucose level trend in the last $T_1$ minutes, current blood glucose level, predicted blood glucose level trend in the next $T_2$ minutes, predicted blood glucose level in $T_2$ minutes, time elapsed since a first detected special event of a previous/last measurement series, blood glucose level trend in the last $T_3$ minutes before the first detected special event of the previous/last series and blood glucose level at the time of the first detected special event of the last series.

The output parameters for the special event fuzzy engine are as follows: change of basal infusion rate from the default basal and percent of insulin/glucagon bolus.

By way of non-limiting example, the input parameters and the corresponding membership functions used herein below refer to MATLAB built membership functions as follows: "smf", shaped membership function; "Zmf" Z-shaped membership function; "gauss2mf", Gaussian combination membership function; "trimf", Triangular-shaped built-in membership function; and "trapmf", Triangular-shaped built-in membership function.

Qualitative Inputs Parameters:

Past Trend of Blood Glucose (i.e. Blood glucose level trend in the last $T_1$ minutes [mg/dl/min])

| MF name | MF function | MF ranges |
| --- | --- | --- |
| Rapid Descent | Zmf | −5, −2.5 |
| Moderate Descent | gauss2mf | −2.5, −1.5 |
| Slow Descent | gauss2mf | −1.5, −0.5 |
| Stable | gauss2mf | 0.5, 0.5 |
| Slow Increase | gauss2mf | 0.5, 1.5 |
| Rapid Increase | Smf | 2.5, 5 |
| Slow Increase or Stable | gauss2mf | 0, 1.5 |
| Some Descent | Zmf | −5, −0.5 |
| Not Rapid Descent | gauss2mf | −2.5, 0 |
| Not Rapid Increase | gauss2mf | 0.5, 2.5 |

Current Blood Glucose level [mg/dl]

| MF name | MF function | MF ranges |
| --- | --- | --- |
| Low and Below | Zmf | 20, 70 |
| Normal | gauss2mf | 90, 150 |
| High | gauss2mf | 150, 220 |
| Very High | Smf | 220, 300 |
| Below Normal | Zmf | 20, 90 |
| Above Normal | Smf | 130, 300 |
| High and Above | Smf | 180, 300 |

Future Trend of Blood Glucose (i.e. Predicted blood glucose level trend in the next $T_2$ minutes [mg/dl/min])

| MF name | MF function | MF ranges |
| --- | --- | --- |
| Rapid Decrease | zmf | −5, −2.5 |
| Slow Decrease | gauss2mf | −1.5, −0.5 |
| Stable | gauss2mf | −0.5, 0.5 |
| Slow Increase | gauss2mf | 0.5, 1.5 |
| Moderate Increase | gauss2mf | 1.5, 2.5 |
| Rapid Increase | smf | 2.5, 5 |
| Some Decrease | zmf | −0.5, −5 |
| Not Rapid Decrease | gauss2mf | −0.5, −2.5 |
| Not Increasing | zmf | −5, 0.5 |
| Some Increase | smf | 0.5, 5 |
| Not Rapid Rise | gauss2mf | 0.5, 2.5 |
| Not Slow Rise | smf | 1.5, 5 |

Predicted blood glucose level in $T_2$ minutes [mg/dl]

| MF name | MF function | MF ranges |
| --- | --- | --- |
| Low and Below | zmf | 20, 90 |
| Normal | gauss2mf | 90, 140 |
| High | gauss2mf | 180, 220 |
| Very High | smf | 220, 300 |
| Not Low | smf | 110, 180 |
| Below Normal | zmf | 20, 90 |
| Not Above Normal | zmf | 70, 130 |
| Above Normal | smf | 130, 180 |
| High or Very High | smf | 180, 300 |

Time past since the first detected special event of the last series [min])

| MF name | MF function | MF ranges |
| --- | --- | --- |
| Meal Start | zmf | 0, 45 |
| During Meal | smf | 45, 300 |

Blood glucose level trend in the last $T_3$ minutes before the first detected special event of the last series [mg/dl/min]

| MF name | MF function | MF ranges |
| --- | --- | --- |
| Slow Increase | gauss2mf | 0.5, 1.5 |
| Moderate Increase | gauss2mf | 1.5, 2.5 |
| Rapid Increase | smf | 2.5, 5 |
| Not Slow Rise | smf | 1.5, 5 |
| Some Increase | smf | 0.5, 5 |
| Not Rapid Rise | gauss2mf | 0.5, 2.5 |

Blood glucose level at the time of the first detected special event of the last series. [mg/dl]

| MF name | MF function | MF ranges |
| --- | --- | --- |
| Low and Below | zmf | 20, 70 |
| Normal | gauss2mf | 90, 130 |
| Very High | gauss2mf | 220, 300 |
| Below Normal | zmf | 60, 95 |
| Above Normal | smf | 135, 220 |

Output Parameters:

Change in percent of basal infusion rate from the default basal [%]

| MF name | MF function | MF ranges |
|---|---|---|
| 0 | trapmf | −100 |
| 0.2 | trimf | −80 |
| 0.5 | trimf | −50 |
| 1 | trimf | 0 |
| 1.5 | trimf | +50 |
| 2 | trapmf | +100 |

Percent of bolus [%]

| MF name | MF function | MF ranges |
|---|---|---|
| 0 | trapmf | 0 |
| 0.5 | trimf | 50 |
| 1 | trimf | 100 |
| 1.2 | trimf | 120 |
| 1.35 | trimf | 135 |
| 1.7 | trimf | 170 |
| 2 | trimf | 200 |
| 2.5 | trimf | 250 |
| 3 | trapmf | 300 |

The person skilled in the art would appreciate that the glucose ranges, member functions and time intervals can also be modified in accordance to suit particular treatment envisaged.

The table of rules of the special event module (or special event CRM) may have a number of inputs from one to seven inputs and a number of outputs from one to two. The ranges of such inputs and outputs are defined per se and are not different for each fuzzy logic module.

For example, the CRM for meal event includes 130 rules, Some exemplary rules are provided as follows:

Rule #21: If Time Passed from Meal Start is not greater than 45 minutes, Current Blood Glucose Level is Normal and Predicted Blood Glucose Level is Very High than give 200% of basal and 300% of recommended bolus;

Rule #84: If Time Passed from Meal Start is greater than 45 minutes, the is Past Trend of Blood Glucose is not increasing rapidly and Current Blood Glucose Level is High than give 100% of basal rate and 100% of recommended bolus;

Rule #110: If Time Passed from Meal Start is greater than 45 minutes, Current Blood Glucose Level is High, the Future Trend of Blood Glucose is not increasing rapidly and Predicted Blood Glucose Level is High than give 100% of basal rate and 120% of recommended bolus;

Rule #126: If Time Passed from Meal Start is greater than 45 minutes, the Past Trend of Blood Glucose is not Descending Rapidly, Current Blood Glucose Level is Above Normal and Predicted Blood Glucose Level is Above Normal than give 100% of basal and do not give any bolus;

Rule #128: If Time Passed from Meal Start is greater than 45 minutes, the Past Trend of Blood Glucose is Stable, Current Blood Glucose Level is Above Normal and Predicted Blood Glucose Level is Above Normal than give 100% of basal and 100% of recommended bolus.

The meal detection and treatment module uses a combination of fuzzy logic model and trend analysis of glucose profile. The system including a meal detection and treatment module was evaluated on 24 hour in silica trials with three meals using the UVA/Padova simulator. The improved system succeeded to increase the time spent between 70-180 mg/dl by 10% (p=0.02) by decreasing the time spent above 180 mg/dl in similar percent (p=0.02) and without increasing time spent below 70 mg/dl. In both systems, time spent below 70 mg/dl was on average less than 1.6%. In addition, mean BG level was decreased from 150 mg/dl to 138 mg/dl (p=0.002).

Figure 20:
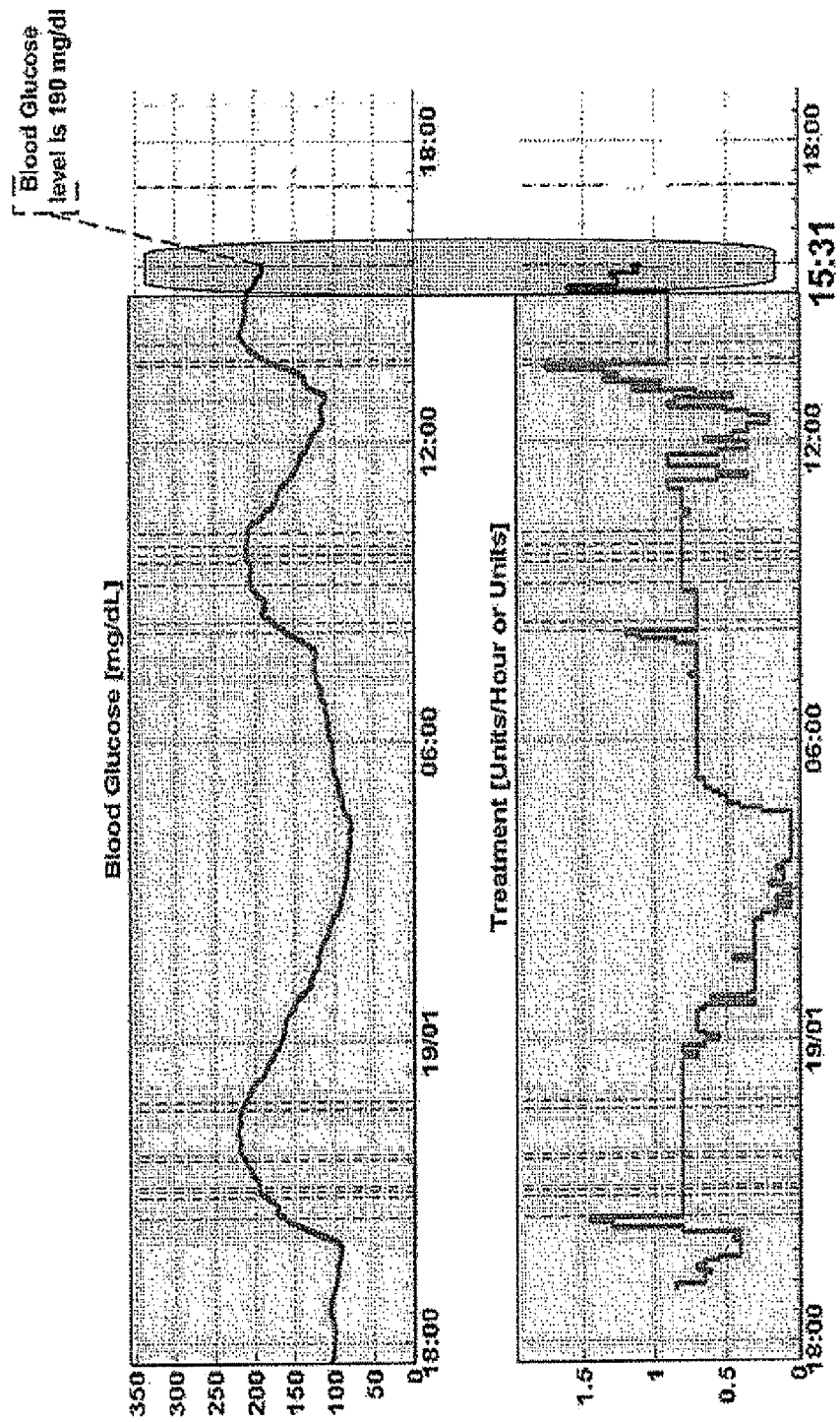
FIG. 20 is an example of the operation of the monitoring system utilizing a of the present invention.

Reference is made to FIG. 20 illustrating an example of the operation of the processing unit 30. The encircled area is the current decision point (15 h31) of the system at which the measured data is a glucose level of 190 mg/dl. The portion of the graph before the encircled area is the measured data stored in the History Log.

The patient profile includes basal plan, correction factor, active insulin etc. For example the basal rate taken from the basal plan assigned for the time 15 h31 is 0.9 units per hour, the correction factor is 50 mg/dl/unit and the predefined glucose target level is 110 mg/dl.

The data analysis 34 provides for example that the past trend is 0 mg/dl/min, the future trend is −0.24 mg/dl/min and the predicted glucose level is in the coming 30 minutes is 179 mg/dl/min.

Since no special event was detected the Rest Time controller is applied.

The CRM 910 uses appropriate rules from the table of rules therefore increasing the basal rate by 79% and deliver 73% of the calculated bolus. The CTM 912 outputs that for a glucose level of 190 mg/dl, the insulin amount 1.6 units. 73% of the 1.6 units of recommended bolus are 1.1 units. The suggestion may also be stored in the History Log.

Since a bolus is recommended, the CTM decides to ignore the CRM recommendation of increasing the basal rate and sends the following command to the delivery pump: basal rate=0.9 units/hour and bolus units. The insulin pump 24 receives the amount of insulin to be delivered.

According to another broad aspect of the present invention, there is provided a method which improves and maintains the closed-loop system performance and therefore the treatment on a specific patient. The method is a learning algorithm for automatic analysis of control performances against intra-patient variances in the glucose/insulin dynamics, with adjustments of the control parameters accordingly. The learning method can be performed by an independent module to extract the patient profile from data.

The method comprises analyzing initial settings based on open loop data, as well as making periodical adjustments during close-loop operation.

The performances of the learning integrated method were evaluated using ten subject adult population from the UVa/Padova simulator. A nominal simulation day consists with three meals (at 9 am, 2 pm and 7 pm, of 40 g, 70 g and 50 g, respectively) was defined. All subjects followed the same scenario which includes open-loop un-perfect meals carbohydrate estimation (2 days) followed by close-loop (5 days) therapy. The learning method was automatically activated after the open-loop section as well as after every 24 h of close-loop until achieving optimal performances. The clinical measures achieved during optimal day of close-loop (OpCL), day 1 of close-loop (D1CL) and average open-loop (AOL) were compared (one way ANOVA). BG below 70 mg/dl was 0-0.4% in all days of simulation. While there was no significant change in the administrated insulin, time spent in 80-120 mg/dl was significant greater in OpCL (53±8%) versus D1CL (41±8%) and AOL (18±8%) (p<0.001). Mean BG was 121±5 mg/dl in OpCL compared to 129±7 mg/dl in D1CL (p=0.01) and 140±7 mg/dl in AOL (p<0.001).

The present invention discloses an automated learning method and systems for permitting automatic determination of the patient's initial treatment profile. These methods can be performed by a dedicated module configured and operable to execute them. The learning method can be divided into two main sub-procedures:

I) An initial learning, which receives measured data of the subject during open-loop associated treatment. Typically, the measured data is collected while the patient is performing his own treatment at home. The data is typically generated by at least one of drug delivery devices and glucose measurement devices and comprises the sensor readings, meal amounts and times and/or insulin treatment(s), either bolus and basal. The initial learning procedure can analyze the data (measured or calculated) and determine automatically the patient's initial treatment profile. The patient's initial treatment profile include at least one of correction factor, basal plan, insulin/glucagon pharmacokinetics associated data, glucose target level or target range level, glucagon dosage, insulin bolus and insulin activity model;

II) The continuous learning procedure can update the patient's treatment profile during the closed-loop operation. The patient's treatment profile include at least one of basal plan, insulin sensitivity factors for carbohydrates and glucose level correction, glucagon sensitivity factor and insulin/glucagon pharmacodynamics associated data. The patient's treatment profile can be adaptive in accordance with closed-loop history log.

The initial learning sub procedure and the continuous learning procedure can be performed separately, sequentially or in combination.

In some embodiment, the insulin sensitivity factors (for carbohydrates and glucose level correction, denoted as CF) are determined during the initial learning procedure. In some embodiments, the insulin sensitivity factor is determined at least in accordance with carbohydrate consumed by the patient, measured data of glucose sensor reading, and the patient's treatment which can include insulin dosage, or basal plan.

Optionally, the data is collected while the patient was at home. In one embodiment, optionally during the initial learning procedure, an insulin sensitivity factor $CF_1$ is determined as follows:

Determining $CF_I$ in accordance with carbohydrate amount, glucose and insulin related data:

$$CF_1 = \frac{G_e - G_s + dC \cdot C}{B}$$

wherein $G_e$ is the first sensor reading [mg/dl] of the open loop session; $G_s$ is the last sensor reading [mg/dl] of the open loop session; dC is a glucose to carbohydrate ratio. The ratio of glucose to carbohydrate can be 3.33, (based on empirical knowledge); C is amount of carbohydrate consumed [e.g. gr] during the open loop; and B is the amount of bolus insulin provided [units of insulin] during the open loop session.

$G_e$-$G_s$ is defined as the difference between $G_e$ (a first glucose sensor reading) and $G_s$ (a second glucose sensor reading). The time interval between the two glucose sensor readings can be defining a time window.

In some embodiments, the glucose derived from the consumed carbohydrate within the time window is estimated. Such estimation can be performed by obtaining an amount of carbohydrate consumed in the time window and transforming the carbohydrate amount to glucose derived thereof.

The transformation can be performed by determining a coefficient defining the proportion of consumed carbohydrate to glucose derived thereby e.g. (dC above). By multiplying the coefficient with the amount of carbohydrate consumed in the time window, the glucose derived from the consumed carbohydrate is determined.

Adjustment of difference between the first and second glucose sensor reading can be effected by summing the difference between the first and second glucose sensor readings and the glucose derived from the consumed carbohydrate; thereby obtaining an adjusted glucose amount.

Determining the insulin sensitivity (e.g. CF1) can be determined in accordance to the relation between the adjusted glucose amount and insulin bolus provided during the time window. Relation can be the defined by the proportions between the respective values as shown above.

In some embodiments, $G_e$ may be the first reading of a portion of an open loop session and/or $G_s$ may be the last sensor reading of a portion of an open loop session. In some embodiments, $G_e$ may be the first reading of a portion of a closed loop session and/or $G_s$ may be the last sensor reading of a portion of a closed loop session.

Optionally, the sensitivity factor such as $CF_1$ may be modified based on analysis of the quality of glucose control of the patient using the data that was collected while the patient was at home.

In some embodiments, insulin sensitivity factor (e.g. CF1) is modified in accordance with measured glucose levels. For example, insulin sensitivity factor is modified in accordance with minimum sensor reading or lowest blood glucose reading recorded in neither during hypoglycaemia nor hypoglycaemia. In a specific example, the insulin sensitivity is modified in accordance with proportion between minimum sensor reading during the time window and the lowest blood glucose reading recorded in neither during hypoglycaemia nor hypoglycaemia. In some embodiments, the insulin sensitivity is modified in accordance to the maximum sensor reading in a time interval prior to the obtaining of the minimum sensor reading (an example is shown below).

Therefore, insulin sensitivity or CF1 can further be modified in accordance with factor (a) to produce a modified correction factor $CF_2$ in accordance with the formula: $CF_2 = a \cdot CF_1$ wherein factor (a) is defined as the factor of modification of $CF_1$.

Factor a may be determined, according to the following procedure:

```
If Thypo>0 or Tihypo > 1
    If (Speak>Smin) and (Speak> UpperLimit)
        a = (Speak – Smin)/ (Speak –UpperLimit);
    Else
        a = UpperLimit/Smin;
    End
Else
``` wherein Thypo is a percent of time spent in defined hypoglycemia range during the relevant period; Tihypo is a percent of time spent in defined impending hypoglycemia range during the relevant period; 5 min is a minimum sensor reading during the relevant period; Smean is the average sensor readings during the relevant period; Smax is a maximum sensor reading during the relevant period; Speak is a maximum sensor level in time range of up to three hours before the 5 min tim, during the relevant period; UpperLimit is the lowest blood glucose reading that is recorded neither during impending hypoglycemia nor hypoglycemia; Sn_low is the lower boundary of "strict normal" glucose range (can be empirically defined as the glucose range in the range of about 80-120 mg/dl), which is typically set to be 80; Sn_high is the higher boundary of "strict normal" glucose range, which can be set to be 120; dN is the subtraction Sn_high−Sn_low.

A histogram (or alternatively a distribution function) can be determined by using the measured glucose levels of the patient. The histogram is a function representing occurrences of each measured glucose level of the patient during a certain time window. P can be defined as summation of the occurrences (or an accumulated measured glucose levels) at an interval of a specific width (dN representing glucose measurement interval), wherein v is the initial glucose reading in this specific window, individualized for each patient.

val=argmax$_v${P(v,v+dN)}, where P(v,v+dN) is the percentage of glucose readings with the range [v,v+dN]; argmax$_v$ means determining the v where P reaches maximum value.

$$a = 0.57 \cdot a\_Tsn + 0.28 \cdot a\_Hyper + 0.15 \cdot a\_Mean, \text{ where}$$

a_Tsn=sn_low/val;
a_Hyper=180/Smax; typically defined empirically
a_Mean=110/Smean; typically defined empirically
W=[0.57 0.28 0.15], a weighing vector/coefficients, typically defined empirically.
End The person skilled in the art would appreciate that the weighing vector can be adjusted or modified to suit particular insulin/glucagons treatments.

In some embodiments, therefore a histogram representing the occurrence of measured glucose level of the patient during a certain time window is determined. The local maximum (or peak) in a glucose measurement interval can then be obtained, for example by maximizing the function P(v, v+dN) as exemplified above.

Therefore, in some embodiments, the insulin sensitivity factor is modified in accordance with the local maximum (or peak) of measured glucose level histogram within a glucose level interval. In some embodiments, the insulin sensitivity factor is modified in accordance the accumulated measured glucose level in the histogram within a glucose level interval. Modification of the insulin sensitivity factor can take the form of transforming the accumulated measured glucose levels in accordance with a weighing vector or coefficient.

In some embodiments, the safety of $CF_2$ or $CF_1$ can be tested to verify that whether the insulin dosing provided is safe. The test can be performed by processing a series of glucose sensor reading previously obtained for a treated patient (such as the treated patient) i.e. a previous glucose trace. Thus, sensor readings from the open loop session can be used to simulate insulin bolus recommendations for the closed-loop session.

In some embodiments, the test is defined as follows:

If Bsim > Btotal
$$CF = \frac{Bsim}{Btotal} \cdot CF_2$$
Else
$$CF = CF_2$$
End wherein Bsim is total insulin boluses given by simulated closed-loop system (in case when simulating the open loop sensor readings), Btotal is the total amount of bolus insulin given during the open loop session.

As described above, the insulin sensitivity can include two separate factors: insulin sensitivity for carbohydrates and insulin sensitivity for glucose levels correction.

In some embodiments, insulin/glucagons pharmacodynamics of an individual is represented by a series or a curve describing the insulin/glucagon "active" in the blood at a certain time associated with a meal event. Therefore, the initial settings can further include determination of the pharmacodynamics parameters for insulin (denoted as active insulin) for the individual patient, as concluded from the open loop data. Active insulin can be defined with reference to a specific meal or to a series of meals.

Ali is defined as the active insulin for a specific meal. The time of the meal is denoted as T0. For each meal (carbohydrates consumption noted in open loop data), a first time window is defined starting from the specific meal T0 at the open loop data until the next meal time or until seven hours after the meal, the earlier between the two. Peak sensor value after the meal is identified is denoted as Smmax. Minimum sensor value which occurred after the peak is denoted as Smmin. The respective time tag when the peaks where obtained is typically recorded, defining a second time window between the time Smmax and Smmin. Sensor data during the second time window is obtained. The obtained sensor data can be represented by a series of [Ti, Vi], where Ti are the time tags of sensor readings with reference to the beginning the meal T0, and Vi are sensor values measured at their respective Ti In some embodiments, the measured sensor reading is normalized. The measured sensor reading can be normalized to value between 0 and 1. Ni represents the normalized value of the respective Vi.

Ni can be calculated as follows:

$$Ni = Vi/(Smmax - Smmin).$$

Normalized series [Ti, Ni] can thus be obtained.

In some embodiments, the series (either [Ti, Vi] or [Ti, Ni]) are modified (or "forced") into a monotonic series such as a monotonic non-increasing series. Thus, in one embodiment, a non-increasing series is obtained by associating each Ni to a minimum normalized Nj, j=1 to i.

In other words, Ni=min({Nj}, j−1:i).

For example, for the series $N_j$={1, 0.9, 0.5, 1.2, 0.7}, $N_i$ will be {1, 0.9, 0.8, 0.8, 0.7}.

The meal peak value i.e. at T0, can be added [T0, 1] at the beginning of the series [Ti, Ni].

The series thus obtained represents the active insulin Ali for a specific meal.

Therefore, the present invention provides a method for determining a series or a curve describing the insulin/glucagon in the blood at a certain time window associated with a meal event, the method comprises obtaining plurality of sensor data measured during the time window starting at T0, representing the time of the occurrence of the meal; optionally normalizing the sensor data; and transforming the measured sensor data (or normalized sensor data) to a monotonic non-increasing series or curve; thereby obtaining a series or a curve describing the insulin/glucagon in the blood at the time window associated with the meal event.

The method for determining a series or a curve describing the insulin/glucagon in the blood can be performed either during open-loop session or during a closed loop session (i.e. in real time). Accordingly, the patient's treatment profile can be modified before, at an initial learning phase or during treatment.

In some embodiments, the plurality of sensor data measured during the time window can be represented by a series of [Ti, Vi'], where Ti are the time tags of sensor readings with reference to the beginning the meal T0, and Vi are sensor values measured at their respective Ti.

In some embodiments, the step of transforming the measured sensor data to a monotonic non-increasing series comprises associating each Vi of the resultant monotonic non-increasing series to a minimum Vj, j=1 to I in the measured sensor data.

In some embodiments, the step of transforming the normalized measured sensor data to a monotonic non-increasing series comprises associating each Ni of the resultant monotonic non-increasing series to a minimum normalized Nj, j=1 to I in the normalized sensor data.

Where more than one meal took place, the active insulin series for a set of meals can be obtained. In one embodiment, the active insulin for a set of meals is the median of all the meal series {Ali}. The resultant series, denoted as AI_total represents an active insulin curve. The values represent the percentage of insulin which is still active in the treated patient. For example, elements of [t=25, v=0.8], within the AI_total series, can indicate that 25 minutes after injecting a bolus, 80% percent of insulin was still active.

In some embodiments, basal plan is monitored and optionally modified. Insulin basal rate typically affects the dynamics of the glucose levels, but this effect is subtle compared to the observed effect of carbohydrates consumption (meals) and given insulin (boluses). Therefore, the open loop data is "cleaned" by taking out every segment of glucose levels that might be affected by meals or bolus insulin.

In some embodiments, an effect window or zone of both meal and/or bolus injection is determined (either automatically or manually such as by the physician). For example, the effect zone, can be three hours measured from the giving of the bolus or the meal. Optionally, the effect zone is set to 2, 3.5, 4, 6 or 8 hours measured from the giving of the bolus or the meal, or even more.

Glucose sensor readings (G(t) and the basal rates (B(t)) during the effect zone can be referred to as "clean data". A change of glucose levels in time (t) can be defined by: DG(t) =dG/dt.

Basal rates at B(t) will affect DG(t+A) due to the delay time caused by infusing. A, the time delay can be derived by determining A=argmax(A, E(B(t)DG(t+A))), wherein A is the parameter which maximizes the expectancy of the multiplied series B(t)*DG(t+A).

With a given A, a series of [DG(t+A), B(t)] can be defined. Therefore, in some embodiments, the relationship between bolus injections and change of glucose level is represented by the series [DG(t+A), B(t)], thereby obtaining a series of basal treatment rates and corresponding changes in glucose level in a treated patient. Optionally, the series [DG(t+A), B(t)] can be interpolated the series values to find B(t) when DG(t+A)=0, thereby enabling a selection of a basal treatment rate which minimizes a change in the glucose level (e.g. B(t)) from the series of basal treatment rates. The obtained basal treatment rate can be used to modify the basal plan of the treated patient e.g. by inserting the obtained basal treatment rate as an element in the basal plan. Thus, the basal treatment plan obtained provides for minimal changes in glucose level. This method can be used for controlling a personal basal plan of the patient.

Therefore, in one of its aspects, the present invention relates to a method for determining insulin basal plan suitable for a patient in need thereof, the basal plan is characterized by reducing the changes to the glucose levels in the treated patient. The insulin basal plan is derived from a series of basal treatment rates. The basal plan obtained can thus be optimal. The method can be performed either during open-loop or closed-loop sessions.

The method for determining of insulin basal plan from a series of basal treatment rates for a patient in need thereof, comprises: obtaining a series of basal treatment rates as a function of time; obtaining measured data of glucose level in the patient as a function of time; determining series of changes in glucose levels as a function of time; determining the personal time delay of the treated patient which is estimated from the series of basal treatment rates and the series of changes in glucose levels, thereby obtaining a series of basal treatment rates and corresponding changes in glucose level in the patient; selecting a basal plan which incorporates the basal rates that minimizes the change in the glucose level.

In some embodiments, measured data of glucose level in the patient is derived from glucose sensor readings, denoted as G(t) above. In some embodiments, basal treatment rates as a function of time is derived from basal rates, denoted as B(t) above.

In some embodiments, the method is applied during a predefined effect zone. In some embodiments, a change of glucose levels in time (t) can be defined by: DG(t)=dG/dt.

In some embodiments, the personal time delay of the treated patient is determined by maximizing the expectancy of the multiplied series B(t)*DG(t+A) such that A=argmax (A, E{B(t)DG(t+A)}), wherein A is the parameter which maximizes the expectancy of the multiplied series B(t)*DG (t+A).

In some embodiments, the continuous learning procedure (or Runtime learning) modifies the insulin sensitivity factor (e.g. CF) according to the observable/measured data. The insulin sensitivity factor can be modified in accordance with at least one of the set {CF(i), LOG(i)}, where CF(i=1) is the first CF and LOG(i=1) is the relevant LOG for the corresponding period of CF(i=1), i.e. the time zone in which the system utilized CF(i).

The first step of the continuous learning procedure is to determine the factor a in accordance to the last CF and LOG in the set. These are denoted for convenience as CF(END) and LOG(END). LOG(END) defining the corresponding time zone/period in which the system utilized CF(END). Factor a can be determined as previously noted with respect to initial learning procedure The modified correction factor CFnew can be determined as follows: CFnew=a*CF(END). In some embodiments, the modified correction factor is verified as reasonable or as safe. Verification of the modified correction factor can be performed by forcing constraints. For example, two constrains change the modified $CF_{new}$ where constraints are not met. The constrains can include two boundaries.

The two constrains are:
1. If CFnew>UP_Boundary then CFnew=UP_Boundary.
2. If CFnew<DOWN_Boundary then CFnew=DownBoundary.

where UP_Boundary and DOWN_Boundary can be defined as follows:

UP_Boundary is defined as the smallest CF in {CF(i), LOG(i)} in which the minimum sensor level reached in the relevant LOG(i) was above a certain threshold, for example 70 mg/dl.

DOWN_Boundary can be defined according to the following:

The largest CF which caused minimum sensor value below 50 is defined to be CF1 with minimum sensor level LEV1.

The smallest CF which caused minimum sensor value above 50 is defined to be CF2 with minimum sensor level LEV2.

If both CFs exists and CF1<CF2, the lower boundary is defined as:

DOWN_Boundary=(70−LEV1)/(LEV2−LEV1)*(CF2−CF1)+CF1.

The following is the results of clinical trials using the monitoring system and method of the present invention:

The study group consisted of 7 patients, 5 female and 2 male, aged 19-30 years. Mean duration of diabetes was 10±4 years; mean HbA1C, 6.6±0.7%; and mean body mass index, 22±2.5 kg/m². The patients' demographic data, diabetes history, and other significant medical history were recorded, in addition to height, weight, and HbAlc level. The patients wore a CGS (Freestyle Navigator™, Abbott Diabetes Care, Alameda, Calif., USA or STS-Seven® System, DexCom, San Diego, Calif., USA) and recorded their meals and physical activities for 3-5 consecutive days. These data and corresponding insulin doses (downloaded from the insulin pump) were used to formulate the patient's treatment history for application in the monitoring system of the present invention.

Short-acting insulin analogue (NovoRapid®, Novo Nordisk, Bagsvaerd, Denmark) was used in the clinical trials. The CGS readings were entered (automatically or manually) into the monitoring system of the present invention every five minutes, and the system provided an insulin dose recommendation after each entry.

The control-to-range was set at 90-140 mg/dl, and the control-to-target, at 110 mg/dl. Each clinical session was supervised by a diabetologist who had to approve any treatment recommendation before it was automatically or manually delivered by the pump to the patient. Reference blood glucose levels were measured by the YSI 2300 STAT Plus (YSI, USA) every 30 minutes, Carbohydrate was administered when the reference blood glucose level dropped below 70 mg/dl.

8-hour closed-loop sessions were conducted in the resting state under two conditions: fasting or meal. The subject's insulin pump was replaced by the research insulin pump (OmniPod Insulin Management System™, Insulet Corp, Bedford, Mass., USA or MiniMed Paradigm® 722 Insulin Pump, Medtronic, Northridge, Calif., USA). In the fasting closed-loop condition, subjects arrived to the clinic in the morning (usually 08 h00) after an overnight fast and were instructed to measure their blood glucose at wake up (usually 06 h30). If the level was below 120 mg/dl with no hypoglycemia, they were asked to eat 1-2 slices of bread. In the closed-loop sessions with meal challenge, patients arrived to the clinic after about an 8 hours' fast and consumed a mixed meal with a carbohydrate content of 40-60 gr.

Two 24-hour closed-loop visits were conducted. Subjects arrived to the clinic in the afternoon after a fast of at least 3 hours. The subject's insulin pump was replaced with a modified OmniPod insulin pump which has communication abilities to a regular PC. Three standard mixed meals were consumed at 19 h30, 08 h00 and 13 h00, based on the patient's regular diet. The estimated carbohydrate content for each meal was 17.5 to 70 gr. Each patient slept for 7-8 hours at night during the study.

To examine the control performances of the monitoring system of the present invention during the 8-hour closed-loop sessions, two parameters were analyzed: glucose excursion and degree of stabilization.

Glucose excursion is determined by the peak postprandial glucose level and the time from initiation of closed-loop control to return of the glucose level to below 180 mg/dl.

Stable glucose levels were defined as a change of +1-10 mg/dl for a period of at least 30 minutes. The time from initiation of closed-loop control or mealtime until the stable state was attained, and the average glucose level at the stable state, were calculated.

In addition, 24-hour closed-loop control and the patient's home open-loop control were compared. The percent of glucose readings within, above, and below the range of 70-180 mg/dl was determined. The data set of the open-loop control included sensor readings from the 3-day period prior to the 24-hour closed-loop session. Control variability grid analysis (CVGA) [9] served as an auxiliary outcome measure. In this analysis, the open-loop data set included sensor readings from a period of 9-16 days. CVGA was performed over two time periods: 24 hours and night-time (00 h00-08 h00).

During all of the experiments, diabetes physicians approved each and every one of the monitoring system of the present invention treatment suggestions.

Reference is made to Table 3 summarizing the average and ranges results of the 8-hours closed loop sessions clinical studies.

|  | Average | Range |
|---|---|---|
| Fasting sessions |  |  |
| BG at beginning of closed loop session [mg/dL] | 237 | 178-300 |
| Time to below 180 mg/dL from system connection [hour] | 2.13 | 0.5-4.43 |
| Time to stable BG levels [hours] | 4.4 | 2.3-6.75 |
| BG level at stabilization [mg/dL] | 112 | 77-155 |
| Meal sessions |  |  |
| BG at beginning of closed loop session [mg/dL] | 96 | 70-138 |
| Peak Post prandial BG level [mg/dL] | 234 | 211-251 |
| Time to below 180 mg/dL from meal onset [hours] | 2.56 | 2.18-3 |
| Time to stable BG levels [hours] | 3.43 | 3-4.3 |
| BG level at stabilization [mg/dL] | 102 | 70-134.5 |

A total of nine closed-loop control sessions were conducted under fasting conditions at rest with six subjects. The average blood glucose level was 237 mg/dl at initiation of closed-loop control and decreased to 106 mg/dl within 4.4 hours. There were no hypoglycemic episodes.

During one of the fasting session, the monitoring system of the present invention succeeded to prevent a hypoglycemic episode after an overdose of insulin was delivered by the patient before his arrival to the clinic. The monitoring system of the present invention detected the overall trend in the patient's glucose level, took the overdose into account, and then decreased the insulin basal rate to full stop. This action successfully lowered the patient's glucose levels to a stable average of 80 mg/dl within 2 hours.

Three meal-challenge sessions were conducted with two subjects. The meal was detected and treated by the module 23 minutes on average after meal consumption. Peak postprandial glucose levels were 234 mg/dl on average, with a maximum of 251 mg/dl (see Table 3). Blood glucose levels, for the meal-challenge sessions, decreased to below 180 mg/dl within 2.5 hours on average and stabilized in the normal range within 3.5 hours for at least one hour.

Two 24-hour closed-loop sessions were conducted subjects #1 (Female, age 30 yr, BMI 22.9 kg/m², HbAlc 5.9% with 19 years of diabetes duration) and #2 (Male, age 23 yr, BMI 21.2 kg/m², HbAlc 7% with 8 years of diabetes duration). During the night, blood glucose levels ranged between 80 and 160 mg/dl, with a nadir of 93 mg/dl for subject #1 and 80 mg/dl for subject #2.

Reference is made to FIGS. 21A-21D illustrating a 24-hour closed-loop session with subject #1. Glucose levels peaked at 260 mg/dl after dinner, 190 mg/dl after breakfast and 210 mg/dl after lunch. The corresponding values for subject #2 were 221 mg/dl, 211 mg/dl and 219 mg/dl. Between meals, glucose levels returned to below 180 mg/dl within a mean of 2.7±0.8 hours for both subjects. Mean peak postprandial glucose level for overall sessions (8- and 24-hour) was 224±22 mg/dl, and glucose level returned to below 180 mg/dl at a mean interval of 2.6±0.6 hours. Mean time to stabilization was 4±1 hours.

Figure 21A:
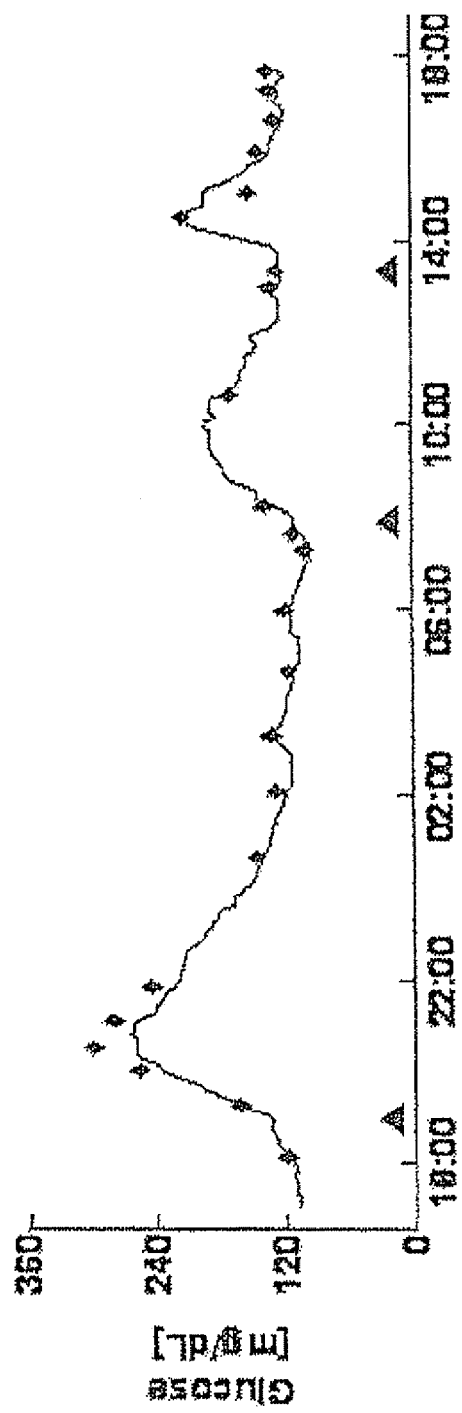
FIGS. 21A-21D are 24 hours closed loop session results conducted on a subject.
Figure 21B:
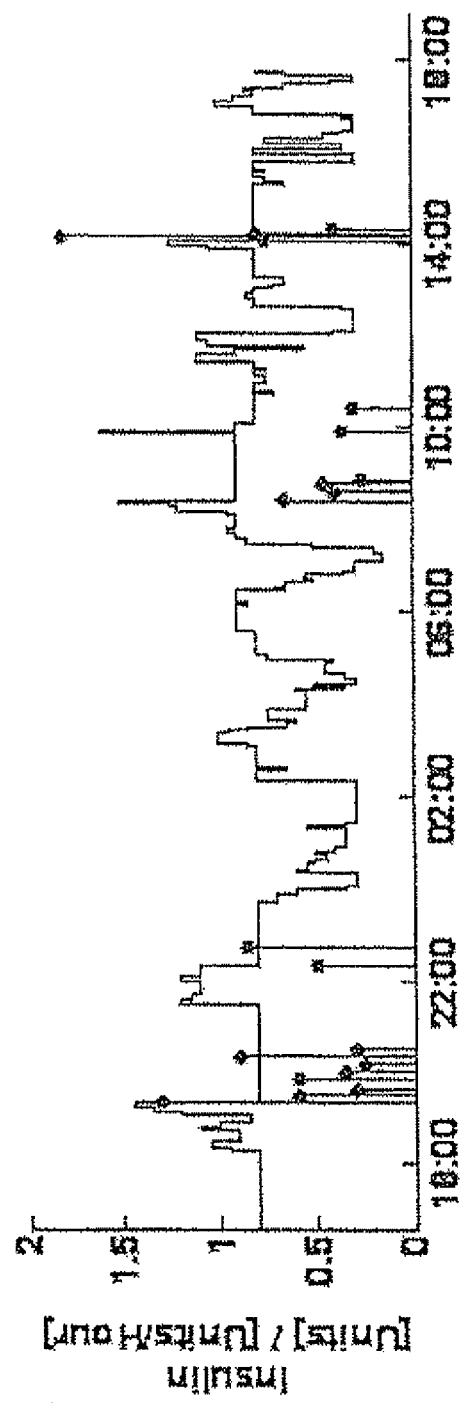
Figures 21C, 21D:
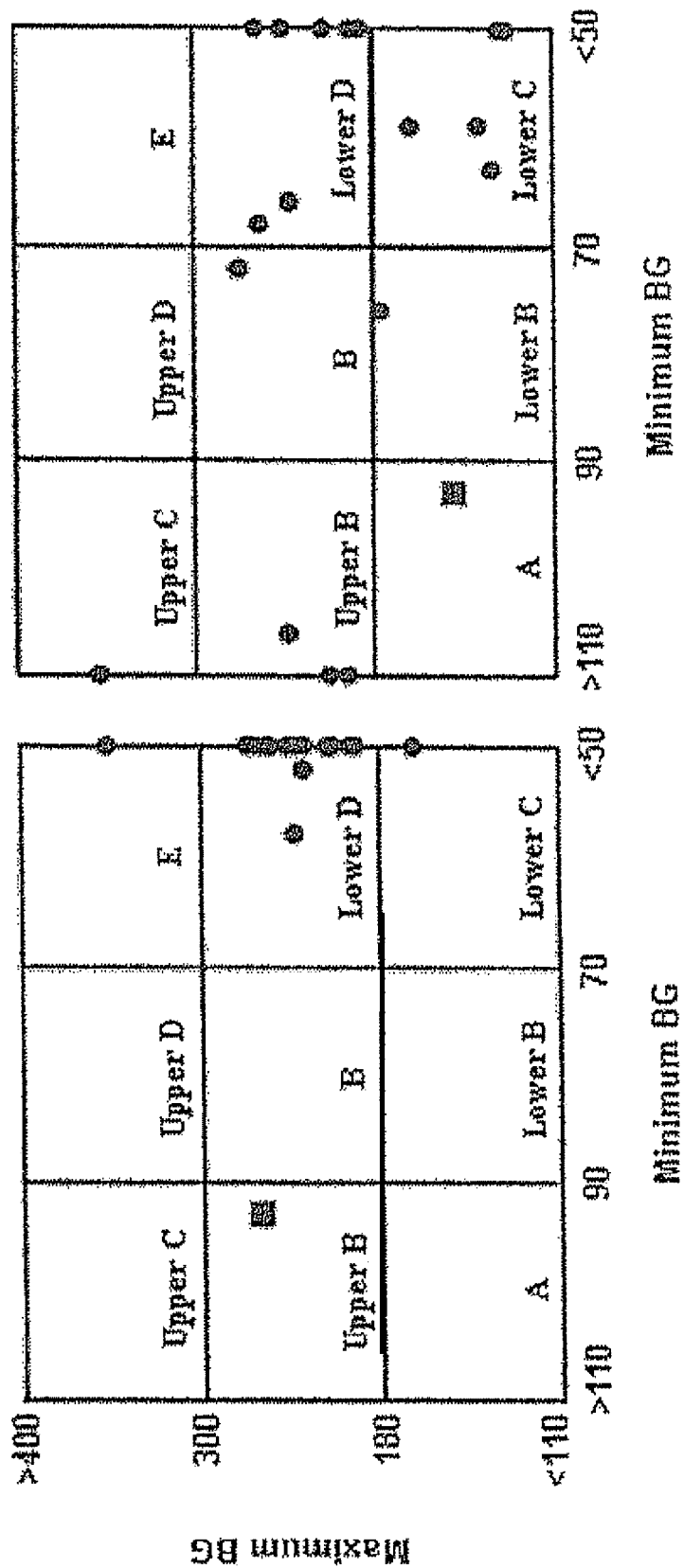

FIG. 21A shows the glucose trace including CGS readings (black line) reference measurements (black diamond) and the meal times (black triangles). FIG. 21B shows the insulin treatment (the horizontal lines represent the basal rate, vertical lines with dark circles represent insulin boluses line—basal rate and stem—insulin boluses) delivered by the monitoring system of the present invention during the 24-hour closed-loop trial with subject #1. Results from control performances comparison between home care (circles) and the monitoring system of the present invention (rectangular) using the Control Variability Grid Analysis (CVGA) [9] are shown on FIG. 21C (time period of 24 hours) and FIG. 21D during night time. FIG. 21C shows a control variability grid analysis (CVGA) over a time period of 24 hours for subject #1. FIG. 21D shows a control variability grid analysis overnight (00:00-08:00) for subject #1. The nine zones of the CVGA are associated with different qualities of glycemic regulation: A—accurate control, Lower B—benign deviations into hypoglycemia, B—benign control deviations, Upper B—benign deviations into hyperglycemia, Lower C—over correction of hypoglycemia, Upper C—over correction of hyperglycemia, Lower D—failure to deal with hypoglycemia, Upper D—failure to deal with hyperglycemia, and E—erroneous control. In both figures, the circles represent the minimum/maximum glucose level taken from the relevant time period glucose readings during home care and the rectangles indicate the levels during the closed-loop session regulated by using the monitoring system of the present invention.

Based on the control performances analysis, glucose control was found to be better during the 24 hours closed-loop sessions regulated by using the method of the present invention than the pre-study home care.

Seventy-three percent of the sensor values measured 70-180 mg/dl during closed-loop control compared to 70.5% over the 3-day open-loop period prior to the trial day. In addition, none of the sensor readings were below 70 mg/dl during closed-loop control compared to 15.3% for open-loop control. However, 27% of the sensor values were above 180 mg/dl during closed-loop control compared to 14.2% during open-loop control. On CVGA, the monitoring system was maintained benign control over a 24-hour perspective whereas the subjects at home care overcorrected and failed to manage hypoglycemia. During the night as well, the monitoring system maintained benign or accurate control, whereas home care was characterized by great variability. The analysis results for subject #1 are presented in FIGS. 21C-21D.

As illustrated in FIGS. 21C and 21D, CVGA was used to compare the performance of the monitoring system and home open-loop control. The results showed that during open-loop control, there was at least one recording of glucose below 60 mg/dl per day for both subject #1 and subject #2 (FIG. 21C). In general, these values appeared after daytime meals, indicating poor postprandial control of glucose excursions. Although only two 24-hour closed-loop experiments were conducted, CVGA revealed a great improvement with the monitoring system during the day and night (FIGS. 21C and 21D). Whereas peak postprandial glucose values were similar in both systems, only the monitoring system prevented late postprandial hypoglycemia.

No events of hypoglycemia occurred during either the 8-hour or 24-hour closed-loop sessions. On two occasions (8-hour closed-loop sessions), an impending hypoglycemic event was detected, with glucose levels ranging between 62-65 mg/dl for about 10 minutes. Although the subjects did not experience any symptoms of hypoglycemia, our physician decided to administer 15 gr of fast carbohydrate for safety reasons.

Feasibility studies were conducted in seven adults with type 1 diabetes (age, 19-30 yr; mean diabetes duration, 10±4 yr; mean HbA1C, 6.6±0.7%). All underwent 14 full closed-loop control sessions of 8 hours (fasting and meal state) and 24 hours.

The mean peak postprandial (overall sessions) glucose level was 224±22 mg/dl. Postprandial glucose levels returned to below 180 mg/dl within 2.6±0.6 hours and remained stable in the normal range for at least one hour. During 24-hour closed-loop control, 73% of the sensor values ranged between 70-180 and mg/dl, 27% were above 180 mg/dl, and none were below 70 mg/dl. There were no events of symptomatic hypoglycemia during any of the trials.

Glucose levels were maintained in the near normal range (80-160 mg/dl) at night. The monitoring system prevented nocturnal hypoglycemia by detecting the overall descending trend in the patient's glucose level and then decreasing the insulin basal rate to full stop. In 2 of the 14 closed-loop sessions, there was a short incident of impending asymptomatic hypoglycemia. The subjects had experienced a symptomatic nocturnal hypoglycemia event (below 50 mg/dl) prior to the clinic day, which was treated at home. The monitoring system made reasonable treatment suggestions, which were approved by the diabetes physician in charge, and responded to the descending trend of glucose by lowering the patient's basal rate to full stop. The physician considered the increase in the risk of recurrent hypoglycemia and therefore stopped the experiment.

As used in the specification and the appended claims and in accordance with long-standing patent law practice, the singular forms "a" "an" and "the" generally mean "at least one", "one or more", and other plural references unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Further, all numerical values, e.g. when referring to conditions, such as a time window, timestamp, glucose measurements, or insulin dosage etc. are approximations which are varied (+) or (−) by up to 20%, at times by up to 10% from the stated values. It is to be understood, even if not always explicitly stated that all numerical designations are preceded by the term "about". In addition, the calculated parameters of the present invention can be modified or varied to approximations of same which are varied (+) or (−) by up to 20%.

The invention will now be exemplified in the following description of non-limiting examples that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described here in below.

The invention claimed is:

1. A monitoring system for use with diabetic treatment management, the monitoring system comprising:
 a communication interface configured and operable to permit access to stored raw log data obtained over a certain time and being time spaced data points of glucose measurements, meals consumed and insulin delivery;
 a control unit configured for receiving and processing said raw log data, the control unit comprising:
 a sectioning module configured to section the raw log data within at least one time window; the sectioned time window being at least one of Basal data Section (BaS), Meals data Section (MS) and Bolus data Section (BS), each sectioned time window having a starting point and having an end point such that the BaS being selected outside an effect window of either a meal event or an insulin bolus, the MS being selected at a predetermined time ahead of a meal data point, and the starting point of the BS being selected as one of the following: (a) the end point of the MS or the BaS, and (b) an insulin bolus data point which is outside the MS; the end point of the BS being selected as one of the following, (i) the starting point of the MS or BaS and (ii) a predetermined time ahead of the insulin bolus data point without any intervening insulin bolus; and
 an unsupervised learning controller configured and operable to determine an informative data piece from a residual log data portion of said raw log data, analyze said informative data piece and select a sectioned time window for calculation of an individualized patient's profile related data comprising at least one of global insulin pump setting of basal rate, correction factor (CF), carbohydrate ratio (CR) and insulin activity curve parameters, wherein calculation of the basal rate is based on BaS, calculation of at least one of insulin activity curve parameters, correction factor (CF) and carbohydrate ratio (CR) is based on MS, and calculation of the correction factor (CF) or insulin activity curve parameters is based on BS.

2. The system of claim 1, wherein said raw log data is acquired in accordance with a preprogrammed sampling pattern.

3. The system of claim 1, wherein said unsupervised learning controller is configured and operable determine each of said parameters from a part of said informative data piece corresponding to a selected time window of said certain time.

4. The system of claim 1, wherein the received raw log data corresponds to a memory image at the access time irrespective of any user interaction.

5. The system of claim 1, wherein said control unit comprises a controller associated with said communication interface and preprogrammed for receiving said data according to a predetermined sampling time pattern.

6. The system of claim 1, wherein the received stored data corresponds to a memory image at the access time irrespective of any user interaction.

7. The system of claim 1, comprising a memory module configured and operable to maintain said stored data.

8. The system of claim 1, wherein the stored data is being obtained from a remote controller.

9. The system of claim 8, wherein the stored data is accessible via asynchronous operation independent of a user operation.

10. The system of claim 1, wherein the stored data is a memory image of a remote controller independently accumulating said information.

11. The system of claim 1, wherein the stored data is being obtained from a remote controller independently accumulating said information over time.

12. The system of claim 1, wherein the information indicative glucose sensor readings, insulin delivery and meals recordation is a file obtained from a remote controller independently accumulating said information.

13. The system of claim 1, wherein the stored data decoded in a file.

14. The system of claim 12, wherein the file is downloaded from a network and stored in a memory module.

15. A method for use in determination of insulin pump settings, the method comprising:
 performing unsupervised learning of the insulin pump settings, said unsupervised learning comprising:
 a) obtaining raw log data input accumulated on one or more glucose monitoring units recording glucose levels of a single treated patient along a certain time;
 b) sectioning the raw log data to predetermined data sections; each of the predetermined data sections being at least one of Basal data Section (BaS), Meals data Section (MS) and Bolus data Section (BS), each section having a starting point and having an end point such that the BaS being selected outside an effect window of either a meal event or an insulin bolus, the MS being selected at a predetermined time ahead of a meal data point, and the starting point of the BS being selected as one of the following: (a) the end point of the MS or the BaS, and (b) an insulin bolus data point which is outside the MS; the end point of the BS being selected as one of the following, (i) the starting point of the MS or BaS and (ii) a predetermined time ahead of the insulin bolus data point without any intervening insulin bolus;
 c) determining informative data piece from raw log data input being sectioned to data sections, the informative data piece being determined from said data section; and
 d) calculating global insulin pump settings from the informative data piece, wherein said settings include at least one parameter of basal plan, Carbohydrate Ratio (CR), Correction Factor (CF) or Active Insulin Function (AIF) wherein calculation of the basal rate is based on BaS, calculation of at least one of insulin activity curve parameters, correction factor (CF) and carbohydrate ratio (CR) is based on MS, and calculation of the correction factor (CF) or insulin activity curve parameters is based on BS.

16. The method of claim 15 further includes aligning plurality of data portions of said raw log data input along a shared time axis.

17. The method of claim 15 wherein data portions are basal periods.

18. The method of claim 16, including determining a representative data point comprising both a value of aggregated blood glucose levels and a time stamp; the representative data point is paired to a selected basal period; the representative data point indicates a basal rate determination for the selected basal period.

19. The method of claim 15 wherein the raw log data input of said Basal Section (Bas) includes a series of basal rates as a function of time; the method comprising: determining a time delay characterizing the treated patient at said Basal Section (Bas), said time delay being between a basal treatment rate and changes in the glucose level; obtaining a plurality of selected basal rates at a delivery time, a respective paired glucose level being at the time delay measured from the delivery time; determining a resultant basal rate from the plurality of selected basal rates which minimizes a change in the glucose level.

20. The method of claim 15, comprising determining an Active Insulin Function (AIF) by carrying out the following method:
   a) obtaining a set of glucose measurements and paired time stamps for the raw log data in the time section;
   b) normalizing each glucose measurement of the set thereby obtaining a series of normalized glucose measurements and paired time stamp;
   c) Processing said normalized glucose measurements and paired time stamp into a substantially monotonic non-increasing series; thereby obtaining the Active Insulin Function (AIF).

21. The method of claim 15, wherein carbohydrate ratio (CR) is determined from raw log data input from MS Sections.

22. The method of claim 21 wherein the carbohydrate ratio (CR) is calculated from practical carbohydrate ratios (pracCR) defined as ratio of carbohydrate consumed to delivered insulin for an MS Section.

23. The method of claim 21, including determining plurality of glucose level and paired practical carbohydrate ratios for the MS Section; the paired practical carbohydrate ratios being a candidate carbohydrate ratios defining a curve.

24. The method of claim 22, wherein the carbohydrate ratio (CR) setting is determined from the candidate practical carbohydrate ratios.

25. The method of claim 22, wherein the carbohydrate ratio (CR) for the meal is calculated by calculating a just-in-time AIF setting to estimate the active insulin in the MS Section.

26. The method of claim 23, wherein carbohydrate ratio (CR) setting is determined by selecting a function which fits the curve of the paired practical carbohydrate ratios.

27. The method of claim 23, wherein carbohydrate ratio (CR) setting is determined by a majority voting procedure.

28. The method of claim 15, wherein the correction factor (CF) for a meal is determined from the raw log data input of the MS Section.

29. The method of claim 27, wherein the correction factor (CF) for the meal is calculated by processing the AIF to estimate the active insulin in the MS Section and a just-in-time carbohydrate ratio (CR).

30. The method of claim 15, wherein a non-meal correction factor (CF) is determined from the raw log data input of a BS Section.

31. The method of claim 15, wherein the correction factor (CF) is modified in accordance with the following parameters:
   a proportion between a minimum sensor reading during a time window or section, a lowest blood glucose reading recorded outside impending hypoglycaemia and hypoglycaemia time periods; and
   a maximum sensor reading in a time slot prior to obtaining the minimum sensor reading.

32. The method of claim 15, wherein a plurality of candidate correction factors (CF) are determined and the correction factor (CF) setting is determined by a voting procedure.

33. The method of claim 15, wherein said obtaining of the raw log data input is performed by uploading said raw log data input to enable communication of the raw log data input to an unsupervised learning controller.

34. A method for determining an Active Insulin Function (AIF) for use in insulin treatment of a patient, the method comprising:
   a) obtaining raw log data obtained over a certain time and being indicative of glucose measurements of the patient,
   b) sectioning the raw log data being indicative of glucose measurements, meals events and insulin delivery of the patient to predetermined data sections; each of the predetermined data sections being at least one of Meals data Section (MS) and Bolus data Section (BS), each section having a starting point and having an end point such that the MS being selected at a predetermined time ahead of a meal data point, and the starting point of the BS being selected as one of the following: (a) the end point of the MS or the BaS, and (b) an insulin bolus data point which is outside the MS; the end point of the BS being selected as one of the following, (i) the starting point of the MS or BaS and (ii) a predetermined time ahead of the insulin bolus data point without any intervening insulin bolus;
   c) obtaining a set of glucose measurements and paired time stamps for the raw log data in the time section;
   d) normalizing each glucose measurement of the set thereby obtaining a series of normalized glucose measurements and paired time stamp;
   e) processing said normalized glucose measurements and paired time stamp into a substantially monotonic non-increasing series; thereby obtaining the Active Insulin Function (AIF).

35. A control unit for use with diabetic treatment management, the control unit comprising: a data processor utility configured and operable as an unsupervised learning controller preprogrammed for processing raw log data input obtained over a certain time and being indicative of glucose measurements, meals events and insulin delivery, said processing comprising sectioning the raw log data to predetermined data sections; each of the predetermined data sections being at least one of Basal data Section (BaS), Meals data Section (MS) and Bolus data Section (BS), each section having a starting point and having an end point such that the BaS being selected outside an effect window of either a meal event or an insulin bolus, the MS being selected at a predetermined time ahead of a meal data point, and the starting point of the BS being selected as one of the following: (a) the end point of the MS or the BaS, and (b) an insulin bolus data point which is outside the MS; the end point of the BS being selected as one of the following, (i) the starting point of the MS or BaS and (ii) a predetermined time ahead of the insulin bolus data point without any intervening insulin bolus; determining an informative data piece from residual log data portion of said raw log data and selecting said informative data piece for further processing to determine at least one of basal rate, correction factor (CF), carbohydrate ratio (CR) and insulin activity curve parameters, and generating global insulin pump settings wherein calculation of the basal rate is based on BaS, calculation of at least one of insulin activity curve parameters, correction factor (CF) and carbohydrate ratio (CR) is based on MS, and calculation of the correction factor (CF) or insulin activity curve parameters is based on BS.

36. A computer program recordable on a storage medium and comprising a machine readable format, the computer program being configured and operable to, when being accessed, carry out the following: identifying raw log data input corresponding to a certain time period and comprising glucose measurements, meals events and insulin delivery; sectioning the raw log data to predetermined data sections; each of the predetermined data sections being at least one of Basal data Section (BaS), Meals data Section (MS) and Bolus data Section (BS), each section having a starting point and having an end point such that the BaS being selected outside an effect window of either a meal or an insulin bolus, the MS being selected at a predetermined time ahead of a meal data point, and the starting point of the BS being selected as one of the following: (a) the end point of the MS or the BaS, and (b) an insulin bolus data point which is outside the MS; the end point of the BS being selected as one of the following, (i) the starting point of the MS or BaS and (ii) a predetermined time ahead of the insulin bolus data point without any intervening insulin bolus; determining an informative data piece and residual log data portion of said raw log data; selecting said informative data piece and calculating therefrom at least one of basal rate, correction factor (CF), carbohydrate ratio (CR) and insulin activity curve parameters, and generating output data comprising values for global insulin pump settings wherein calculation of the basal rate is based on BaS, calculation of at least one of insulin activity curve parameters, correction factor (CF) and carbohydrate ratio (CR) is based on MS, and calculation of the correction factor (CF) or insulin activity curve parameters is based on BS.

37. The monitoring system of claim 1, further comprising a processing unit comprising:
a first processor module for processing measured data indicative of blood glucose level and generating first processed data indicative thereof,
a second processor module comprising at least one fuzzy logic module; said fuzzy logic module receives input parameters corresponding to the measured data, the first processed data and a reference data including said individualized patient's profile related data, individualized patient's treatment history related data, processes the received parameters to produce at least one qualitative output parameter indicative of patient's treatment parameters; such that said second processor module determines whether any of the treatment parameters is to be modified and generate corresponding output data which can be supplied directly to the pump and/or presented through a user interface to an authorized person (patient and/or physician) for a decision making and/or recording.

38. The system of claim 37, wherein said input parameters include at least one of the following input parameters: past blood glucose level trend, current blood glucose level, future blood glucose level trend, future blood glucose level.

39. The system of claim 37, wherein said at least one fuzzy logic module is characterized by at least one of the following: (i) it comprises a set of rules associated with contribution factors and at least one fuzzy engine utilizing one or more member functions modeled for translating the input parameters into at least one qualitative output parameter; and (ii) is configured and operable to provide the at least one output parameter comprising data indicative of at least one of bolus glucagon, bolus insulin and basal insulin treatment, said second processor module thereby providing control to range output treatment suggestion based on the output parameter of the fuzzy logic module.

40. The system of claim 37, wherein said processing unit comprises a third processor module receiving said at least one qualitative output parameter of the fuzzy logic module and said input parameters corresponding to the measured data, the first processed data and the reference data, and processing said at least one output parameter said input parameters to determine whether any of the treatment parameters is to be modified and generate corresponding output data which can be supplied directly to the pump and/or presented through the user interface to an authorized person (patient and/or physician) for a decision making and/or recording, said treatment parameters comprising at least one of dosing of insulin and glucagon to be delivered.

41. The system of claim 40, wherein the at least one output parameter of the at least one fuzzy logic module comprises data indicative of at least one of bolus glucagon, bolus insulin and basal insulin treatment, and said second processor module thereby provides control to range output treatment suggestion based on the output parameter of the fuzzy logic module, the third processor receiving the control to range output treatment suggestion, and determining said amount in accordance with at least one of a glucose target of the patient's profile, patient's insulin or glucagon pharmacodynamics, and said measured data.

42. The system of claim 37, wherein said processing unit is operable to update and/or calibrate said individualized patient's profile related data during treatment or during monitoring procedure.

43. The system of claim 37, wherein said individualized patient's profile related data comprises parameters selected from at least one of global pump settings, insulin sensitivity, glucagon sensitivity, basal plan, insulin/glucagon pharmacokinetics associated data, glucose target level or target range level, and insulin/glucagon activity model.

44. The system of claim 37, wherein said individualized patient's treatment history related data comprises patient's insulin delivery regimen given to the patient at different hours of the day.

45. The system of claim 37, wherein said second processor module comprises a fuzzy logic module operable in response to an event being invoked by a detector module analyzing at least one pattern of glucose levels indicative of at least one event, said event comprising at least one of sleep, meal, exercise and disease event or rest.

46. The system of claim 45, wherein said system is configured and operable to alternate between at least two fuzzy logic modules, each handling a different event.

47. The system of claim 46, wherein said second processor module is operable as a meal treatment module and is configured to monitor the blood glucose level.

48. The system of claim 47, wherein said input parameters further include at least one of the following input parameters: time elapsed between detected special events, blood glucose level with respect to said special event.

49. The system of claim 37, wherein said measured data is obtained at a certain time, said measured data comprising at least one of current and past glucose levels relative to said certain time.

* * * * *